US008765663B2

(12) United States Patent
Seehra et al.

(10) Patent No.: US 8,765,663 B2
(45) Date of Patent: Jul. 1, 2014

(54) METHODS FOR INCREASING ADIPONECTIN

(75) Inventors: Jasbir Seehra, Lexington, MA (US); Ravindra Kumar, Acton, MA (US); Jennifer Lachey, Arlington, MA (US); Alan Koncarevic, Chicago, IL (US)

(73) Assignee: Acceleron Pharma Inc., Cambridge, MA (US)

( * ) Notice: Subject to any disclaimer, the term of this patent is extended or adjusted under 35 U.S.C. 154(b) by 0 days.

(21) Appl. No.: 13/404,593

(22) Filed: Feb. 24, 2012

(65) Prior Publication Data

US 2012/0156204 A1 Jun. 21, 2012

Related U.S. Application Data

(63) Continuation of application No. 12/657,146, filed on Jan. 13, 2010, now Pat. No. 8,138,142.

(60) Provisional application No. 61/204,946, filed on Jan. 13, 2009.

(51) Int. Cl.
*A61K 38/00* (2006.01)
*A61K 39/00* (2006.01)
*A61K 39/395* (2006.01)

(52) U.S. Cl.
USPC ....... 514/1.1; 514/7.4; 424/130.1; 424/133.1; 424/135.1; 424/141.1; 424/143.1

(58) Field of Classification Search
None
See application file for complete search history.

(56) References Cited

U.S. PATENT DOCUMENTS

| | | | |
|---|---|---|---|
| 4,973,577 | A | 11/1990 | Vale, Jr. et al. |
| 5,118,667 | A | 6/1992 | Adams et al. |
| 5,658,876 | A | 8/1997 | Crowley et al. |
| 5,703,043 | A | 12/1997 | Celeste et al. |
| 5,760,010 | A | 6/1998 | Klein |
| 5,808,007 | A | 9/1998 | Lee et al. |
| 5,824,637 | A | 10/1998 | Crowley et al. |
| 5,847,078 | A | 12/1998 | Eto et al. |
| 5,885,794 | A | 3/1999 | Mathews et al. |
| 6,004,780 | A | 12/1999 | Soppet et al. |
| 6,093,547 | A | 7/2000 | Jin et al. |
| 6,132,988 | A | 10/2000 | Sugino et al. |
| 6,162,896 | A | 12/2000 | Mathews et al. |
| 6,287,816 | B1 | 9/2001 | Rosen et al. |
| 6,440,930 | B1 | 8/2002 | Rinella, Jr. |
| 6,451,334 | B2 | 9/2002 | Perrine |
| 6,537,966 | B1 | 3/2003 | Duan et al. |
| 6,548,634 | B1 | 4/2003 | Ballinger et al. |
| 6,599,876 | B2 | 7/2003 | Kojima |
| 6,605,699 | B1 | 8/2003 | Ni et al. |
| 6,656,475 | B1 | 12/2003 | Lee et al. |
| 6,656,708 | B1 | 12/2003 | Yu et al. |
| 6,692,925 | B1 | 2/2004 | Miyazono et al. |
| 6,696,260 | B1 | 2/2004 | Lee et al. |
| 6,777,205 | B1 | 8/2004 | Carcagno et al. |
| 6,835,544 | B2 | 12/2004 | Mathews et al. |
| 6,891,082 | B2 | 5/2005 | Lee et al. |
| 7,192,717 | B2 | 3/2007 | Hill et al. |
| 7,202,210 | B2 | 4/2007 | Wolfman et al. |
| 7,261,893 | B2 | 8/2007 | Veldman et al. |
| 7,320,789 | B2 | 1/2008 | Dunham et al. |
| 7,560,441 | B2 | 7/2009 | Wolfman et al. |
| 7,612,041 | B2 | 11/2009 | Knopf et al. |
| 7,709,605 | B2 | 5/2010 | Knopf et al. |
| 7,842,663 | B2 | 11/2010 | Knopf et al. |
| 7,893,213 | B2 | 2/2011 | Mathews et al. |
| 7,988,973 | B2 | 8/2011 | Sherman |
| 8,007,809 | B2 | 8/2011 | Sherman |
| 8,058,229 | B2 | 11/2011 | Seehra et al. |
| 8,138,142 | B2 | 3/2012 | Seehra et al. |
| 8,178,488 | B2 | 5/2012 | Knopf et al. |
| 8,216,997 | B2 | 7/2012 | Seehra et al. |
| 8,252,900 | B2 | 8/2012 | Knopf et al. |
| 8,293,881 | B2 | 10/2012 | Seehra et al. |
| 8,343,933 | B2 | 1/2013 | Knopf et al. |
| 8,388,968 | B2 | 3/2013 | Berger et al. |
| 2001/0039036 | A1 | 11/2001 | Mathews et al. |
| 2003/0083251 | A1 | 5/2003 | Westenfelder |
| 2003/0118556 | A1 | 6/2003 | Kaspar et al. |
| 2003/0144203 | A1 | 7/2003 | Bowen |
| 2004/0033511 | A1 | 2/2004 | Pfizenmaier et al. |

(Continued)

FOREIGN PATENT DOCUMENTS

| | | | |
|---|---|---|---|
| EP | 1 174 149 | A1 | 1/2002 |
| EP | 1 362 062 | A1 | 11/2003 |

(Continued)

OTHER PUBLICATIONS

Abaza, M.S.I., et al., "Effects of Amino acid Substitutions Outside an Antigenic Site," J. Protein Chem., 11(5):433-444 (1992).

(Continued)

*Primary Examiner* — Gyan Chandra
(74) *Attorney, Agent, or Firm* — Ropes & Gray LLP

(57) ABSTRACT

In certain aspects, the present invention provides compositions and methods for increasing adiponectin in a patient in need thereof by administering an antagonist of an ActRIIB signaling pathway. Examples of such antagonists include ActRIIB polypeptides, anti-ActRIIB antibodies, anti-activin A and/or B antibodies, anti-myostatin antibodies, anti-GDF3 antibodies, and anti-BMP7 antibodies. Also provided are methods for ameliorating one or more undesired effects of anti-androgen therapy, including muscle loss, bone loss, increased adiposity, and/or increased insulin resistance. A variety of disorders may be treated by causing an increase in circulating adiponectin concentrations.

12 Claims, 26 Drawing Sheets
(21 of 26 Drawing Sheet(s) Filed in Color)

(56) References Cited

U.S. PATENT DOCUMENTS

| | | | |
|---|---|---|---|
| 2004/0132675 | A1 | 7/2004 | Kuo et al. |
| 2004/0138129 | A1 | 7/2004 | MacLeod |
| 2004/0197828 | A1 | 10/2004 | Gaddy |
| 2004/0209805 | A1 | 10/2004 | Phillips et al. |
| 2004/0223966 | A1 | 11/2004 | Wolfman et al. |
| 2005/0106148 | A1 | 5/2005 | Kay et al. |
| 2005/0197292 | A1 | 9/2005 | Smithson et al. |
| 2005/0244867 | A1 | 11/2005 | Soppet et al. |
| 2005/0257278 | A1 | 11/2005 | Lee et al. |
| 2006/0068468 | A1 | 3/2006 | Knopf et al. |
| 2006/0172347 | A1 | 8/2006 | Mellor et al. |
| 2006/0210657 | A1 | 9/2006 | Chou |
| 2007/0048830 | A1 | 3/2007 | Gilbert et al. |
| 2007/0149455 | A1 | 6/2007 | Wolfman et al. |
| 2007/0172956 | A1 | 7/2007 | Magari et al. |
| 2007/0184052 | A1 | 8/2007 | Lin et al. |
| 2007/0249022 | A1 | 10/2007 | Knopf et al. |
| 2007/0275895 | A1 | 11/2007 | Duan et al. |
| 2007/0292885 | A1 | 12/2007 | Bejanin et al. |
| 2008/0021104 | A1 | 1/2008 | Tarallo |
| 2008/0075692 | A1 | 3/2008 | Perrine |
| 2008/0089897 | A1 | 4/2008 | Wolfman |
| 2008/0102065 | A1 | 5/2008 | Borges et al. |
| 2008/0139590 | A1 | 6/2008 | Qian et al. |
| 2009/0005308 | A1 | 1/2009 | Knopf et al. |
| 2009/0017019 | A1 | 1/2009 | Shields et al. |
| 2009/0047281 | A1 | 2/2009 | Sherman |
| 2009/0074768 | A1 | 3/2009 | Knopf et al. |
| 2009/0087433 | A1 | 4/2009 | Wolfman et al. |
| 2009/0098113 | A1 | 4/2009 | Knopf et al. |
| 2009/0099086 | A1 | 4/2009 | Knopf et al. |
| 2009/0118188 | A1 | 5/2009 | Knopf et al. |
| 2009/0142333 | A1 | 6/2009 | Knopf et al. |
| 2009/0148436 | A1 | 6/2009 | LaVallie et al. |
| 2009/0163417 | A1 | 6/2009 | Sherman |
| 2010/0008918 | A1 | 1/2010 | Sherman et al. |
| 2010/0015144 | A1 | 1/2010 | Sherman et al. |
| 2010/0028331 | A1 | 2/2010 | Sherman et al. |
| 2010/0028332 | A1 | 2/2010 | Sherman et al. |
| 2010/0068215 | A1 | 3/2010 | Seehra et al. |
| 2010/0183624 | A1 | 7/2010 | Seehra et al. |
| 2010/0272734 | A1 | 10/2010 | Berger et al. |
| 2010/0316644 | A1 | 12/2010 | Seehra et al. |
| 2011/0070233 | A1 | 3/2011 | Seehra et al. |
| 2011/0092670 | A1 | 4/2011 | Knopf et al. |
| 2011/0129469 | A1 | 6/2011 | Koncarevic et al. |
| 2011/0135638 | A1 | 6/2011 | Seehra et al. |
| 2011/0218147 | A1 | 9/2011 | Knopf et al. |
| 2012/0003218 | A1 | 1/2012 | Sherman et al. |
| 2012/0015877 | A1 | 1/2012 | Seehra et al. |
| 2012/0052067 | A1 | 3/2012 | Sherman |
| 2012/0148588 | A1 | 6/2012 | Knopf et al. |
| 2012/0237521 | A1 | 9/2012 | Berger et al. |

FOREIGN PATENT DOCUMENTS

| | | | |
|---|---|---|---|
| EP | 1 416 273 | A1 | 5/2004 |
| WO | WO-92/04913 | A1 | 4/1992 |
| WO | WO-92/20793 | A1 | 11/1992 |
| WO | WO 93/00432 | A1 | 1/1993 |
| WO | WO-94/15965 | A1 | 7/1994 |
| WO | WO 94/26893 | A1 | 11/1994 |
| WO | WO-95/10611 | A1 | 4/1995 |
| WO | WO-95/29685 | A1 | 11/1995 |
| WO | WO-97/23613 | A2 | 7/1997 |
| WO | WO-99/06559 | A1 | 2/1999 |
| WO | WO-00/18932 | A2 | 4/2000 |
| WO | WO-00/43781 | A2 | 7/2000 |
| WO | WO-00/62809 | A1 | 10/2000 |
| WO | WO-01/36001 | A2 | 5/2001 |
| WO | WO-02/10214 | A2 | 2/2002 |
| WO | WO 02/22680 | A2 | 3/2002 |
| WO | WO-02/40501 | A2 | 5/2002 |
| WO | WO-02/43759 | A2 | 6/2002 |
| WO | WO-02/085306 | A2 | 10/2002 |
| WO | WO-02/094852 | A2 | 11/2002 |
| WO | WO-03/006057 | A1 | 1/2003 |
| WO | WO-03/053219 | A2 | 7/2003 |
| WO | WO-03/072808 | A1 | 9/2003 |
| WO | WO-2004/039948 | | 5/2004 |
| WO | WO-2004/108157 | A2 | 12/2004 |
| WO | WO-2005/003158 | A2 | 1/2005 |
| WO | WO-2005/009460 | A2 | 2/2005 |
| WO | WO-2005/014650 | A2 | 2/2005 |
| WO | WO-2005/028517 | A2 | 3/2005 |
| WO | WO 2005/053795 | A2 | 6/2005 |
| WO | WO-2005/070967 | A2 | 8/2005 |
| WO | WO-2005/094871 | A2 | 10/2005 |
| WO | WO-2005/097825 | A2 | 10/2005 |
| WO | WO 2005/113590 | A2 | 12/2005 |
| WO | WO-2006/002387 | A2 | 1/2006 |
| WO | WO-2006/012627 | A2 | 2/2006 |
| WO | WO-2006/020884 | A2 | 2/2006 |
| WO | WO-2006/039400 | A2 | 4/2006 |
| WO | WO-2006/083183 | A1 | 8/2006 |
| WO | WO-2006/088972 | | 8/2006 |
| WO | WO-2007/038703 | A2 | 4/2007 |
| WO | WO-2007/053775 | A1 | 5/2007 |
| WO | WO-2007/062188 | | 5/2007 |
| WO | WO-2007/067616 | A2 | 6/2007 |
| WO | WO-2007/076127 | A2 | 7/2007 |
| WO | WO 2008/015383 | A2 | 2/2008 |
| WO | WO-2008/031061 | | 3/2008 |
| WO | WO-2008/060139 | A1 | 5/2008 |
| WO | WO-2008/072723 | A1 | 6/2008 |
| WO | WO 2008/073292 | A2 | 6/2008 |
| WO | WO-2008/076437 | A2 | 6/2008 |
| WO | WO-2008/094708 | A2 | 8/2008 |
| WO | WO-2008/097541 | A2 | 8/2008 |
| WO | WO-2008/100384 | A2 | 8/2008 |
| WO | WO-2008/109167 | A2 | 9/2008 |
| WO | WO-2008/151078 | A8 | 12/2008 |
| WO | WO-2009/009059 | A1 | 1/2009 |
| WO | WO-2009/019504 | A1 | 2/2009 |
| WO | WO-2009/019505 | A2 | 2/2009 |
| WO | WO-2009/025651 | A1 | 2/2009 |
| WO | WO 2009/070243 | A2 | 6/2009 |
| WO | WO-2009/137075 | A1 | 11/2009 |
| WO | WO-2009/137613 | A2 | 11/2009 |
| WO | WO-2009/158015 | A2 | 12/2009 |
| WO | WO-2009/158025 | A2 | 12/2009 |
| WO | WO-2010/019261 | A1 | 2/2010 |
| WO | WO-2010/083034 | A1 | 7/2010 |
| WO | WO 2010/125003 | A1 | 11/2010 |
| WO | WO-2010144452 | A1 | 12/2010 |
| WO | WO-2010151426 | A1 | 12/2010 |
| WO | WO-2011020045 | A9 | 2/2011 |
| WO | WO-2011/031901 | A1 | 3/2011 |

OTHER PUBLICATIONS

Acceleron Pharma Presents Positive Phase 1 Results Demonstrating ACE-011 Increases Markers of Bone Formation, Acceleron Pharma, pp. 1-2, <www.acceleronpharma.com/contents/news/press-releases/detail.jsp/q/news-id/47> Downloaded from the Internet on Feb. 17, 2009.

Akel et al, Neutralization of Autocrine Transforming Growth Factor -β in Human Cord Blood $CD34^{+}CD38^{-}Lin^{-}$ Cells Promotes Stem-Cell-Factor-Mediated Erythropoietin-Independent Early Erythroid Progenitor Development and Reduces Terminal Differentiation. Stem Cells, 21:557-567 (2003).

Akpan, I., et al., "The effects of a soluble activin type IIB receptor on obesity and insulin sensitivity," International Journal of Obesity, 33(11):1265-1273 (2009).

Allendorph, G.P., et al., "Structure of the ternary signaling complex of a TGF-β superfamily member," PNAS, 103(20):7643-7648 (2006).

Attie et al., "A Single Ascending-Dose Study of Muscle Regulator Ace-031 in Healthy volunteers," Muscle & Nerve, pp. 1-8 (2012).

Banks, G.B., et al., "The Value of Mammalian Models for Duchenne Muscular Dystrophy in Developing Therapeutic Strategies," Current Topics in Developmental Biology, 84:431-453 (2008).

(56) References Cited

OTHER PUBLICATIONS

Benny Klimek, Margaret E., et al., "Acute inhibition of myostatin-family proteins preserves skeletal muscle in mouse models of cancer cachexia," Biochemical and Biophysical Research Communications, 391:1548-1554 (2010).
Berenson, J.R., "Multiple Myeloma," Multiple Myeloma: Plasma Cell Disorders: Merck Manual Professional, pp. 1-5, Jul. 2008.
Binkert, et al., "Cloning, sequence analysis and expression of a cDNA encoding a novel insulin-like growth factor binding protein (IGFBP-2)," The EMBO Journal, 8(9):2497-2502 (1989).
Bodey, B., et al., "Failure of Cancer Vaccines: The Significant Limitations of this Approach to Immunotherapy," Anticancer Research, 20:2665-2676 (2000).
Bogdanovich, S., et al., "Functional improvement of dystrophic muscle by myostatin blockade," Nature, 420:418-421 (2002).
Bowie, J.U., et al., "Deciphering the Message in Protein Sequences: Tolerance to Amino Acid Substitutions," Science, 257:1306-1310 (1990).
Broxmeyer, H.E., et al, "Selective and indirect modulation of human multipotential and erythroid hematopoietic progenitor cell proliferation by recombinant human activin and inhibin," Proc. Natl. Acad. Sci. USA, 85:9052-9056 (1988).
Burdette et al., Activin A mediates growth inhibition and cell cycle arest through Smads in human breast cancer cells. Cancer Research, 65(17):7968-7975; Abstract (2005).
Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," J. Cell Biol., 111:2129-2138 (1990).
Cadena, S.M., et al., "Administration of a Soluble Activin Type IIB Receptor Promotes Skeletal Muscle Growth Independent of Fiber Type," Journal of Applied Physiology, 109:635-642 (2010).
Caricasole, A. A. D., et al., "Human Growth-Differentiation Factor 3 (HGDF3): Developmental Regulation in Human Teratocarcinoma Cell Lines and Expression in Primary Testicular Germ Cell Tumors," Oncogene, 16:95-103 (1998).
Centrella et al., "Activin-A Binding and Biochemical Effects in Osteoblast-Enriched Cultures from Fetal-Rat Parietal Bone," Molecular and Cellular Biology, 11(1):250-58 (1991).
Chamberlain, R.S., et al., "Innovations and strategies for the development of anticancer vaccines," Expert Opinion on Pharmacotherapy, 1(4):603-614 (2000).
Chamow, S.M., and Ashkenazi, A., "Immunoadhesins: Principles and Applications," TIBTECH, 14: 52-60 (1996).
Chapman, B., et al., "Effect of intron A from human cytomegalovirus (Towne) immediate-early gene on heterologous expression in mammalian cells," Nucleic Acids Research, 19(14):3979-3986 (1991).
Chen, Y.G., et al. "Regulation of Cell Proliferation, Apoptosis, and Carcinogenesis by Activin," Exp. Biol. Med., 227(2):75-87 (2002).
Cirillo et al., "Hematocrit, blood pressure, and hypertension. The Gubbio Population Study," Hypertension, 20(3):319-326 (1992).
Coerver, et al., "Activin Signaling through Activin Receptor Type II Causes the Cachexia-Like Symptoms in Inhibin-Deficent Mice," 10(5):534-543 (1996).
Collins, C.D., "Multidisciplinary Symposium: Haematological Malignancies," Cancer Imaging 5:S119-S126 (2005).
Colman, P.M., et al., "Effects of amino acid sequence changes on antibody-antigen interactions," Research of Immunology, 145(1):33-36 (1994).
Daluiski et al., "Bone Morphogenetic Protein-3 is a Negative Regulator of Bone Density," Nature Genetics, 27:84-88 (2001).
Deal, C., "Potential New Drug Targets for Osteoporosis," Nature Clinical Practice, 5(1):20-27 (2009).
Deconinck, N., et al., "Pathophysiology of Duchenne Muscular Dystrophy: Current Hypotheses," Pediatr. Neurol., 36:1-7 (2007).
del Re et al., "Reconstitution and Analysis of Soluble Inhibin and Activin Receptor Complexes in a Cell-free System," The Journal of Biological Chemistry, 279(51):53126-53135 (2004).
Delogu, G., Et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).
DePaolo, L.V., et al., "Passive Immunoneutralization with a Monoclonal Antibody Reveals a Role for Endogenous Activin-B in Mediating FSH Hypersecretion during Estrus and Following Ovariectomy of Hypophysectomized, Pituitary-Grafted Rats," Endocrinology, 130(3):1741-1743 (1992).
Donaldson, et al., "Activin and inhibin binding to the soluble extracellular domain of activin receptor II", Endocrinology 140(4):1760-1766 (1999).
Donaldson, et al., "Molecular Cloning and Binding Properties of the Human Type II Activin Receptor", Biochemical and Biophysical Research Communications, 184(1):310-316 (1992).
Eijken, M., "The Activin A-Follistatin System: Potent Regulator of Human Extracellular Matrix Mineralization," The FASEB Journal, 21:2949-2960 (2007).
Fafioffe, et al.,"Activin and inhibin receptor gene expression in the ewe pituitary throughout the oestrous cycle," Journal of Endocrinology, 182:55-68 (2004).
Fajardo, R. J., et al., "Treatment with a Soluble Receptor for Activin Improves Bone Mass and Structure in the Axial and Appendicular Skeleton of Female Cynomolgus Macaques (*Macaca fascicularis*)," Bone, 46:64-71 (2010).
Frigon, N. L., et al, "Regulation of Globin Gene Expression in Human K562 Cells by Recombinant Activin A," Blood, 79(3):765-772 (1992).
Fuller et al., "Activin A Is an Essential Cofactor for Osteoclast Induction," Biochemical and Biophysical Research Communications, 268:2-7 (2000).
Funaba et al., "Expression and Localization of Activin Receptors During Endochondral Bone Development," European Journal of Endocrinology, 144:63-71 (2001).
Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).
Gamer et al., "BMP-3 is a Novel Inhibitor of Both Activin and BMP-4 Signaling in *Xenopus* Embryos," Developmental Biology, 285:156-168 (2005).
Ge, G., et al., "GDF11 Forms a Bone Morphogenetic Protein 1-Activated Latent Complex That Can Modulate Nerve Growth Factor-Induced Differentiation of PC12 Cells", Molecular and Cellular Biology, 25(14):5846-5858 (2005).
GenBank NM_001106, *Homo sapiens* activin A receptor, type IIB (ACVR2B), mRNA, http://www.ncbi.nlm.nih.gov/entrez/viewer.fcgi?db=nucleotide&val=116734707 (Downloaded on Jan. 29, 2007).
Gilbert, R., et al., "Prolonged dystrophin expression and functional correction of mdx mouse muscle following gene transfer with a helper-dependent (gutted) adenovirencoding murine dystrophin," Human Molecular Genetics, 12(11)1287-1299 (2003).
Gilchrist, A., et al., "Antagonists of the Receptor-G Protein Interface Block Gi-coupled Signal Transduction," Journal of Biological Chemistry, The American Society of Biological Chemists, Inc., 273(24):14912-14919 (1998).
Gonzalez-Cadavid, N. F., et al., "Organization of the human myostatin gene and expression in healthy men and HIV-infected men with muscle wasting," PNAS, 95:14938-14943 (1998).
Gray, et al., "Identification of a binding site on the type II activin receptor for activin and inhibin", Journal of Biological Chemistry, 275(5):3206-3212(2000).
Greenspan, N. S., et al., "Defining epitopes: It's not as easy as it seems," Nature Biotechnology, 17:936-937 (1999).
Greenwald, et al., "Characterization of the Extracellular Ligand-Binding Domain of the Type II Activin Receptor," Biochemistry, 37(47):16711-16718 (1998).
Greenwald, et al., "The BMP7/ActRII Extracellular Domain Complex Provides New Insights into the Cooperative Nature of Receptor Assembly," Molecular Cell, 11:605-617 (2003).

(56) References Cited

OTHER PUBLICATIONS

Greenwald, J., et al., "Three-finger toxin fold for the extracellular ligand-binding domain of the type II activin receptor serine kinase," Nature Structural Biology, 6(1):18-22 (1999).
Gregoriadis, G., et al., "Polysialic acids: potential in drug delivery," FEBS, 315(3):271-276 (1993).
Guo, et al., Protein Tolerance to Random Amino Acid Change. Proc. Natl. Acad. Sci. USA, 101(25):9205-9210 (Jun. 22, 2004). Epub Jun. 14, 2004.
Gupta, V. et al., "Transforming Growth Factor-b Superfamily: Evaluation as Breast Cancer Biomarkers and Preventive Agents," Current Cancer Drug Targets, 4:165-182 (2004).
Gura, T., "Cancer Models: Systems for Identifying New Drugs Are Often Faulty," Science, 278(5340):1041-1042 (1997).
Hamrick et al., "Bone Mineral Content and Density in the Humerus of Adult Myostatin-Deficient Mice," Calcified Tissue International, 71:63-68 (2002).
Hamrick, "Increased Bone Mineral Density in the Femora of GDF8 Knockout Mice," The Anatomical Record, Part A 272A:388-391 (2003).
Hamrick, M.W., et al., "Femoral Morphology and Cross-sectional Geometry of Adult Myostatin-deficient Mice," Bone, 27(3):343-349 (2000).
Harousseau et al., "Multiple Myeloma," American Society of Hematology, pp. 237-256 (2004).
Harrison, C.A., et al., "An Activin Mutant with Disrupted ALK4 Binding Blocks Signaling via Type II Receptors," The Journal of Biological Chemistry, 279(27):28036-28044 (2004).
Harrison, et al., "Antagonists of activin signaling: mechanisms and potential biological applications," Trends in Endocrinology and Metabolism, 16(2):73-78 (2005).
Hashimoto et al., "Functional Regulation of Osteoblastic Cells by the Interaction of Activin-A with Follistatin," The Journal of Biological Chemistry, 267(7):4999-5004 (1992).
Hemmati-Brivanlou, A., et al., "A truncated activin receptor inhibits mesoderm induction and formation of axial structures in *Xenopus* embryos," Nature, 359:609-614 (1992).
Herbert, W.J., et al., The Dictionary of Immunology, Academic Press, 3rd Edition, London, pp. 58-59 (1985).
Hilden, K., et al., "Expression of Type II Activin Receptor Genes During Differentiation of Human K562 Cells and cDNA Cloning of the Human Type IIB Activin Receptor," Blood, 83(8):2163-2170 (1994).
Hill, J.J., et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).
Hsieh, Matthew M, et al., "HIF-prolyl hydroxylase inhibition results in endogenous erythropoietin induction, erythrocytosis, and modest fetal hemoglobin expression in rhesus macaques," Blood, 110(6):2140-2147 (2007).
Ikenoue et al., "Inhibitory Effects of Activin-A on Osteoblast Differentiation During Cultures of Fetal Rat Calvarial Cells," Journal of Cellular Biochemistry, 75:206-214 (1999).
Kaiser, J., "First Pass at Cancer Genome Reveals Complex Landscape," Science, 313:1370 (2006).
Kaspar, B.K., et al., "Retrograde Viral Delivery of IGF-1 Prolongs Survival in a Mouse ALS Model," Science, 301:839-842 (2003).
Kim, et al., "Type IIa IgG-Fc Fusion Protein, Increases Hemoglobin and Hematocrit Levels in Postmenopausal Healthy Women," Blood, 112(11):1316 (2008).
Knight, "Roles of Inhibins, Activins, and Follistatin in the Female Reproductive System," Frontiers in Neuroendocrinology, 17:476-509 (1996).
Kosaki, R., et al., "Left-Right Axis Malformations Associated With Mutations in ACVR2B, the Gene for Human Activin Receptor Type IIB," American Journal of Medical Genetics, 82:70-76 (1999).
Koseki, et al., "Role of TCF-b Family in Osteoclastogenesis Induced by RANKL," Cellular Signaling, 14:31-36 (2002).
Krag, T.O.B., et al., "Heregulin ameliorates the dystrophic phenotype in mdx mice," PNAS, 101(38):13856-13860 (2004).
Krneta, J., et al., "Dissociation of Angiogenesis and Tumorigenesis in Follistatin- and Activin-Expressing Tumors," Cancer Research, 66(11):5686-5695 (2006).
Krystal et al., Transforming Growth Factor β1 Is an Inducer of Erythroid Differentiation. J. Exp. Med. vol. 180 pp. 851-860 (1994).
Kubanek, B., "Introduction: The Role of the Microenvironment and Cytokines on the Modulation of Erythropoiesis," Annals New York Academy of Sciences, pp. 257-258 (1994).
Kumar, T.R., et al., "Regulation of FSHβ and GnRH Receptor Gene Expression in Activin Receptor II Knockout Male Mice," Mol. Cell. Endocrinol., 212(1-2):19-27 (2003).
Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (Abstract) (1990).
Kuntz, "Structure-based strategies for drug design and discovery," Science, 257(5073):1078-1082 (1992).
Lazar, E., et al., "Transforming Growth Factor α: Mutation of Aspartic Acid 47 and Leucine 48 Results in Different Biological Activities," Molecular and Cellular Biology, 8(3):1247-1252 (1988).
Lebrun, J.J., et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS, 98(16):9306-9311 (2001).
Leto et al., "Activin A Circulating Levels in Patients with Bone Metastasis from Breast or Prostate Cancer," Clin Exp Metastasis, 23(2):117-122 (2006).
Li, Q., et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).
Lotinun, S., et al., "A Soluble Activin Receptor Type IIA Fusion Protein (ACE-011) Increases Bone Mass Via a Dual Anabolic-Antiresorptive Effect in Cynomolgus Monkeys," Bone, 46:1082-1088 (2010).
Lu, S., et al., "Simian Immunodeficiency Virus DNA Vaccine Trial in Macaques," Journal of Virology, 70(6):3978-3991 (1996).
Ludlow, H., et al., "Development of a new antibody to the human inhibin/activin βB subunit and its application to improved inhibin B ELISAs," J. Immunol. Methods, 329:102-111 (2008).
Maguer-Satta, V., et al, "A Novel Role for Fibronectin Type 1 Domain in the Regulation of Human Hematopoietic Cell Adhesiveness Through Binding to Follistatin Domains of FLRG and Follistatin," Experimental Cell Research, Academic Press, 312(4):434-442 (2006).
Maguer-Satta, V., et al, "Regulation of human erythropoiesis by activin A, BMP2, and BMP4, members of the TGGβ family," Experimental Cell Research, 282:110-120 (2003).
Maguer-Satta, V., et al., "FLRG, Member of the Follistatin Family, a New Player in Hematopoiesis," Molecular and Cellular Endocrinology, Elsevier Ireland Ltd., 225(1-2):109-118 (2004).
Mathews, L.S., et al., "Expression Cloning of an Activin Receptor, a Predicted Transmembrane Serine Kinase," Cell, 65(6):973-982 (1991).
Matzuk et al., "Cloning of the human activin receptor cDNA reveals high evolutionary conservation," Biochim Biophys Acta, 1130(1):105-108 (1992).
Matzuk et al., "Different phenotypes for mice deficient in either activins or activin receptor type II," Nature, 374:356-360 (1995).
McNally, E.M., "Powerful Genes—Myostatin Regulation of Human Muscle Mass," N. Engl. J. Med., 350(26):2642-2644 (2004).
McPherron, A.C., et al., "GDF-3 and GDF-9: Two New Members of the Transforming Growth Factor-B Superfamily Containing a Novel Pattern of Cysteines," Journal of Endocrinology, 268(5):3444-3449 (1993).

(56) References Cited

OTHER PUBLICATIONS

McPherron, A.C., et al., "Regulation of Skeletal Muscle Mass in Mice by a Bew TGF-b Superfamily Member," Nature, 387:83-90 (1997).
McPherson, S.J., et al., "Growth inhibitory response to activin A and B by human prostate tumour cell lines LNCaP and DU1465", Journal of Endocrinology, 154:535-545 (1997).
Menstruation: Absent Periods (Amenorrhea), Website downloaded on Jun. 14, 2010, <http://adam.about.com/reports/000101_2.htm?p=1> (11 pages).
Merck Manuals Online Medical Library (online). Anemia of Chronic Disease, Jun. 10, 2008. Downloaded from the internet on Jan. 5, 2010. <http://web.archive.org/web/20080610070226/http://www.merck.com/mmpe/sec11/ch130/ch130d.html> pp. 1-2.
Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.
Meriggiola et al., "Follistatin Decreases Activin-Stimulated FSH Secretion with No Effect on GnRH-Stimulated FSH Secretion in Prepubertal Male Monkeys," Endocrinology, 134(4):1967-1970 (1994).
Mickle, et al., "Genotype-Phenotype Relationships in Cystic Fibrosis," Med. Clin. North Am., 84(3):597-607 (2000).
Miller et al., Ligand binding to proteins: the binding landscape model. Protein Sci., 6(10):2166-79 (1997).
Miura, P., et al., "Utrophin upregulation for treating Duchenne or Becker muscular dystrophy: how close are we?," Trends in Molecular Medicine, 12(3):122-129 (2006).
Mosekilde, L., et al., "Emerging Anabolic Treatments in Osteoporosis," Current Drug Safety, 6:62-74 (2011).
Murase et al., "Possible Involvement of Protein Kinases and Smad2 Signaling Pathways on Osteoclast Differentiation Enhanced by Activin A," Journal of Cellular Physiology, 188:236-242 (2001).
Murata, T., et al., "Anti-activin A Antibody (IgY) Specifically Neutralizes Various Activin A Activities," Proceedings of the Society for Experimental Biology & Medicine, 211(1):100-107 (1996).
Nagamine et al., "Immunohistochemical Detection of Activin A, Follistatin, and Activin Receptors during Fracture Healing in the Rat," Journal of Orthopaedic Research, 16:314-321 (1998).
Nakamura, K., et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).
Ngo, J.T., et al., "Computational Complexity, Protein Structure Prediction, and the Levinthal Paradox," The Protein Folding Problem and Tertiary Structure Prediction, Merz et al., eds., Birkhauser, Boston, 433 and 492-495 (1994).
Ogawa et al., "Bovine Bone Activin Enhances Bone Morphogenetic Protein-Induced Ectopic Bone Formation," The Journal of Biological Chemistry, 267(20):14233-14237 (1992).
Oh, S.P., et al., "Activin type IIA and IIB receptors mediate Gdf11 signaling in axial vertebral patterning," Genes & Development, 16:2749-2754 (2002).
Oue et al., "Effect of Local Injection of Activin A on Bone Formation in Newborn Rats," Bone, 15(3):361-366 (1994).
Patel, K., et al., "The function of Myostatin and strategies of Myostatin blockade—new hope for therapies aimed at promoting growth of skeletal muscle," Neuromuscular Disorders, 15:117-126 (2005).
Pearsall, et al., "A Soluble Activin Receptor Type IIA (ACTRIIA) Acts as a Novel Bone Anabolic Agent," The Official Journal of the European Calcified Tissue Society, 34th Europena Symposium on Calcified Tissues, May (2007).
Pearsall, et al., "Treatment with a Soluble Activin Type II Receptor Reverses Bone Loss in Ovariectomized Mice," Journal of Bone and Mineral Research 2006 Abstracts, 21(1):s1-s530 (2006).
Pearsall, R.S., et al., "A soluble activin Type IIA receptor induces bone formation and improves skeletal integrity", PNAS, 105(9):7082-7087 (2008).
Perrien, D. S., et al., "Inhibin A Is an Endocrine Stimulator of Bone Mass and Strength," Endocrinology, 148(4):1646-1665 (2007).
Phillips, A.J., "The challenge of gene therapy and DNA delivery," J. Pharm. Pharmacology, 53:1169-1174 (2001).
Pirollo, K.F., et al., "Targeted Delivery of Small Interfering RNA: Approaching Effective Cancer Therapies," Cancer Res., 68(5):1247-1250 (2008).
Qi, et al., "Blockade of type β transforming growth factor signaling prevents liver fibrosis and dysfunction in the rat," PNAS, 96:2345-2349 (1999).
Raju, T.S., "Glycosylation in the Fc domain of IgG increases resistance to proteolytic cleavage by papain," Biochemical and Biophysical Research Communications, 341:797-803 (2006).
Rebbapragada, et al., "Myostatin Signals Through a Transforming Growth Fact b-Like Signaling Pathway to Block Adipogenesis," Molecular and Cellular Biology, 23(20):7230-7242 (2003).
"Recombinant Human Activin RIIB/Fc Chimera," R&D Systems 339-RB/CF (Aug. 27, 2003).
"Recombinant Human Activin RIIA/Fc Chimera," R&D Systems 340-R2 (Aug. 27, 2003).
Reis, F.M., et al., "Activin, Inhibin and the Human Breast," Molecular and Cellular Edocrinology, 225:77-82 (2004).
Risbridger, G.P, et al., "Activins and Inhibins in Endocrine and Other Tumors," Endocrine Reviews, 22(6):836-858 (2001).
Robinson, G.W., et al., "Inhibins and Activins Regulate Mammary Epithelial Cell Differentiation Through Mesenchymal-epithelial Interactions," Development, 124:2701-2708 (1997).
Rodriquez, J.E.S., et al., "Enhanced Osteoclastogenesis Causes Osteopenia in Twisted Gastrulation-Deficient Mice Through Increased BMP Signaling," J. Bone Miner. Res., 24:1917-1926 (2009).
Rosenzweig et al., "Cloning and characterization of a human type II receptor for bone morphogenetic proteins," PNAS, 92:7632-7636 (1995).
Ruckle et al., "Single-Dose, Randomized, Double-Blind, Placebo-Controlled Study of ACE-011 (ACTRIIA-IgG1) in Postmenopausal Women," Journal of Bone and Mineral Research, vol. 24(4), pp. 744-752 (2009).
Ruzek et al. Minimal Effects on Immune Parameters Following Chronic Anti-TGF-β Monoclonal Antibody Administration to Normal Mice. Immunopharmacology and Immunotoxicology, 25(2):235-257 (2003).
Sakai et al., "Activin Enhances Osteoclast-Like Cell Formation in Vitro," Biochemical and Biophysical Research Communications, 195(1):39-46 (1993).
Sakai et al., "Activin Increases Bone Mass and Mechanical Strength of Lumbar Vertebrae in Aged Ovariectomized Rats," Bone, 27(1):91-96 (2000).
Sakai et al., "Activin release from bone coupled to bone resorption in organ culture of neonatal mouse calvaria," Bone, 26(3):235-240 (2000).
Sakai et al., "Involvement of Activin in the Regulation of Bone Metabolism," Molecular and Cellular Endocrinology, 180:183-188 (2001).
Sakai et al., "Local Administration of Activin Promotes Fracture Healing in the Rat Fibula Fracture Model," Bone, 25(2):191-196 (1999).
Sakai et al., The Measurement of Activin/EDF in Mouse Serum: Evidence for Extragonadal Production. Biochecmical and Biophysical Research Communications, 188(2):921-926 (1992).
Sakai, et al., "Osteogenic Activity of Activin in Young Normal Rats and Young Adult and Aged Rats after Ovarlectomy," Bone 23:(Suppl.) 467 (1998).
Sako, D., et al., "Characterizationof the Ligand Binding Functionality of the Extracellular Domain of Activin Receptor Type IIB," The Journal of Biological Chemistry, 285(27):21037-21048 (2010).
Satoh, et al., "Hemodynamic changes by recombinant erythropoietin therapy in hemodialyzed patients," Hypertension, 15(3):262-266 (1990).
Schmelzer, C.H., et al., "Purification and Characterization of Recombinant Human Activin B," Biochimica et Biophysica Acta, 1039(2):135-141 (1990).

(56) References Cited

OTHER PUBLICATIONS

Schuelke, M., et al., "Myostatin Mutation Associated with Gross Muscle Hypertrophy in a Child," New England Journal of Medicine, 350(26):2682-2688 (2004).
Shao, L., et al., "Effect of Activin A on Globin Gene Expression in Purified Human Erythroid Progenitors," Blood, 79(3):773-781 (1992).
Shav-Tal, Y., et al., "The Role of Activin A in Regulation of Hemopoiesis," Stem Cells, 20:493-500 (2002).
Shi et al., "Energy Balance, Myostatin, and GILZ: Factors Regulating Adipocyte Differentiation in Belly and Bone," PPAR Research, pp. 1-12 (2007).
Shiozaki, M., et al, "Activin A: A Commitment Factor in Erythroid Differentiation," Biochemical and Biophysical Research Communications, 242:631-635 (1998).
Shiozaki, M., et al, "Evidence for the participation of endogenous activin A/erythroid differentiation factor in the regulation of erythropoiesis," Proc. Natl. Acad. Sci. USA, 89:1553-1556 (1992).
Shiozaki, M., et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).
Shuto et al., "Osteoblasts Express Types I and II Activin Receptors During Early Intramembranous and Endochondral Bone Formation," Journal of Bone Mineral Research, 12(3):403-411 (1997).
Smith, L. et al., "The analysis of doxorubicin resistance in human breast cancer cells using antibody microarrays," Mol. Cancer Therapy, vol. 5: 2115-2120 (2006).
Smith, L. et al., The Status, Quality, and Expansion of the NIH Full-Length cDNA Project: The Mammalian Gene Collection (MGC), Genome Res., vol. 14(10b),: 2127-2127 (2004).
Song, J., et al., "The Type II Activin Receptors Are Essential for Egg Cylinder Growth, Gastrulation, and Rostral Head Development in Mice," Development Biology, 213:157-169 (1999).
Springer, et al., "Seventh European Congress on Clinical and Economic Aspects of Osteoporosis and Osteoarthritis," Osteoporosis International, 18(1):S29-S75 (2007).
Sun, et al., "FSH Directly Regulates Bone Mass," Cell, 125:247-260 (2006).
Tanno, T. and Miller, J.L., "Iron Loading and Overloading due to Ineffective Erythropoiesis," Advances in Hematology, Article ID 358283, Chapter 2 (Abstract) (2010).
Thompson, et al., "Structures of an ActRIIB: activin A complex reveal a novel binding mode for TGF-beta ligand: receptor interactions", EMBO 22(7):1555-1566 (2003).
Thompson, T.B., et al., "Beta A versus beta B: is it merely a matter of express?," Molecular and Cellular Endocrinology, 225:9-17 (2004).
Tinsley, J., et al., "Expression of full-length utrophin prevents muscular dystrophy in *mdx* mice," Nature Medicine, 4(12):1441-1444 (1998).
Tisdale, M.J., "Cachexia in Cancer Patients," Nat. Rev. Cancer, 2:862-871 (2002).
Tokuriki, N., et al., "Stability effects of mutations and protein evolvability," Current Opinion in Structural Biology, 19:596-604 (2009).
Trivedi, R., et al., "Investigational Anabolic Therapies for Osteoporosis," Expert Opin. Investig. Drugs, 19(8):995-1005 (2010).
Tsuchida, et al., "Activin isoforms signal through type I receptor serine/threonine kinase ALK7," Molecular and Cellular Endocrinology, 220:59-65 (2004).
Tu, P., et al., "Genetic Disruption of Myostatin Reduces the Development of Proatherogenic Dyslipidemia and Atherogenic Lesions in Ldlr Null Mice," Diabetes, 58:1739-1748 (2009).
Type 2 Diabetes, PubMed Health, Diseases and Conditions, U.S. National Library of Medicine, Bethesda, MD (online), Jun. 28, 2011 [retrieved on Jun. 6, 2012). Retrieved from the Internet:<URL:http://www.ncbi.nlm.nih.gov/pubmedhealth/PMH0001356/>.
Ukkola, et al., "Adiponectin: A Link Between Excess Adiposity and Associated Comorbidities?", Journal of Molecular Medicine, 80(11):696-702 (2002).
Utzschneider, et al., The Role of Insulin Resistance in Nonalcoholoc Fatty Liver Disease, J. Clin. Endocrinol. Metab., 91(12):4753-4761 (Dec. 2006). Epub Sep. 12, 2006.
Vallet, S., et al., "Activin A promotes multiple myeloma-induced osteolysis and is a promising target for myeloma bone disease," PNAS, 107(11):5124-5129 (2010).
Vidal, L., et al., "Making sense of antisense," European Journal of Cancer, 41:2812-2818 (2005).
Wagner, K.R., et al., "A Phase I/II trial of MYO-029 in Adult Subjects with Muscular Dystrophy," Ann. Neurol., 63:561-571 (2008).
Wagner, K.R., et al., "Loss of Myostatin Attenuates Severity of Muscular Dystrophy in *mdx* Mice," Ann. Neurol., 52:832-836 (2002).
Wagner, K.R., et al., "Muscle regeneration in the prolonged absence of myostatin," PNAS, 102(7):2519-2524 (2005).
Walsh, F. S, et al., "Myostatin: a modulator of skeletal-muscle stems cells," Biochemical Society Transactions, 33(Pt.6):1513-1517 (2005).
Wang, et al., A single amino acid determines lysophospholipid specificity of the S1P1 (EDG1) and LPA1 (EDG2) phospholipid growth factor receptors. JBC 276:49213-49220 (2001).
Wang, W., et al., "GDF-3 is an adipogenic cytokine under high fat dietary condition," Biochemical and Biophysical Research Comm., 321(4):1024-1031 (2004).
Weber, et al., A slient H-bond can by mutationally activated for high-affinity interaction of BMP-2 and activin type IIB receptor, BMC Structural Biology, 7(6):1-20 (2007).
Wells, J.A., "Additivity of Mutational Effects in Proteins," Biochemistry, 29(37):8509-8517 (1990).
Welt, et al., "Activin: an endocrine or panacrine agent?," European Journal of Endocrinology 139:469-471 (1998).
Wiater, et al., "Inhibin is an Antagonist of Bone Morphogenetic Protein Signaling," The Journal of Biological Chemistry, 278(10):7934-7941 (2003).
Wolfman, N. M., et al., "Activation of latent myostatin by the BMP-1/tolloid family of metalloproteinases," PNAS, 100(26):15842-15846 (2003).
Yamato et al., "Induction of apoptosis in Myeloma Cells with Activin A," Japanese Journal of Clinical Hematology; 37th Annual Meeting, Symposium 3, Apoptosis in Blood Disorders, 37:7, pp. 564-567) (2012). (translated).
Yokota, T., et al., "Isolation and characterization of a mouse cDNA clone that expresses mast-cell growth-factor activity in monkey cells," Proc. Natl. Acad. Sci. USA, 81:1070-1074 (1984).
Yu et al., "Specific roles of activin/inhibin in human erythropoiesis in vitro." Annals New York Academy of Sciences, 20(10):1243-1246 (1991).
Yu, J., et al., "Importance of FSH-releasing protein and inhibin in erythrodifferentiation," Nature, 330:765-767 (1987).
Zatz et al., "Serum creatine-kinase (CK) and pyruvate-kinase (PK) activities in Duchenne (DMD) as compared with Becker (BMD) muscular dystrophy," Journal of the Neurological Sciences, vol. 102: 190-196 (1991).
Zhao, B., et al., "Transgenic expression of myostatin propeptide prevents diet-induced obesity and insulin resistance," Biochemical and Biophysical Research Communications, 337:248-255 (2005).
Chavez-Tapia, Norberto-C et al., "Insulin sensitizers in treatment of nonalcoholic fatty liver disease: Systematic review," World Journal of Gastroenterology, vol. 12(48): 7826-7831 (2006).
Koncarevic et al., "A Soluble Activin Receptor Type IIB Prevents the Effects of Angdrogen Deprivation on Body Composition and Bone Health," Endocrinology, vol. 151(9); 4289-4300 (2010).
Abbiotec: ACTR-IIA Antibody: Catalog No. 251303 (http://www.abbiotec.com) Jun. 3, 2010.
Acta Cryst.,"The CCP4 suite: programs for protein crystallography: Collaborative Computational Project, No. 4," D50: 760-763 (1994).
Anonymous "Learning about Thalassemia" <http://www.genome.gov/10001221> Accessed on Internet Jul. 9, 2013.
Anti-ActRIIA Antibodies: Commercial Monoclonal Antibodies Against Human ActRIIA (2010).
Antibodies for ACVR2A: http://www.genecards.org/cgi-bin/carddisp.pl?gene=Acvr2a (Jun. 8, 2010).

(56) References Cited

OTHER PUBLICATIONS

Casset et al., "A Peptide mimetic of an anti-CD4 monoclonal antibody by rational design," Biochemical and Biophysical Research Communications, vol. 307:198-205 (2003).
CDR Definitions from Handbook of Therapeutic Antibodies, (2007).
Chardès et al., "Efficient amplification and direct sequencing of mouse variable regions from any immunoglobulin gene family," FEBS Lett. vol. 452(3): 386-394 (1999).
Chen et al., "Selection and Analysis of an Optimized Anti-VEGF Antibody: Crystal Structure of an Affinity-matured Fab in Complex with Antigen," J. Mol. Biol., vol. 293: 865-881 (1999).
Donald et al., "SDR: a database of predicted specificity-determining residues in proteins," Nucleic Acids Research, vol. 37: D191-D194 (2009).
Elliot et al., "Enhancement of therapeutic protein in vivo activities through glycoengineering," Nature Biotechnology, vol. 21: 414-421 (2003).
Fan, et al., "Preclinical evaluation of Hematide, a novel erythropoiesis stimulating agent, for the treatment of anemia," Experimental Hematology 34, pp. 1303-1311 (2006).
Foucar, K., Myelodysplastic/Myeloproliferative Neoplasms, Am J Clin Pathol, vol. 132: 281-289 (2009).
Haidar et al., "Paraspinal extramedullary hematopoiesis in patients with thalassemia intermedia," Eur Spine J., vol. 19: 871-878 (2010).
Holm et al., "Functional mapping and single chain construction of the anti-cytokeratin 8 monoclonal antibody TS1," ScienceDirect; Molecular Immunology, vol. 44(6): 1075-1084 (2007).
"The Illustrated Guide to Bone Marrow Diagnosis Second Edition," Ed. By G. Kumar. (Originally published 2003).
International Search Report, PCT/US2010/000080, dated Mar. 29, 2010.
Ito et al., "Presence of activin signal transduction in normal ovarian cells and epithelial ovarian carcinoma," British Journal of Cancer, vol. 82(8): 1415-1420 (2000).
Kos et al., "Activin type II receptors in embryonic dorsal root ganglion neurons of the chicken," J. Neurobiol., vol. 47(2): 93-108 (2001).
Liu et al., "Characterization of isoforms of activin receptor-interacting protein 2 that augment activin signaling," Journal of Endocrinology, vol. 189: 409-421 (2006).
MacCallum et al., "Antibody-antigen Interactions: Contact Analysis and Binding site Topography," J. Mol. Biol, vol. 262: 732-745 (1996).
Paul, William E., Fundamental Immunology, 3rd edition, Raven Press, New York, 1003: 292-295 (1999).
Pearsall et al., An investigative pharmacology study of a GDF-8 (myostatin) inhibitor, ACE-031, in the common Marmoset (*Callithrix jacchus*), Database Biosis, Biosciences Information Service, Accession No. PREV201200750016; Faseb Journal, vol. 22, Experimental Biology Annual Meeting, San Diego, CA Apr. 5-9, 2008 (Abstract).
Shoji et al., "Identification and Characterization of a PDZ Protein That Interacts with Activin Type II Receptors," The Journal of Biological Chemistry, vol. 275(8): 5485-5492 (2000).
Suragani et al., "4236 ACE-536, a Modified Type II Activin Receptor Increases Red Blood Cells in Vivo by Promoting Maturation of Late Stage Erythroblasts," 52nd ASH Annual Meeting and Expositions, Orange County Convention Center, Orlando, FL Dec. 4-7, 2010. (abstract).
Swanson et al., "Use of Biosensors to Monitor the Immune Response," Biologics, vol. 109: 71-78 (2000).
Swanson, S. J., "New Technologies for the Detection of Antibodies to Therapeutic Proteins," Immunogenicity of Therapeutics Biological Products, vol. 112: 127-133 (2003).
Thorpe and Swanson, "Current methods for Detecting Antibodies against Erythropoietin and Other Recombinant Proteins," Clinical and Diagnostic Laboratory Immunology, vol. 12(1): 28-39 (2005).
Tseng, Yu-Hua et al., "New role of bone morphogenetic protein 7 in brown adipogenesis and energy expenditure," Nature: International Weekly Journal of Science (and Supplementary Information), vol. 454(7207): 1000-1004 (2008).
US Biological, Activin Receptor Type IIA (RIIA) A0856-05E; www.usbio.net/technicalsheet.php?item=A0856-05E dated Jun. 8, 2010.
Vajdos et al., "Comprehensive Functional Maps of the Antigen-binding Site of an Anti-ErbB2 Antibody Obtained with Shotgun Scanning mutagenesis," J. Mol. Biol., vol. 320(2): 415-428 (2002).
Ward, R., "An update on disordered iron metabolism and iron overload," Hematology, vol. 15(5): 311-317 (2010).
Wong et al., "Validation parameters for a novel biosensor assay which simultaneously measures serum concentrations of a humanized monoclonal antibody and detects induced antibodies," Journal of Immunological Methods, vol. 209: 1-15 (1997).
Zhang et al., Effects of Activin A on the Activities of the Mouse Peritoneal Macrophages, Cellular & Molecular Immunology, vol. 2(1): 63-67 ( 2005).

FIGURE 1. Human ActRIIB soluble (extracellular) polypeptide sequence designated as SEQ ID NO: 1 (116 aa)

SGRGEAETRECIYYNANWELERTNQSGLERCEGEQDKRLHCYASWRNSSGTIELVKKGC

WLDDFNCYDRQECVATEENPQVYFCCCEGNFCNERFTHLPEAGGPEVTYEPPPTAPT

FIGURE 1

FIGURE 2. Human ActRIIB precursor sequence designated as SEQ ID NO: 2 (NM_001106, 512 aa)

MTAPWVALALLWGSLWPGSGRGEAETRECIYYNANWELERTNQSGLERCEGEQDKRLHC

YASWRNSSGTIELVKKGCWLDDFNCYDRQECVATEENPQVYFCCCEGNFCNERFTHLPE

AGGPEVTYEPPPTAPTLLTVLAYSLLPIGGLSLIVLLAFWMYRHRKPPYGHVDIHEDPG

PPPPSPLVGLKPLQLLEIKARGRFGCVWKAQLMNDFVAVKIFPLQDKQSWQSEREIFST

PGMKHENLLQFIAAEKRGSNLEVELWLITAFHDKGSLTDYLKGNIITWNELCHVAETMS

RGLSYLHEDVPWCRGEGHKPSIAHRDFKSKNVLLKSDLTAVLADFGLAVRFEPGKPPGD

THGQVGTRRYMAPEVLEGAINFQRDAFLRIDMYAMGLVLWELVSRCKAADGPVDEYMLP

FEEEIGQHPSLEELQEVVVHKKMRPTIKDHWLKHPGLAQLCVTIEECWDHDAEARLSAG

CVEERVSLIRRSVNGTTSDCLVSLVTSVTNVDLPPKESSI

FIGURE 2

FIGURE 3. Nucleic acid sequence encoding a human ActRIIB soluble (extracellular) polypeptide, designated as SEQ ID NO: 3 (348 bp)

tctgggcgtggggaggctgagacacgggagtgcatctactacaacgccaactgggagctggagcgcaccaa
ccagagcggcctggagcgctgcgaaggcgagcaggacaagcggctgcactgctacgcctcctggcgcaaca
gctctggcaccatcgagctcgtgaagaagggctgctggctagatgacttcaactgctacgataggcaggag
tgtgtggccactgaggagaacccccaggtgtacttctgctgctgtgaaggcaacttctgcaacgagcgctt
cactcatttgccagaggctgggggcccggaagtcacgtacgagccacccccgacagcccccacc

FIGURE 3

FIGURE 4. Nucleic acid sequence encoding a human ActRIIB precursor protein, designated as SEQ ID NO: 4 (nucleotides 5-1543 of NM_001106, 1539 bp)

atgacggcgccctgggtggccctcgccctcctctggggatcgctgtggcccggctctgggcgtggggaggc
tgagacacgggagtgcatctactacaacgccaactgggagctggagcgcaccaaccagagcggcctggagc
gctgcgaaggcgagcaggacaagcggctgcactgctacgcctcctggcgcaacagctctggcaccatcgag
ctcgtgaagaagggctgctggctagatgacttcaactgctacgataggcaggagtgtgtggccactgagga
gaacccccaggtgtacttctgctgctgtgaaggcaacttctgcaacgagcgcttcactcatttgccagagg
ctgggggcccggaagtcacgtacgagccacccccgacagcccccaccctgctcacggtgctggcctactca
ctgctgcccatcgggggcctttccctcatcgtcctgctggcctttttggatgtaccggcatcgcaagcccc
ctacggtcatgtggacatccatgaggaccctgggcctccaccaccatcccctctggtgggcctgaagccac
tgcagctgctggagatcaaggctcgggggcgctttggctgtgtctggaaggcccagctcatgaatgacttt
gtagctgtcaagatcttcccactccaggacaagcagtcgtggcagagtgaacgggagatcttcagcacacc
tggcatgaagcacgagaacctgctacagttcattgctgccgagaagcgaggctccaacctcgaagtagagc
tgtggctcatcacggccttccatgacaagggctccctcacggattacctcaaggggaacatcatcacatgg
aacgaactgtgtcatgtagcagagacgatgtcacgaggcctctcatacctgcatgaggatgtgccctggtg
ccgtggcgagggccacaagccgtctattgcccacagggactttaaaagtaagaatgtattgctgaagagcg
acctcacagccgtgctggctgactttggcttggctgttcgatttgagccagggaaacctccaggggacacc
cacggacaggtaggcacgagacggtacatggctcctgaggtgctcgagggagccatcaacttccagagaga
tgccttcctgcgcattgacatgtatgccatggggttggtgctgtgggagcttgtgtctcgctgcaaggctg
cagacggacccgtggatgagtacatgctgccctttgaggaagagattggccagcacccttcgttggaggag
ctgcaggaggtggtggtgcacaagaagatgaggcccaccattaaagatcactggttgaaacacccgggcct
ggcccagctttgtgtgaccatcgaggagtgctgggaccatgatgcagaggctcgcttgtccgcgggctgtg
tggaggagcgggtgtccctgattcggaggtcggtcaacggcactacctcggactgtctcgtttccctggtg
acctctgtcaccaatgtggacctgccccctaaagagtcaagcatctaa

FIGURE 4

FIGURE 5. Alignment of human ActRIIA (designated as SEQ ID NO: 14) and ActRIIB

```
ActRIIa     ILGRSETQEC LFFNANWEKD RTNQTGVEPC YGDKDKRRHC FATWKNISGS
ActRIIb     GRGEAETREC IYYNANWELE RTNQSGLERC EGEQDKRLHC YASWRNSSGT

            IEIVKQGCWL DDINCYDRTD CVEKKDSPEV YFCCCEGNMC NEKFSYFPEM
            IELVKKGCWL DDFNCYDRQE CVATEENPQV YFCCCEGNFC NERFTHLPEA

            EVTQPTSNPV TPKPPT
            GGPEVTYEPP PTAPT
```

FIGURE 5

FIGURE 6. Multiple sequence alignment of vertebrate ActRIIB proteins and human ActRIIA, designated as SEQ ID NO: 15-22
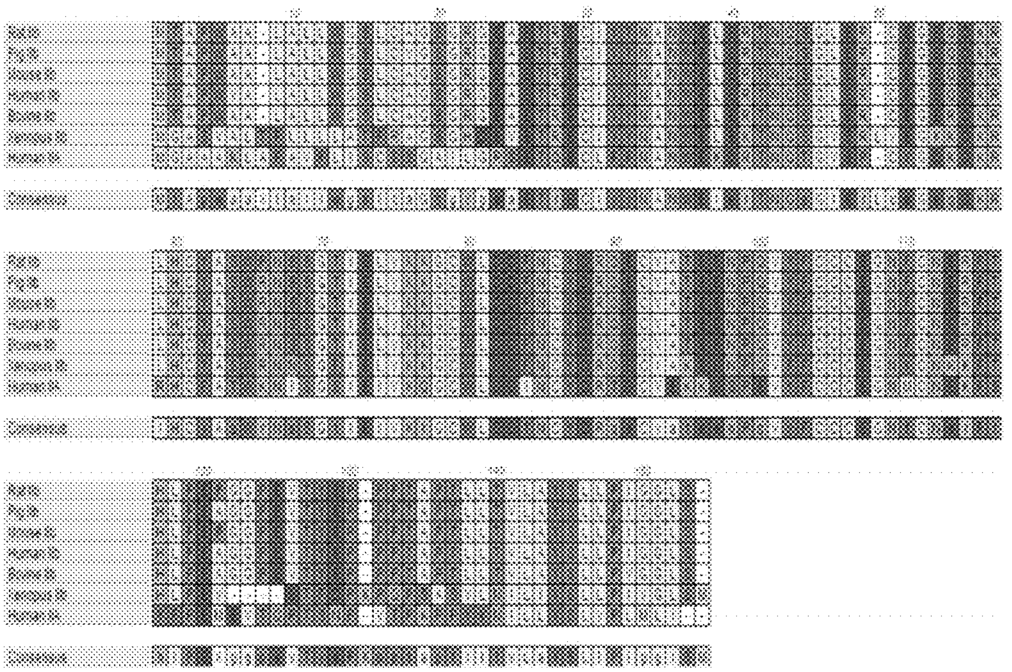

FIGURE 7. Amino acid sequence of ActRIIB(25-131)-hFc

```
  1  MDAMKRGLCC VLLLCGAVFV SPGAAETREC IYYNANWELE RTNQSGLERC
 51  EGEQDKRLHC YASWRNSSGT IELVKKGCWL DDFNCYDRQE CVATEENPQV
101  YFCCCEGNFC NERFTHLPEA GGPEVTYEPP PTGGGTHTCP PCPAPELLGG
151  PSVFLFPPKP KDTLMISRTP EVTCVVVDVS HEDPEVKFNW YVDGVEVHNA
201  KTKPREEQYN STYRVVSVLT VLHQDWLNGK EYKCKVSNKA LPAPIEKTIS
251  KAKGQPREPQ VYTLPPSREE MTKNQVSLTC LVKGFYPSDI AVEWESNGQP
301  ENNYKTTPPV LDSDGSFFLY SKLTVDKSRW QQGNVFSCSV MHEALHNHYT
351  QKSLSLSPGK  (SEQ ID NO: 24)
```

FIGURE 7

FIGURE 8. A nucleotide sequence encoding ActRIIB(25-131)-hFc

```
  1   ATGGATGCAA TGAAGAGAGG GCTCTGCTGT GTGCTGCTGC TGTGTGGAGC
      TACCTACGTT ACTTCTCTCC CGAGACGACA CACGACGACG ACACACCTCG

                             A  E  T   R  E  C   I  Y  Y
 51   AGTCTTCGTT TCGCCCGGCG CCGCTGAGAC ACGGGAGTGC ATCTACTACA
      TCAGAAGCAA AGCGGGCCGC GGCGACTCTG TGCCCTCACG TAGATGATGT

      N  A  N  W   E  L  E   R  T  N   Q  S  G  L   E  R  C
101   ACGCCAACTG GGAGCTGGAG CGCACCAACC AGAGCGGCCT GGAGCGCTGC
      TGCGGTTGAC CCTCGACCTC GCGTGGTTGG TCTCGCCGGA CCTCGCGACG

       E  G  E   Q  D  K  R   L  H  C   Y  A  S   W  R  N  S
151   GAAGGCGAGC AGGACAAGCG GCTGCACTGC TACGCCTCCT GGCGCAACAG
      CTTCCGCTCG TCCTGTTCGC CGACGTGACG ATGCGGAGGA CCGCGTTGTC

       S  G  T   I  E  L   V  K  K  G   C  W  L   D  D  F
201   CTCTGGCACC ATCGAGCTCG TGAAGAAGGG CTGCTGGCTA GATGACTTCA
      GAGACCGTGG TAGCTCGAGC ACTTCTTCCC GACGACCGAT CTACTGAAGT

      N  C  Y  D   R  Q  E   C  V  A   T  E  E  N   P  Q  V
251   ACTGCTACGA TAGGCAGGAG TGTGTGGCCA CTGAGGAGAA CCCCCAGGTG
      TGACGATGCT ATCCGTCCTC ACACACCGGT GACTCCTCTT GGGGGTCCAC

       Y  F  C   C  C  E  G   N  F  C   N  E  R   F  T  H  L
301   TACTTCTGCT GCTGTGAAGG CAACTTCTGC AACGAGCGCT TCACTCATTT
      ATGAAGACGA CGACACTTCC GTTGAAGACG TTGCTCGCGA AGTGAGTAAA

       P  E  A   G  G  P   E  V  T  Y   E  P  P   P  T
351   GCCAGAGGCT GGGGGCCCGG AAGTCACGTA CGAGCCACCC CCGACAGGTG
      CGGTCTCCGA CCCCCGGGCC TTCAGTGCAT GCTCGGTGGG GGCTGTCCAC

401   GTGGAACTCA CACATGCCCA CCGTGCCCAG CACCTGAACT CCTGGGGGGA
      CACCTTGAGT GTGTACGGGT GGCACGGGTC GTGGACTTGA GGACCCCCCT

451   CCGTCAGTCT TCCTCTTCCC CCCAAAACCC AAGGACACCC TCATGATCTC
      GGCAGTCAGA AGGAGAAGGG GGGTTTTGGG TTCCTGTGGG AGTACTAGAG

501   CCGGACCCCT GAGGTCACAT GCGTGGTGGT GGACGTGAGC CACGAAGACC
      GGCCTGGGGA CTCCAGTGTA CGCACCACCA CCTGCACTCG GTGCTTCTGG

551   CTGAGGTCAA GTTCAACTGG TACGTGGACG GCGTGGAGGT GCATAATGCC
      GACTCCAGTT CAAGTTGACC ATGCACCTGC CGCACCTCCA CGTATTACGG

601   AAGACAAAGC CGCGGGAGGA GCAGTACAAC AGCACGTACC GTGTGGTCAG
      TTCTGTTTCG GCGCCCTCCT CGTCATGTTG TCGTGCATGG CACACCAGTC

651   CGTCCTCACC GTCCTGCACC AGGACTGGCT GAATGGCAAG GAGTACAAGT
      GCAGGAGTGG CAGGACGTGG TCCTGACCGA CTTACCGTTC CTCATGTTCA

701   GCAAGGTCTC CAACAAAGCC CTCCCAGCCC CCATCGAGAA AACCATCTCC
      CGTTCCAGAG GTTGTTTCGG GAGGGTCGGG GGTAGCTCTT TTGGTAGAGG
```

```
751   AAAGCCAAAG GGCAGCCCCG AGAACCACAG GTGTACACCC TGCCCCCATC
      TTTCGGTTTC CCGTCGGGGC TCTTGGTGTC CACATGTGGG ACGGGGGTAG

801   CCGGGAGGAG ATGACCAAGA ACCAGGTCAG CCTGACCTGC CTGGTCAAAG
      GGCCCTCCTC TACTGGTTCT TGGTCCAGTC GGACTGGACG GACCAGTTTC

851   GCTTCTATCC CAGCGACATC GCCGTGGAGT GGGAGAGCAA TGGGCAGCCG
      CGAAGATAGG GTCGCTGTAG CGGCACCTCA CCCTCTCGTT ACCCGTCGGC

901   GAGAACAACT ACAAGACCAC GCCTCCCGTG CTGGACTCCG ACGGCTCCTT
      CTCTTGTTGA TGTTCTGGTG CGGAGGGCAC GACCTGAGGC TGCCGAGGAA

951   CTTCCTCTAT AGCAAGCTCA CCGTGGACAA GAGCAGGTGG CAGCAGGGGA
      GAAGGAGATA TCGTTCGAGT GGCACCTGTT CTCGTCCACC GTCGTCCCCT

1001  ACGTCTTCTC ATGCTCCGTG ATGCATGAGG CTCTGCACAA CCACTACACG
      TGCAGAAGAG TACGAGGCAC TACGTACTCC GAGACGTGTT GGTGATGTGC

1051  CAGAAGAGCC TCTCCCTGTC CCCGGGTAAA TGA   (SEQ ID NO: 25)
      GTCTTCTCGG AGAGGGACAG GGGCCCATTT ACT
```

FIGURE 8 (continued)

FIGURE 9. Body weight vs. time in mice as a function of ORX and ActRIIB-mFc treatment FIGURE 10. Lean body mass vs. time in mice as a function of ORX and ActRIIB-mFc treatment FIGURE 11. Muscle mass in mice as a function of ORX and ActRIIB-mFc treatment for 71 days

FIGURE 12. Whole-body bone area vs. time for mice as a function of ORX and ActRIIB-mFc treatment

FIGURE 13. Whole-body bone mineral content vs. time for mice as a function of ORX and ActRIIB-mFc treatment

FIGURE 14. Whole-body bone mineral density vs. time for mice as a function of ORX and ActRIIB-mFc treatment

FIGURE 15. Bone volume fraction in murine tibia as a function of ORX and ActRIIB-mFc treatment for 71 days FIGURE 16. Trabecular number in murine tibia as a function of ORX and ActRIIB-mFc treatment for 71 days FIGURE 17. Trabecular thickness in murine tibia as a function of ORX and ActRIIB-mFc treatment for 71 days FIGURE 18. Trabecular separation in murine tibia as a function of ORX and ActRIIB-mFc treatment for 71 days FIGURE 19. Tibial morphology in mice as a function of ORX and ActRIIB-mFc treatment for 71 days FIGURE 20. Fat tissue mass vs. time in mice as a function of ORX and ActRIIB-mFc treatment

FIGURE 21. Adipocyte histology in ORX mice treated with vehicle or ActRIIB-mFc for 71 days

FIGURE 22. Serum adiponectin concentrations in mice as a function of ORX and ActRIIB-mFc treatment for 71 days FIGURE 23. Serum leptin concentrations in mice as a function of ORX and ActRIIB-mFc treatment for 71 days

FIGURE 24. Effect of ActRIIB(20-134)-hFc or ActRIIB(25-131)-hFc on serum adiponectin concentrations in mice fed a high-fat diet

FIGURE 25. Effect of ActRIIB(25-131)-hFc on adiponectin mRNA levels in white adipose tissue in mice fed a high-fat diet

METHODS FOR INCREASING ADIPONECTIN

CROSS-REFERENCES TO RELATED APPLICATIONS

This application is a continuation of U.S. application Ser. No. 12/657,146, filed Jan. 13, 2010, which claims the benefit of U.S. Provisional Application No. 61/204,946, filed Jan. 13, 2009. The specifications of each of the foregoing applications are incorporated herein by reference in their entirety.

SEQUENCE LISTING

The instant application contains a Sequence Listing which has been submitted via EFS-Web and is hereby incorporated by reference in its entirety. Said ASCII copy, created on Feb. 10, 2012, is named PHPH-044-102seq.txt, and is 47,969 bytes in size.

BACKGROUND OF THE INVENTION

Once thought to be merely an inert storage depot for excess energy, adipose tissue is now recognized as an active endocrine and paracrine organ secreting multiple mediators, known as adipokines, that participate in diverse metabolic processes. The polypeptide adipokine adiponectin is the most abundant known factor secreted by adipocytes and accounts for approximately 0.01% of plasma protein. Whereas levels of other adipokines increase with fat mass, adiponectin levels vary inversely with fat mass/obesity. Decreased adiponectin levels are also observed in type 2 diabetes and cardiovascular disease. The strong correlation between low levels of circulating adiponectin, or hypoadiponectinemia, and risk factors for these major diseases may derive partly from adiponectin's anti-inflammatory properties, which contrast with the proinflammatory character of other adipokines (Szmitko et al., 2007, Am J Physiol Heart Circ Physiol 292:H1655-H1663). Thus, adiponectin appears to function as the protective adipokine, counterbalancing the potentially detrimental actions of these other adipokines.

Considerable evidence has emerged linking hypoadiponectinemia with cardiovascular disease (Szmitko et al., supra). Adiponectin levels in patients with coronary heart disease or cerebrovascular disease are lower than in healthy controls (Hotta et al., 2000, Arterioscler Thromb Vasc Biol 20:1595-1599; Kumada et al., 2003, Arterioscler Thromb Vasc Biol 23:85-89; Pischon et al., 2004, JAMA 291:1730-1737) and vary inversely with the severity of disease. Hypoadiponectinemia is associated with increased risk of cardiovascular disease even in nonobese individuals (Im et al., 2006, Metabolism 55:1546-1550). Significantly, adiponectin inhibits development of atherosclerosis in animal models (Okamoto et al., 2002, Circulation 106:2767-2770), providing evidence for a causal relationship between low adiponectin levels and cardiovascular disease. Therefore, there is a need for ActRIIB-derived agents and other inhibitors of ActRIIB signaling that can be used to treat or prevent hypoadiponectinemia.

SUMMARY OF THE INVENTION

In certain aspects, the present disclosure provides methods for increasing adiponectin levels in patients in need thereof by using antagonists of the ActRIIB signaling pathway. Patients in need of such therapy will typically exhibit low adiponectin, particularly in the serum. Such patients are considered to have a condition that is termed hypoadiponectinemia, Antagonists of the ActRIIB signaling pathway may be, for example, soluble ActRIIB proteins (e.g., ActRIIB-Fc fusion proteins), antagonists that bind to ActRIIB or inhibit ActRIIB expression, and antagonists that bind to or inhibit the expression of ligands that signal through ActRIIB and regulate adiponectin expression and/or secretion. Such ligands may include myostatin, GDF3, activins (particularly activin A, activin B or activin AB), BMP7, BMP2 and BMP4. As demonstrated herein, ActRIIB-Fc fusion proteins can be used to increase adiponectin gene expression and increase circulating adiponectin levels in diverse mouse models.

In certain aspects, the disclosure provides methods for increasing adiponectin, or treating hypoadiponectinemia, by administering to a patient in need thereof an effective amount of an ActRIIB-related polypeptide. An ActRIIB-related polypeptide may be an ActRIIB polypeptide (e.g., an ActRIIB extracellular domain or portion thereof) that binds to an ActRIIB ligand such as GDF3, BMP2, BMP4, BMP7, GDF8, GDF11, activin A, activin B, activin AB or nodal. Optionally, the ActRIIB polypeptide binds to an ActRIIB ligand with a Kd less than 10 micromolar or less than 1 micromolar, 100, 10 or 1 nanomolar. A variety of suitable ActRIIB polypeptides have been described in the following published PCT patent applications, all of which are incorporated by reference herein: WO 00/43781, WO 04/039948, WO 06/012627, WO 07/053,775, WO 08/097,541, and WO 08/109,167. Optionally, the ActRIIB polypeptide inhibits ActRIIB signaling, such as intracellular signal transduction events triggered by an ActRIIB ligand. A soluble ActRIIB polypeptide for use in such a preparation may be any of those disclosed herein, such as a polypeptide having an amino acid sequence selected from SEQ ID NOs: 1, 2, 5, 12, 23 and 26 or having an amino acid sequence that is at least 80%, 85%, 90%, 95%, 97% or 99% identical to an amino acid sequence selected from SEQ ID NOs: 1, 2, 5, 12, 23 and 26. A soluble ActRIIB polypeptide may include a functional fragment of a natural ActRIIB polypeptide, such as one comprising at least 10, 20 or 30 amino acids of a sequence selected from SEQ ID NOs: 1, 2, 5, 12, 23 and 26 or a sequence of SEQ ID NO: 1, lacking the C-terminal 1, 2, 3, 4, 5 or 10 to 15 amino acids and lacking 1, 2, 3, 4 or 5 amino acids at the N-terminus. Optionally, polypeptides will comprise a truncation relative to SEQ ID NO:1 of between 2 and 5 amino acids at the N-terminus and no more than 3 amino acids at the C-terminus. Another polypeptide is that presented as SEQ ID NO:12. A soluble ActRIIB polypeptide may include one, two, three, four, five or more alterations in the amino acid sequence (e.g., in the ligand-binding domain) relative to a naturally occurring ActRIIB polypeptide. The alteration in the amino acid sequence may, for example, alter glycosylation of the polypeptide when produced in a mammalian, insect or other eukaryotic cell or alter proteolytic cleavage of the polypeptide relative to the naturally occurring ActRIIB polypeptide. A soluble ActRIIB polypeptide may be a fusion protein that has, as one domain, an ActRIIB polypeptide (e.g., a ligand-binding domain of an ActRIIB or a variant thereof) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. A soluble ActRIIB fusion protein may include an immunoglobulin constant domain, such as an Fc domain (wild-type or mutant) or a serum albumin. In certain embodiments, an ActRIIB-Fc fusion comprises a relatively unstructured linker positioned between the Fc domain and the extracellular ActRIIB domain. This unstructured linker may correspond to the roughly 15 amino acid unstructured region at the C-terminal end of the extracellular domain of ActRIIB (the "tail"), or it may be an artificial sequence of between 5 and 15, 20, 30, 50 or more amino acids that are relatively free of secondary structure. A linker may be rich in glycine and proline residues and may, for example, contain repeating or non-repeating sequences of threonine/serine and/or glycines (e.g., $TG_4$ (SEQ ID NO: 6), $TG_3$ (SEQ ID NO: 27), $SG_4$ (SEQ ID NO: 28), $SG_3$ (SEQ ID NO: 29), $G_4$ (SEQ ID NO: 30), $G_3$, $G_2$, G). A fusion protein may include a purification subsequence, such as an epitope tag, a FLAG tag, a polyhistidine sequence, and a GST fusion. Optionally, a soluble ActRIIB polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. In general, it is preferable that an ActRIIB protein be expressed in a mammalian cell line that mediates suitably natural glycosylation of the ActRIIB protein so as to diminish the likelihood of an unfavorable immune response in a patient. Human and CHO cell lines have been used successfully, and it is expected that other common mammalian expression vectors will be useful.

In certain aspects, a compound disclosed herein may be formulated as a pharmaceutical preparation for increasing adiponectin in a patient in need thereof (e.g., the treatment of hypoadiponectinemia). A pharmaceutical preparation may also include one or more additional compounds such as a compound that is used to treat an ActRIIB-associated disorder. Preferably, a pharmaceutical preparation is substantially pyrogen free.

In certain aspects, the disclosure provides nucleic acids encoding a soluble ActRIIB polypeptide, which do not encode a complete ActRIIB polypeptide. An isolated polynucleotide may comprise a coding sequence for a soluble ActRIIB polypeptide, such as described above. For example, an isolated nucleic acid may include a sequence coding for an extracellular domain (e.g., ligand-binding domain) of an ActRIIB polypeptide and a sequence that would code for part or all of the transmembrane domain and/or the cytoplasmic domain of an ActRIIB, but for a stop codon positioned within the transmembrane domain or the cytoplasmic domain, or positioned between the extracellular domain and the transmembrane domain or cytoplasmic domain. For example, an isolated polynucleotide may comprise a full-length ActRIIB polynucleotide sequence such as SEQ ID NO: 4, or a partially truncated version, said isolated polynucleotide further comprising a transcription termination codon at least six hundred nucleotides before the 3'-terminus or otherwise positioned such that translation of the polynucleotide gives rise to an extracellular domain optionally fused to a truncated portion of a full-length ActRIIB. Other suitable nucleic acids that encode ActRIIB polypeptides are shown as SEQ ID NO: 3, 4, 10 or 24. Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a soluble ActRIIB polypeptide. Such a method may include expressing any of the nucleic acids (e.g., SEQ ID NO: 3, 4, 10 or 27) disclosed herein in a suitable cell, such as a Chinese hamster ovary (CHO) cell. Such a method may comprise: a) culturing a cell under conditions suitable for expression of the soluble ActRIIB polypeptide, wherein said cell is transformed with a soluble ActRIIB expression construct; and b) recovering the soluble ActRIIB polypeptide so expressed. Soluble ActRIIB polypeptides may be recovered as crude, partially purified or highly purified fractions using any of the well known techniques for obtaining protein from cell cultures.

In certain aspects, a compound described herein may be used in the management of a variety of forms of hypoadiponectinemia, including patients having low adiponectin and an associated condition (e.g., atherosclerosis, ischemic stroke, impaired glucose tolerance, insulin resistance, diabetes type 2, hyperlipidemia, hypertriglyceridemia, obesity). As shown herein, ActRIIB polypeptides may be used to increase adiponectin gene expression and/or circulating adiponectin levels while also having positive effects on body composition, specifically on muscle, bone, and adipose tissue.

In certain aspects, the disclosure provides uses of a soluble ActRIIB polypeptide for making a medicament for the treatment of a disorder or condition as described herein.

In certain aspects, the disclosure provides methods for increasing adiponectin in a patient in need thereof (e.g., treating hypoadiponectinemia), and such method may comprise administering an effective amount of a compound selected from the group consisting of: a polypeptide comprising an amino acid sequence that is at least 90%, 93%, 95%, 97%, 98%, 99% or 100% identical to SEQ ID NO: 5, 23 or 26 and a polypeptide encoded by a nucleic acid that hybridizes under stringent hybridization conditions to a nucleic acid of SEQ ID NO: 3 or 24. The polypeptide may be a fusion protein comprising a heterologous portion. The polypeptide may be a dimer. The polypeptide may be fused to a constant domain of an immunoglobulin. The polypeptide may be fused to an Fc portion of an immunoglobulin, such as an IgG1, IgG2, IgG3 or IgG4. The polypeptide may comprise an amino acid sequence that is at least 80%, 90%, 93%, 95%, 97%, 98%, 99% or 100% identical to the sequence of amino acids 29-109, 29-128, 29-131, 29-134, 25-109, 25-128, 25-131, 25-134 or 20-134 of SEQ ID NO:2. The polypeptide may comprise an amino acid sequence that is at least 80%, 90%, 93%, 95%, 97%, 98%, 99% or 100% identical to the sequence of amino acids of SEQ ID NO: 1, 2, 5, 12, 23 or 26. A patient to be treated with such a compound may be one having a disorder described herein, including, for example, hypoadiponectinemia and associated conditions (e.g., atherosclerosis, ischemic stroke, impaired glucose tolerance, insulin resistance, diabetes type 2, hyperlipidemia, hypertriglyceridemia, or obesity).

In certain aspects, the disclosure provides methods for increasing adiponectin in a patient in need thereof (e.g., treating hypoadiponectinemia), the method comprising administering an effective amount of a compound that inhibits the ActRIIB signaling pathway, either by targeting ActRIIB or a ligand that signals through ActRIIB. Examples of such compounds include antagonists of ActRIIB; antagonists of myostatin; antagonists of activin A; antagonists of activin B; antagonists of BMP2; antagonists of BMP4 and antagonists of GDF3. Antagonists of each of the foregoing may be an antibody or other protein that specifically binds to and inhibits such target (e.g., an antibody such as a monoclonal antibody, or a propeptide in the case of myostatin and GDF3). Antagonists of the foregoing may also be a compound, such as a nucleic acid based compound (e.g., an antisense or RNAi nucleic acid) that inhibits the expression of ActRIIB or the ligand. A patient to be treated with such a compound may be one having a disorder described herein, including, for example, low adiponectin level (hypoadiponectinemia), atherosclerosis, ischemic stroke, impaired glucose tolerance, insulin resistance, diabetes type 2, hyperlipidemia, hypertriglyceridemia, or obesity, and particularly any of the foregoing wherein the patient additionally exhibits low adiponectin levels.

In certain aspects, the disclosure provides methods for concurrently increasing muscle, increasing bone, and increasing fat in a patient in need thereof, the method comprising administering to the patient an effective amount of an ActRIIB fusion protein, wherein the ActRIIB fusion protein comprises an amino acid sequence that is at least 90%, 95%, 97%, 98%, 99% or 100% identical to SEQ ID NO: 1, 2, 5, 23 or 26.

In certain aspects, the disclosure provides methods for ameliorating one or more undesired effects of anti-androgen therapy in a patient in need thereof, the method comprising administering to the patient an effective amount of an ActRIIB fusion protein, wherein the ActRIIB fusion protein comprises an amino acid sequence that is at least 90%, 95%, 97%, 98%, 99% or 100% identical to SEQ ID NO: 2, 5, 23 or 26. The undesired effect of anti-androgen therapy may be, for example, muscle loss, bone loss, increased adiposity, or increased insulin resistance, or combinations of the foregoing. In an exemplary embodiment, the undesired effect of anti-androgen therapy is a combination of three or more of muscle loss, bone loss, increased adiposity and insulin resistance.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows a human ActRIIB soluble (extracellular) polypeptide sequence (SEQ ID NO: 1). The C-terminal "tail" is underlined.

FIG. 2 shows human ActRIIB precursor protein sequence (SEQ ID NO: 2). The signal peptide is underlined; the extracellular domain is in bold (also referred to as SEQ ID NO: 1); and the potential N-linked glycosylation sites are boxed.

FIG. 3 shows a nucleic acid sequence encoding a human ActRIIB soluble (extracellular) polypeptide, designated as SEQ ID NO: 3.

FIG. 4 shows a nucleic acid sequence encoding human ActRIIB precursor protein, designated as SEQ ID NO: 4.

FIG. 5 shows an alignment of human ActRIIA (SEQ ID NO: 14) and ActRIIB (SEQ ID NO: 33) with the residues that are deduced herein, based on composite analysis of multiple ActRIIB and ActRIIA crystal structures to directly contact ligand (the ligand binding pocket) indicated with boxes.

FIG. 6 shows a multiple sequence alignment of various vertebrate ActRIIB proteins and human ActRIIA.

FIG. 7 shows the full amino acid sequence of ActRIIB(25-131)-hFc (SEQ ID NO: 23). The TPA leader (residues 1-22) and truncated ActRIIB extracellular domain (native residues 25-131) are each underlined. Highlighted is the glutamate revealed by sequencing to be the N-terminal amino acid of the mature fusion protein. FIG. 7 discloses SEQ ID NO: 24.

FIG. 8 shows a nucleotide sequence encoding ActRIIB(25-131)-hFc (SEQ ID NO: 24) (the coding strand is shown at top (SEQ ID NO: 25) and the complement shown at bottom 3'-5'). Sequences encoding the TPA leader (nucleotides 1-66) and ActRIIB extracellular domain (nucleotides 73-396) are underlined. The corresponding amino acid sequence for ActRIIB(25-131) is also shown (protein sequence is disclosed as residues 25-131 of SEQ ID NO: 24).

DETAILED DESCRIPTION

1. Overview

Figure 9:
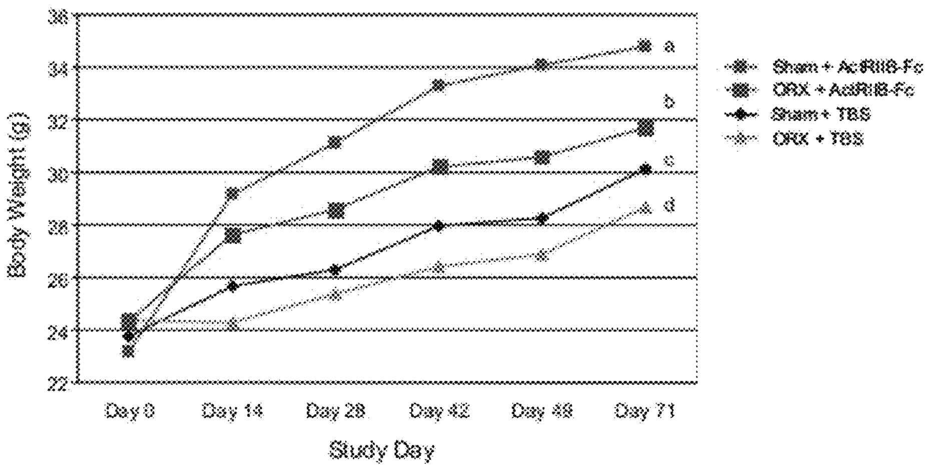
FIG. 9 shows body weight vs. time in mice as a function of ORX and ActRIIB(R64 20-134)-mFc treatment. Vehicle was Tris-buffered saline (TBS). Data shown are means (n=10 per group), and Day 71 means that differ significantly (P<0.05, two-tailed unpaired t-test) are designated by different letters. ActRIIB(R64 20-134)-mFc increased overall body weight gain under both ORX and gonad-intact conditions.

In certain aspects, the present invention relates to adiponectin (also known as Acrp30, AdipoQ, apM1, and GBP28), a polypeptide hormone (247 amino acids) released from adipocytes in multimeric form. Adiponectin acts through two receptors: AdipoR1, which is expressed in skeletal muscle, vascular endothelial cells, cardiomyocytes, and pancreatic 0 cells, and AdipoR2, which is expressed in liver and endothelial cells. Whereas other prominent adipokines (adipocyte-derived hormones) such as leptin and resistin are considered proinflammatory, adiponectin exerts anti-inflammatory effects that seem to serve a counterbalancing role (Szmitko et al., 2007, Am J Physiol Heart Circ Physiol 292: H1655-H1663). Circulating levels of adiponectin vary inversely with adipose mass, and thus low adiponectin levels (hypoadiponectinemia) may partially mediate the increased risk of cardiovascular disease and type 2 diabetes associated with obesity. However, hypoadiponectinemia is associated with increased risk of cardiovascular disease and diabetes even in nonobese individuals (Pellme et al., 2003, Diabetes 52:1182-1186; Im et al., 2006, Metabolism 55:1546-1550). Thus the state having abnormally low adiponectin levels is understood to represent an independent dysfunctional state, and may also identify subset of patients afflicted with another condition (e.g., type II diabetes, obesity or cardiovascular disease) that are particularly amenable to treatment with an agent described herein.

Evidence suggests a causal protective role for adiponectin in the development of cardiovascular disease. Adiponectin levels in patients with coronary heart disease or cerebrovascular disease are lower than in healthy controls (Hotta et al., 2000, Arterioscler Thromb Vasc Biol 20:1595-1599; Kumada et al., 2003, Arterioscler Thromb Vasc Biol 23:85-89; Pischon et al., 2004, JAMA 291:1730-1737) and vary inversely with the severity of disease. Moreover, administration of adiponectin inhibits development of atherosclerosis in animal models (Okamoto et al., 2002, Circulation 106:2767-2770), providing evidence for a causal relationship between adiponectin levels and cardiovascular disease. As described in the Examples, ActRIIB-Fc fusion proteins can be used to increase circulating adiponectin levels in diverse mouse models. Therefore, ActRIIB-derived agents and other compounds that inhibit ActRIIB signaling can be used to treat or prevent hypoadiponectinemia and to treat a subset of patients having a condition such as cardiovascular disease, diabetes, and obesity coupled with low adiponectin.

Low adiponectin, or hypoadiponectinemia, may be understood as the set of patients in the lowest quintile of adiponectin levels (below about 10.5 mg/L per Pischon et al. JAMA 2004; 291: 1730-1737), and preferably below 4.0 mg/L or below 2.5 mg/L (see also Im et al. Metabolism 2006; 55:1546-1550; Kumada et al. Arterioscler Thromb Vasc Biol 2003; 23:85-89; Ryo et al. Circ J 2004; 68:975-981; Tsukinoki et al. Lipids Health Dis 2005; 4:27). Values may be slightly higher in women than in men.

In certain aspects, the present invention relates to ActRIIB polypeptides. As used herein, the term "ActRIIB" refers to a family of activin receptor type JIB (ActRIIB) proteins and ActRIIB-related proteins, derived from any species. Members of the ActRIIB family are generally all transmembrane proteins, composed of a ligand-binding extracellular domain with cysteine-rich region, a transmembrane domain, and a cytoplasmic domain with predicted serine/threonine kinase specificity. The amino acid sequence of human ActRIIB precursor protein, including the native leader, is illustrated in FIG. 2 (SEQ ID NO: 2) and is used throughout this disclosure as the base sequence for numbering the amino acids of any of the various truncations, mature forms, and variants of ActRIIB.

The term "ActRIIB polypeptide" is used to refer to polypeptides comprising any naturally occurring polypeptide of an ActRIIB family member as well as any variants thereof (including mutants, fragments, fusions, and peptidomimetic forms) that retain a useful activity. For example, ActRIIB polypeptides include polypeptides derived from the sequence of any known ActRIIB having a sequence at least about 80% identical to the sequence of an ActRIIB polypeptide, and preferably at least 85%, 90%, 95%, 97%, 99% or greater identity.

In a specific embodiment, the invention relates to soluble ActRIIB polypeptides. As described herein, the term "soluble ActRIIB polypeptide" generally refers to polypeptides comprising an extracellular domain of an ActRIIB protein. The term "soluble ActRIIB polypeptide," as used herein, includes any naturally occurring extracellular domain of an ActRIIB protein as well as any variants thereof (including mutants, fragments and peptidomimetic forms) that retain a useful activity. For example, the extracellular domain of an ActRIIB protein binds to a ligand and is generally soluble. Examples of soluble ActRIIB polypeptides include ActRIIB soluble polypeptides illustrated in FIG. 1 (SEQ ID NO: 1) as well as SEQ ID Nos. 5 and 23. Other examples of soluble ActRIIB polypeptides comprise a signal sequence in addition to the extracellular domain of an ActRIIB protein, see Example 1. The signal sequence can be a native signal sequence of an ActRIIB, or a signal sequence from another protein, such as a tissue plasminogen activator (TPA) signal sequence or a honey bee melatin (HBM) signal sequence.

TGF-β signals are mediated by heteromeric complexes of type I and type II serine/threonine kinase receptors, which phosphorylate and activate downstream Smad proteins upon ligand stimulation (Massagué, 2000, Nat. Rev. Mol. Cell. Biol. 1:169-178). These type I and type II receptors are all transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Two related type II receptors, ActRIIA and ActRIIB, have been identified as the type II receptors for activins (Mathews and Vale, 1991, Cell 65:973-982; Attisano et al., 1992, Cell 68: 97-108). Besides activins, ActRIIA and ActRIIB can biochemically interact with several other TGF-β family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell. 7: 949-957; Oh et al., 2002, Genes Dev. 16:2749-54.

In certain embodiments, the present invention relates to antagonizing a ligand of ActRIIB receptors (also referred to as an ActRIIB ligand) with a subject ActRIIB polypeptide (e.g., a soluble ActRIIB polypeptide). Thus, compositions and methods of the present invention are useful for treating disorders associated with abnormal activity of one or more ligands of ActRIIB receptors. Exemplary ligands of ActRIIB receptors include some TGF-β family members, such as activin, Nodal, GDF8, GDF11, and BMP7.

Activins are dimeric polypeptide growth factors and belong to the TGF-beta superfamily. There are three activins (A, B, and AB) that are homo/heterodimers of two closely related 0 subunits ($\beta_A\beta_A$, $\beta_B\beta_B$, and $\beta_A\beta_B$). In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc SocEp Biol Med. 198: 500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It was suggested that activin A acts as a natural regulator of erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP), $\alpha_2$-macroglobulin, Cerberus, and endoglin, which are described below.

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as Smad proteins. Recent studies support the idea that ActRIIA and ActRIIB serve as type II receptors for Nodal (Sakuma et al., Genes Cells. 2002, 7:401-12). It is suggested that Nodal ligands interact with their co-factors (e.g., cripto) to activate activin type I and type II receptors, which phosphorylate Smad2. Nodal proteins are implicated in many events critical to the early vertebrate embryo, including mesoderm formation, anterior patterning, and left-right axis specification. Experimental evidence has demonstrated that Nodal signaling activates pAR3-Lux, a luciferase reporter previously shown to respond specifically to activin and TGF-beta. However, Nodal is unable to induce pTlx2-Lux, a reporter specifically responsive to bone morphogenetic proteins. Recent results provide direct biochemical evidence that Nodal signaling is mediated by both activin-TGF-beta pathway Smads, Smad2 and Smad3. Further evidence has shown that the extracellular cripto protein is required for Nodal signaling, making it distinct from activin or TGF-beta signaling.

Growth and Differentiation Factor-8 (GDF8) is also known as myostatin. GDF8 is a negative regulator of skeletal muscle mass. GDF8 is highly expressed in the developing and adult skeletal muscle. The GDF8 null mutation in transgenic mice is characterized by a marked hypertrophy and hyperplasia of the skeletal muscle (McPherron et al., Nature, 1997, 387:83-90). Similar increases in skeletal muscle mass are evident in naturally occurring mutations of GDF8 in cattle (Ashmore et al., 1974, Growth, 38:501-507; Swatland and Kieffer, J. Anim. Sci., 1994, 38:752-757; McPherron and Lee, Proc. Natl. Acad. Sci. USA, 1997, 94:12457-12461; and Kambadur et al., Genome Res., 1997, 7:910-915) and, strikingly, in humans (Schuelke et al., N Engl J Med 2004; 350:2682-8). Studies have also shown that muscle wasting associated with HIV-infection in humans is accompanied by increases in GDF8 protein expression (Gonzalez-Cadavid et al., PNAS, 1998, 95:14938-43). In addition, GDF8 can modulate the production of muscle-specific enzymes (e.g., creatine kinase) and modulate myoblast cell proliferation (WO 00/43781). The GDF8 propeptide can noncovalently bind to the mature GDF8 domain dimer, inactivating its biological activity (Miyazono et al. (1988) J. Biol. Chem., 263: 6407-6415; Wakefield et al. (1988) J. Biol. Chem., 263; 7646-7654; and Brown et al. (1990) Growth Factors, 3: 35-43). Other proteins which bind to GDF8 or structurally related proteins and inhibit their biological activity include follistatin, and potentially, follistatin-related proteins (Gamer et al. (1999) Dev. Biol., 208: 222-232).

Growth and Differentiation Factor-11 (GDF11), also known as BMP11, is a secreted protein (McPherron et al., 1999, Nat. Genet. 22: 260-264). GDF11 is expressed in the tail bud, limb bud, maxillary and mandibular arches, and dorsal root ganglia during mouse development (Nakashima et al., 1999, Mech. Dev. 80: 185-189). GDF11 plays a unique role in patterning both mesodermal and neural tissues (Gamer et al., 1999, Dev Biol., 208:222-32). GDF11 was shown to be a negative regulator of chondrogenesis and myogenesis in developing chick limb (Gamer et al., 2001, Dev Biol. 229: 407-20). The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium (Wu et al., 2003, Neuron. 37:197-207). Hence, GDF11 may have in vitro and in vivo applications in the treatment of diseases such as muscle diseases and neurodegenerative diseases (e.g., amyotrophic lateral sclerosis).

Bone morphogenetic protein (BMP7), also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in adipocyte differentiation and brown fat formation. Like activin, BMP7 binds to type II receptors, ActRIIA and IIB. However, BMP7 and activin recruit distinct type I receptors into heteromeric receptor complexes. The major BMP7 type I receptor observed was ALK2, while activin bound exclusively to ALK4 (ActRIIB). BMP7 and activin elicited distinct biological responses and activated different Smad pathways (Macias-Silva et al., 1998, J Biol. Chem. 273:25628-36).

In certain aspects, the present invention relates to the use of certain ActRIIB polypeptides (e.g., soluble ActRIIB polypeptides) to antagonize the signaling of ActRIIB ligands generally, in any process associated with ActRIIB activity. Optionally, ActRIIB polypeptides of the invention may antagonize one or more ligands of ActRIIB receptors, such as activins, Nodal, GDF8, GDF11, and BMP7, and may therefore be useful in the treatment of additional disorders.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. ActRIIB Polypeptides

In certain aspects, the invention relates to ActRIIB variant polypeptides (e.g., soluble ActRIIB polypeptides). Optionally, the fragments, functional variants, and modified forms have similar or the same biological activities of their corresponding wild-type ActRIIB polypeptides. For example, an ActRIIB variant of the invention may bind to and inhibit function of an ActRIIB ligand (e.g., activin A, activin AB, activin B, Nodal, GDF8, GDF11 or BMP7). Optionally, an ActRIIB polypeptide modulates growth of tissues such as bone, cartilage, muscle or fat. Examples of ActRIIB polypeptides include human ActRIIB precursor polypeptide (SEQ ID NO: 2), and soluble human ActRIIB polypeptides (e.g., SEQ ID NOs: 1, 2, 5, 12, 23 and 26).

The disclosure identifies functionally active portions and variants of ActRIIB. Applicants have ascertained that an Fc fusion protein having the sequence disclosed by Hilden et al. (Blood. 1994 Apr. 15; 83(8):2163-70), which has an Alanine at the position corresponding to amino acid 64 of SEQ ID NO: 2 (A64), has a relatively low affinity for activin and GDF-11. By contrast, the same Fc fusion protein with an Arginine at position 64 (R64) has an affinity for activin and GDF-11 in the low nanomolar to high picomolar range. Therefore, a sequence with an R64 is used as the wild-type reference sequence for human ActRIIB in this disclosure.

Attisano et al. (Cell. 1992 Jan. 10; 68(1):97-108) showed that a deletion of the proline knot at the C-terminus of the extracellular domain of ActRIIB reduced the affinity of the receptor for activin. Data presented here shows that an ActRIIB-Fc fusion protein containing amino acids 20-119 of SEQ ID NO:2, "ActRIIB(20-119)-Fc" has reduced binding to GDF-11 and activin relative to an ActRIIB(20-134)-Fc, which includes the proline knot region and the complete juxtamembrane domain. However, an ActRIIB(20-129)-Fc protein retains similar but somewhat reduced activity relative to the wild type, even though the proline knot region is disrupted. Thus, ActRIIB extracellular domains that stop at amino acid 134, 133, 132, 131, 130 and 129 are all expected to be active, but constructs stopping at 134 or 133 may be most active. Similarly, mutations at any of residues 129-134 are not expected to alter ligand binding affinity by large margins. In support of this, mutations of P129 and P130 do not substantially decrease ligand binding. Therefore, an ActRIIB-Fc fusion protein may end as early as amino acid 109 (the final cysteine), however, forms ending at or between 109 and 119 are expected to have reduced ligand binding. Amino acid 119 is poorly conserved and so is readily altered or truncated. Forms ending at 128 or later retain ligand binding activity. Forms ending at or between 119 and 127 will have an intermediate binding ability. Any of these forms may be desirable to use, depending on the clinical or experimental setting.

At the N-terminus of ActRIIB, it is expected that a protein beginning at amino acid 29 or before will retain ligand binding activity. Amino acid 29 represents the initial cysteine. An alanine to asparagine mutation at position 24 introduces an N-linked glycosylation sequence without substantially affecting ligand binding. This confirms that mutations in the region between the signal cleavage peptide and the cysteine cross-linked region, corresponding to amino acids 20-29 are well tolerated. In particular, constructs beginning at position 20, 21, 22, 23 and 24 will retain activity, and constructs beginning at positions 25, 26, 27, 28 and 29 are also expected to retain activity.

Taken together, an active portion of ActRIIB comprises amino acids 29-109 of SEQ ID NO:2, presented here as SEQ ID NO: 26:

```
CIYYNANWELERTNQSGLERCEGEQDKRLHCYASWRNSSGTIELVKKGCW
LDDFNCYDRQECVATEENPQVYFCCCEGNFC
```

Constructs may, for example, begin at a residue corresponding to amino acids 20-29 and end at a position corresponding to amino acids 109-134 of SEQ ID NO: 2. Other examples include constructs that begin at a position from 20-29 or 21-29 and end at a position from 119-134, 119-133 or 129-134, 129-133. Other examples include constructs that begin at a position from 20-24 (or 21-24, or 22-25) and end at a position from 109-134 (or 109-133), 119-134 (or 119-133) or 129-134 (or 129-133). Variants within these ranges are also contemplated, particularly those having at least 80%, 85%, 90%, 95% or 99% identity to the corresponding portion of SEQ ID NO:4.

The disclosure includes the results of an analysis of composite ActRIIB structures, shown in FIG. 5, demonstrating that the ligand binding pocket is defined by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated, although a K74A mutation is well-tolerated, as are R40A, K55A, F82A and mutations at position L79. R40 is a K in *Xenopus*, indicating that basic amino acids at this position will be tolerated. Q53 is R in bovine ActRIIB and K in *Xenopus* ActRIIB, and therefore amino acids including R, K, Q, N and H will be tolerated at this position. Thus, a general formula for an active ActRIIB variant protein is one that comprises amino acids 29-109, but optionally beginning at a position ranging from 20-24 or 22-25 and ending at a position ranging from 129-134, and comprising no more than 1, 2, 5, 10 or 15 conservative amino acid changes in the ligand binding pocket, and zero, one or more non-conservative alterations at positions 40, 53, 55, 74, 79 and/or 82 in the ligand binding pocket. Such a protein may retain greater than 80%, 90%, 95% or 99% sequence identity to the sequence of amino acids 29-109 of SEQ ID NO:4. Sites outside the binding pocket, at which variability may be particularly well tolerated, include the amino and carboxy termini of the extracellular domain (as noted above), and positions 42-46 and 65-73. An asparagine to alanine alteration at position 65 (N65A) actually improves ligand binding in the A64 background, and is thus expected to have no detrimental effect on ligand binding in the R64 background. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64.

ActRIIB is well-conserved across nearly all vertebrates, with large stretches of the extracellular domain conserved completely. Many of the ligands that bind to ActRIIB are also highly conserved. Accordingly, comparisons of ActRIIB sequences from various vertebrate organisms provide insights into residues that may be altered. Therefore, an active, human ActRIIB variant may include one or more amino acids at corresponding positions from the sequence of another vertebrate ActRIIB, or may include a residue that is similar to that in the human or other vertebrate sequence. The following examples illustrate this approach to defining an active ActRIIB variant. L46 is a valine in *Xenopus* ActRIIB, and so this position may be altered, and optionally may be altered to another hydrophobic residue, such as V, I or F, or a non-polar residue such as A. E52 is a K in *Xenopus*, indicating that this site may be tolerant of a wide variety of changes, including polar residues, such as E, D, K, R, H, S, T, P, G, Y and probably A. T93 is a K in *Xenopus*, indicating that a wide structural variation is tolerated at this position, with polar residues favored, such as S, K, R, E, D, H, G, P, G and Y. F108 is a Y in *Xenopus*, and therefore Y or other hydrophobic group, such as I, V or L should be tolerated. E111 is K in *Xenopus*, indicating that charged residues will be tolerated at this position, including D, R, K and H, as well as Q and N. R112 is K in *Xenopus*, indicating that basic residues are tolerated at this position, including R and H. A at position 119 is relatively poorly conserved, and appears as P in rodents and V in *Xenopus*, thus essentially any amino acid should be tolerated at this position.

Further N-linked glycosylation sites (N-X-S/T) may be introduced into the ActRIIb sequence. By introducing an asparagine at position 24 (A24N construct), an NXT sequence is created. Other NX(T/S) sequences are found at 42-44 (NQS) and 65-67 (NSS), although the latter may not be efficiently glycosylated with the R at position 64. N-X-S/T sequences may be generally introduced at positions outside the ligand binding pocket defined in FIG. 12. Particularly suitable sites for the introduction of non-endogenous N-X-S/T sequences include amino acids 20-29, 20-24, 22-25, 109-134, 120-134 or 129-134. N-X-S/T sequences may also be introduced into the linker between the ActRIIB sequence and the Fc or other fusion component. Such a site may be introduced with minimal effort by introducing an N in the correct position with respect to a pre-existing S or T, or by introducing an S or T at a position corresponding to a pre-existing N. Thus, desirable alterations that would create an N-linked glycosylation site are: A24N, R64N, S67N (possibly combined with an N65A alteration), E106N, R112N, G120N, E123N, P129N, A132N, R112S and R112T. Any S that is predicted to be glycosylated may be altered to a T without creating an immunogenic site, because of the protection afforded by the glycosylation. Likewise, any T that is predicted to be glycosylated may be altered to an S. Thus the alterations S67T and S44T are contemplated. Likewise, in an A24N variant, an S26T alteration may be used. Accordingly, an ActRIIB variant may include one or more additional, non-endogenous N-linked glycosylation consensus sequences.

The variations described may be combined in various ways. Additionally, the results of mutagenesis program described previously in WO 2006/012627 and WO 2008/097541 indicate that there are amino acid positions in ActRIIb that are often beneficial to conserve. These include position 64 (basic amino acid), position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus the disclosure provides a framework of amino acids that may be conserved. Other positions that may be desirable to conserve are as follows: position 52 (acidic amino acid), position 55 (basic amino acid), position 81 (acidic), 98 (polar or charged, particularly E, D, R or K).

In certain embodiments, isolated fragments of the ActRIIB polypeptides can be obtained by screening polypeptides recombinantly produced from the corresponding fragment of the nucleic acid encoding an ActRIIB polypeptide (e.g., SEQ ID NOs: 3 and 4). In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function, for example, as antagonists (inhibitors) or agonists (activators) of an ActRIIB protein or an ActRIIB ligand.

In certain embodiments, a functional variant of the ActRIIB polypeptides has an amino acid sequence that is at least 75% identical to an amino acid sequence selected from SEQ ID NOs: 1, 2, 5, 12, 23 and 26. In certain cases, the functional variant has an amino acid sequence at least 80%, 85%, 90%, 95%, 97%, 98%, 99% or 100% identical to an amino acid sequence selected from SEQ ID NOs: 1, 2, 5, 12, 23 and 26.

In certain embodiments, the present invention contemplates making functional variants by modifying the structure of an ActRIIB polypeptide for such purposes as enhancing therapeutic efficacy, or stability (e.g., ex vivo shelf life and resistance to proteolytic degradation in vivo). Modified ActRIIB polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIB polypeptide results in a functional homolog can be readily determined by assessing the ability of the variant ActRIIB polypeptide to produce a response in cells in a fashion similar to the wild-type ActRIIB polypeptide, or to bind to one or more ligands, such as activin, GDF-11 or myostatin in a fashion similar to wild type.

In certain specific embodiments, the present invention contemplates making mutations in the extracellular domain (also referred to as ligand-binding domain) of an ActRIIB polypeptide such that the variant (or mutant) ActRIIB polypeptide has altered ligand-binding activities (e.g., binding affinity or binding specificity). In certain cases, such variant ActRIIB polypeptides have altered (elevated or reduced) binding affinity for a specific ligand. In other cases, the variant ActRIIB polypeptides have altered binding specificity for their ligands.

For example, the disclosure provides variant ActRIIB polypeptides that preferentially bind to GDF8/GDF11 relative to activins. The disclosure further establishes the desirability of such polypeptides for reducing off-target effects, although such selective variants may be less desirable for the treatment of severe diseases where very large gains in muscle mass may be needed for therapeutic effect and where some level of off-target effect is acceptable. For example, amino acid residues of the ActRIIB protein, such as E39, K55, Y60, K74, W78, D80, and F101, are in the ligand-binding pocket and mediate binding to its ligands such as activin and GDF8. Thus, the present invention provides an altered ligand-binding domain (e.g., GDF8-binding domain) of an ActRIIB receptor, which comprises one or more mutations at those amino acid residues. Optionally, the altered ligand-binding domain can have increased selectivity for a ligand such as GDF8 relative to a wild-type ligand-binding domain of an ActRIIB receptor. To illustrate, these mutations increase the selectivity of the altered ligand-binding domain for GDF8 over activin. Optionally, the altered ligand-binding domain has a ratio of $K_d$ for activin binding to $K_d$ for GDF8 binding that is at least 2, 5, 10, or even 100 fold greater relative to the ratio for the wild-type ligand-binding domain. Optionally, the altered ligand-binding domain has a ratio of $IC_{50}$ for inhibiting activin to $IC_{50}$ for inhibiting GDF8 that is at least 2, 5, 10, or even 100 fold greater relative to the wild-type ligand-binding domain. Optionally, the altered ligand-binding domain inhibits GDF8 with an $IC_{50}$ at least 2, 5, 10, or even 100 times less than the $IC_{50}$ for inhibiting activin.

As a specific example, the positively-charged amino acid residue Asp (D80) of the ligand-binding domain of ActRIIB can be mutated to a different amino acid residue such that the variant ActRIIB polypeptide preferentially binds to GDF8, but not activin. Preferably, the D80 residue is changed to an amino acid residue selected from the group consisting of: a uncharged amino acid residue, a negative amino acid residue, and a hydrophobic amino acid residue. As a further specific example, the hydrophobic residue, L79, can be altered to the acidic amino acids aspartic acid or glutamic acid to greatly reduce activin binding while retaining GDF11 binding. As will be recognized by one of skill in the art, most of the described mutations, variants or modifications may be made at the nucleic acid level or, in some cases, by post translational modification or chemical synthesis. Such techniques are well known in the art.

In certain embodiments, the present invention contemplates specific mutations of the ActRIIB polypeptides so as to alter the glycosylation of the polypeptide. Exemplary glycosylation sites in ActRIIB polypeptides are illustrated in FIG. 2. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (where "X" is any amino acid) which is specifically recognized by appropriate cellular glycosylation enzymes. The alteration may also be made by the addition of, or substitution by, one or more serine or threonine residues to the sequence of the wild-type ActRIIB polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIB polypeptide is by chemical or enzymatic coupling of glycosides to the ActRIIB polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on an ActRIIB polypeptide may be accomplished chemically and/or enzymatically. Chemical deglycosylation may involve, for example, exposure of the ActRIIB polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on ActRIIB polypeptides can be achieved by the use of a variety of endo- and exo-glycosidases as described by Thotakura et al. (1987) Meth. Enzymol. 138:350. The sequence of an ActRIIB polypeptide may be adjusted, as appropriate, depending on the type of expression system used, as mammalian, yeast, insect and plant cells may all introduce differing glycosylation patterns that can be affected by the amino acid sequence of the peptide. In general, ActRIIB proteins for use in humans will be expressed in a mammalian cell line that provides proper glycosylation, such as HEK293 or CHO cell lines, although other mammalian expression cell lines are expected to be useful as well.

This disclosure further contemplates a method of generating variants, particularly sets of combinatorial variants of an ActRIIB polypeptide, including, optionally, truncation variants; pools of combinatorial mutants are especially useful for identifying functional variant sequences. The purpose of screening such combinatorial libraries may be to generate, for example, ActRIIB polypeptide variants which have altered properties, such as altered pharmacokinetics, or altered ligand binding. A variety of screening assays are provided below, and such assays may be used to evaluate variants. For example, an ActRIIB polypeptide variant may be screened for ability to bind to an ActRIIB polypeptide, to prevent binding of an ActRIIB ligand to an ActRIIB polypeptide.

Combinatorially-derived variants can be generated which have a selective potency relative to a naturally occurring ActRIIB polypeptide. Such variant proteins, when expressed from recombinant DNA constructs, can be used in gene therapy protocols. Likewise, mutagenesis can give rise to variants which have intracellular half-lives dramatically different than the corresponding a wild-type ActRIIB polypeptide. For example, the altered protein can be rendered either more stable or less stable to proteolytic degradation or other processes which result in destruction of, or otherwise inactivation of a native ActRIIB polypeptide. Such variants, and the genes which encode them, can be utilized to alter ActRIIB polypeptide levels by modulating the half-life of the ActRIIB polypeptides. For instance, a short half-life can give rise to more transient biological effects and, when part of an inducible expression system, can allow tighter control of recombinant ActRIIB polypeptide levels within the cell.

In certain embodiments, the ActRIIB polypeptides of the invention may further comprise post-translational modifications in addition to any that are naturally present in the ActRIIB polypeptides. Such modifications include, but are not limited to, acetylation, carboxylation, glycosylation, phosphorylation, lipidation, and acylation. As a result, the modified ActRIIB polypeptides may contain non-amino acid elements, such as polyethylene glycols, lipids, poly- or mono-saccharide, and phosphates. Effects of such non-amino acid elements on the functionality of an ActRIIB polypeptide may be tested as described herein for other ActRIIB polypeptide variants. When an ActRIIB polypeptide is produced in cells by cleaving a nascent form of the ActRIIB polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ActRIIB polypeptides.

In certain aspects, functional variants or modified forms of the ActRIIB polypeptides include fusion proteins having at least a portion of the ActRIIB polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (e.g., an Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$ (SEQ ID NO: 31)) fusion partners. As another example, a fusion domain may be selected so as to facilitate detection of the ActRIIB polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIB polypeptide is fused with a domain that stabilizes the ActRIIB polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

The following is a specific example of Fc domains that may be used (e.g., SEQ ID NO: 13).

THTCPPCPAPELLGGPSVFLFPPKP-
KDTLMISRTPEVTCVVV
<u>D</u>(A)VSHEDPEVKFNWYVDGVE VHNAKTKPRE-
EQYNSTYRVVSVLTVLHQDWLNGKEYKC
<u>K</u>(A)VSNKALPVPIEKTISKAKGQPR
EPQVYTLPPSREEMTKNQVSLTCLVKGF-
YPSDIAVEWESNGQPENNYKTTPPVLDSDGPFFLYS
KLTVDKSRWQQGNVFSCSVMHEALH
<u>N</u>(A)HYTQKSLSLSPGK*

The Fc domain may have one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

It is understood that different elements of the fusion proteins may be arranged in any manner that is consistent with the desired functionality. For example, an ActRIIB polypeptide may be placed C-terminal to a heterologous domain, or, alternatively, a heterologous domain may be placed C-terminal to an ActRIIB polypeptide. The ActRIIB polypeptide domain and the heterologous domain need not be adjacent in a fusion protein, and additional domains or amino acid sequences may be included C- or N-terminal to either domain or between the domains.

In the case of fusion proteins, an ActRIIB polypeptide may be fused to a stabilizer domain such as an IgG molecule (e.g., an Fc domain). As used herein, the term "stabilizer domain" not only refers to a fusion domain (e.g., Fc) as in the case of fusion proteins, but also includes nonproteinaceous modifications such as a polyethylene glycol.

In certain embodiments, the present invention makes available isolated and/or purified forms of the ActRIIB polypeptides, which are isolated from, or otherwise substantially free of, other proteins.

In certain embodiments, ActRIIB polypeptides (unmodified or modified) of the invention can be produced by a variety of art-known techniques. For example, such ActRIIB polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the ActRIIB polypeptides, fragments or variants thereof may be recombinantly produced using various expression systems (e.g., *E. coli*, Chinese Hamster Ovary cells, COS cells, baculovirus) as is well known in the art (also see below). In a further embodiment, the modified or unmodified ActRIIB polypeptides may be produced by digestion of naturally occurring or recombinantly produced full-length ActRIIB polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites. Alternatively, such ActRIIB polypeptides may be produced from naturally occurring or recombinantly produced full-length ActRIIB polypeptides such as standard techniques known in the art, such as by chemical cleavage (e.g., cyanogen bromide, hydroxylamine).

3. Nucleic Acids Encoding ActRIIB Polypeptides

In certain aspects, the invention provides isolated and/or recombinant nucleic acids encoding any of the ActRIIB polypeptides (e.g., soluble ActRIIB polypeptides), including any of the variants disclosed herein. For example, SEQ ID NO: 4 encodes a naturally occurring ActRIIB precursor polypeptide, while SEQ ID NO: 3 encodes a soluble ActRIIB polypeptide. The subject nucleic acids may be single-stranded or double stranded. Such nucleic acids may be DNA or RNA molecules. These nucleic acids are may be used, for example, in methods for making ActRIIB polypeptides or as direct therapeutic agents (e.g., in a gene therapy approach).

In certain aspects, the subject nucleic acids encoding ActRIIB polypeptides are further understood to include nucleic acids that are variants of SEQ ID NO: 3. Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NO: 4.

In certain embodiments, the invention provides isolated or recombinant nucleic acid sequences that are at least 80%, 85%, 90%, 95%, 97%, 98%, 99% or 100% identical to SEQ ID NO: 3, 10 and 24. One of ordinary skill in the art will appreciate that nucleic acid sequences complementary to SEQ ID NO: 3, and variants of SEQ ID NO: 3 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under highly stringent conditions to the nucleotide sequence designated in SEQ ID NO: 3, 10 or 24, complement sequence of SEQ ID NO: 3, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NO: 3 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ActRIIB polypeptide and operably linked to at least one regulatory sequence. Regulatory sequences are art-recognized and are selected to direct expression of the ActRIIB polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRIIB polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIB polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art.

For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRIIB polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIB polypeptides in cells propagated in culture, e.g., to produce proteins, including fusion proteins or variant proteins, for purification.

This invention also pertains to a host cell transfected with a recombinant gene including a coding sequence (e.g., SEQ ID NO: 3, 4, 10 or 24) for one or more of the subject ActRIIB polypeptide. The host cell may be any prokaryotic or eukaryotic cell. For example, an ActRIIB polypeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject ActRIIB polypeptides. For example, a host cell transfected with an expression vector encoding an ActRIIB polypeptide can be cultured under appropriate conditions to allow expression of the ActRIIB polypeptide to occur. The ActRIIB polypeptide may be secreted and isolated from a mixture of cells and medium containing the ActRIIB polypeptide. Alternatively, the ActRIIB polypeptide may be retained cytoplasmically or in a membrane fraction and the cells harvested, lysed and the protein isolated. A cell culture includes host cells, media and other byproducts. Suitable media for cell culture are well known in the art. The subject ActRIIB polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the ActRIIB polypeptides. In a preferred embodiment, the ActRIIB polypeptide is a fusion protein containing a domain which facilitates its purification.

In another embodiment, a fusion gene coding for a purification leader sequence, such as a poly-(His)/enterokinase cleavage site sequence at the N-terminus of the desired portion of the recombinant ActRIIB polypeptide, can allow purification of the expressed fusion protein by affinity chromatography using a $Ni^{2+}$ metal resin. The purification leader sequence can then be subsequently removed by treatment with enterokinase to provide the purified ActRIIB polypeptide (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Antibodies

Another aspect of the invention pertains to antibodies. An antibody that is specifically reactive with an ActRIIB polypeptide (e.g., a soluble ActRIIB polypeptide) and which binds competitively with the ActRIIB polypeptide may be used as an antagonist of ActRIIB polypeptide activities. For example, by using immunogens derived from an ActRIIB polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the ActRIIB polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ActRIIB polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an ActRIIB polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an ActRIIB polypeptide and monoclonal antibodies isolated from a culture comprising such hybridoma cells.

The term "antibody" as used herein is intended to include fragments thereof which are also specifically reactive with a subject ActRIIB polypeptide. Antibodies can be fragmented using conventional techniques and the fragments screened for utility in the same manner as described above for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanized molecules having affinity for an ActRIIB polypeptide conferred by at least one CDR region of the antibody. In preferred embodiments, the antibody further comprises a label attached thereto and able to be detected (e.g., the label can be a radioisotope, fluorescent compound, enzyme or enzyme co-factor).

In certain preferred embodiments, an antibody of the invention is a monoclonal antibody, and in certain embodiments, the invention makes available methods for generating novel antibodies. For example, a method for generating a monoclonal antibody that binds specifically to an ActRIIB polypeptide may comprise administering to a mouse an amount of an immunogenic composition comprising the ActRIIB polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the ActRIIB polypeptide. Once obtained, a hybridoma can be propagated in a cell culture, optionally in culture conditions where the hybridoma-derived cells produce the monoclonal antibody that binds specifically to the ActRIIB polypeptide. The monoclonal antibody may be purified from the cell culture.

The adjective "specifically reactive with" as used in reference to an antibody is intended to mean, as is generally understood in the art, that the antibody is sufficiently selective between the antigen of interest (e.g., an ActRIIB polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore binding assay, Bia-core AB, Uppsala, Sweden), sandwich assays (e.g., the paramagnetic bead system of IGEN International, Inc., Gaithersburg, Md.), western blots, immunoprecipitation assays, and immunohistochemistry.

In certain aspects, the disclosure provides antibodies that bind to a soluble ActRIIB polypeptide. Such antibodies may be generated much as described above, using a soluble ActRIIB polypeptide or fragment thereof as an antigen. Antibodies of this type can be used, e.g., to detect ActRIIB polypeptides in biological samples and/or to monitor soluble ActRIIB polypeptide levels in an individual. In certain cases, an antibody that specifically binds to a soluble ActRIIB polypeptide can be used to modulate activity of an ActRIIB polypeptide and/or an ActRIIB ligand, thereby regulating (promoting or inhibiting) growth of tissues, such as bone, cartilage, muscle, fat, and neurons.

5. Screening Assays

In certain aspects, the present invention relates to the use of the subject ActRIIB polypeptides (e.g., soluble ActRIIB polypeptides) to identify compounds (agents) which are agonist or antagonists of the ActRIIB polypeptides. Compounds identified through this screening can be tested in tissues such as bone, cartilage, muscle, fat, and/or neurons, to assess their ability to modulate tissue growth in vitro. Optionally, these compounds can further be tested in animal models to assess their ability to modulate tissue growth in vivo.

There are numerous approaches to screening for therapeutic agents for modulating tissue growth by targeting the ActRIIB polypeptides. In certain embodiments, high-throughput screening of compounds can be carried out to identify agents that perturb ActRIIB-mediated effects on growth of bone, cartilage, muscle, fat, and/or neurons. In certain embodiments, the assay is carried out to screen and identify compounds that specifically inhibit or reduce binding of an ActRIIB polypeptide to its binding partner, such as an ActRIIB ligand (e.g., activin, Nodal, GDF8, GDF11 or BMP7). Alternatively, the assay can be used to identify compounds that enhance binding of an ActRIIB polypeptide to its binding protein such as an ActRIIB ligand. In a further embodiment, the compounds can be identified by their ability to interact with an ActRIIB polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIB polypeptide and its binding protein (e.g., an ActRIIB ligand).

Merely to illustrate, in an exemplary screening assay of the present invention, the compound of interest is contacted with an isolated and purified ActRIIB polypeptide which is ordinarily capable of binding to an ActRIIB ligand, as appropriate for the intention of the assay. To the mixture of the compound and ActRIIB polypeptide is then added a composition containing an ActRIIB ligand. Detection and quantification of ActRIIB/ActRIIB ligand complexes provides a means for determining the compound's efficacy at inhibiting (or potentiating) complex formation between the ActRIIB polypeptide and its binding protein. The efficacy of the compound can be assessed by generating dose response curves from data obtained using various concentrations of the test compound. Moreover, a control assay can also be performed to provide a baseline for comparison. For example, in a control assay, isolated and purified ActRIIB ligand is added to a composition containing the ActRIIB polypeptide, and the formation of ActRIIB/ActRIIB ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIB polypeptide and its binding protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIB polypeptide or its binding protein, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between an ActRIIB polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between an ActRIIB polypeptide and its binding protein. See for example, U.S. Pat. No. 5,283,317; Zervos et al. (1993) Cell 72:223-232; Madura et al. (1993) J Biol Chem 268: 12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between an ActRIIB polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with an ActRIIB polypeptide of the invention. The interaction between the compound and the ActRIIB polypeptide may be covalent or non-covalent. For example, such interaction can be identified at the protein level using in vitro biochemical methods, including photocrosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an ActRIIB polypeptide. This may include a solid phase or fluid phase binding event. Alternatively, the gene encoding an ActRIIB polypeptide can be transfected with a reporter system (e.g., β-galactosidase, luciferase, or green fluorescent protein) into a cell and screened against the library preferably by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for stimulating muscle growth and increasing muscle mass, for example, by antagonizing functions of an ActRIIB polypeptide and/or an ActRIIB ligand. Therefore, any compound identified can be tested in whole cells or tissues, in vitro or in vivo, to confirm their ability to modulate muscle growth. Various methods known in the art can be utilized for this purpose. For example, methods of the invention are performed such that the signal transduction through an ActRIIB protein activated by binding to an ActRIIB ligand (e.g., GDF8) has been reduced or inhibited. It will be recognized that the growth of muscle tissue in the organism would result in an increased muscle mass in the organism as compared to the muscle mass of a corresponding organism (or population of organisms) in which the signal transduction through an ActRIIB protein had not been so effected.

For example, the effect of the ActRIIB polypeptides or test compounds on muscle cell growth/proliferation can be determined by measuring gene expression of Pax-3 and Myf-5 which are associated with proliferation of myogenic cells, and gene expression of MyoD which is associated with muscle differentiation (e.g., Amthor et al., Dev Biol. 2002, 251:241-57). It is known that GDF8 down-regulates gene expression of Pax-3 and Myf-5, and prevents gene expression of MyoD. The ActRIIB polypeptides or test compounds are expected to antagonize this activity of GDF8. Another example of cell-based assays includes measuring the proliferation of myoblasts such as C(2)C(12) myoblasts in the presence of the ActRIIB polypeptides or test compounds (e.g., Thomas et al., J Biol. Chem. 2000, 275:40235-43).

The present invention also contemplates in vivo assays to measure muscle mass and strength. For example, Whittemore et al. (Biochem Biophys Res Commun. 2003, 300:965-71) discloses a method of measuring increased skeletal muscle mass and increased grip strength in mice. Optionally, this method can be used to determine therapeutic effects of test compounds (e.g., ActRIIB polypeptides) on muscle diseases or conditions, for example those diseases for which muscle mass is limiting.

In certain aspects, the present invention provides methods and agents for modulating (stimulating or inhibiting) bone formation and increasing bone mass. Therefore, any compound identified can be tested in whole cells or tissues, in vitro or in vivo, to confirm their ability to modulate bone or cartilage growth. Various methods known in the art can be utilized for this purpose.

For example, the effect of the ActRIIB polypeptides or test compounds on bone or cartilage growth can be determined by measuring induction of Msx2 or differentiation of osteoprogenitor cells into osteoblasts in cell based assays (see, e.g., Daluiski et al., Nat. Genet. 2001, 27(1):84-8; Hino et al., Front Biosci. 2004, 9:1520-9). Another example of cell-based assays includes analyzing the osteogenic activity of the subject ActRIIB polypeptides and test compounds in mesenchymal progenitor and osteoblastic cells. To illustrate, recombinant adenoviruses expressing an ActRIIB polypeptide were constructed to infect pluripotent mesenchymal progenitor C3H10T1/2 cells, preosteoblastic C2C12 cells, and osteoblastic TE-85 cells. Osteogenic activity is then determined by measuring the induction of alkaline phosphatase, osteocalcin, and matrix mineralization (see, e.g., Cheng et al., J bone Joint Surg Am. 2003, 85-A(8):1544-52).

The present invention also contemplates in vivo assays to measure bone or cartilage growth. For example, Namkung-Matthai et al., Bone, 28:80-86 (2001) discloses a rat osteoporotic model in which bone repair during the early period after fracture is studied. Kubo et al., Steroid Biochemistry & Molecular Biology, 68:197-202 (1999) also discloses a rat osteoporotic model in which bone repair during the late period after fracture is studied. These references are incorporated by reference herein in their entirety for their disclosure of rat model for study on osteoporotic bone fracture. In certain aspects, the present invention makes use of fracture healing assays that are known in the art. These assays include fracture technique, histological analysis, and biomechanical analysis, which are described in, for example, U.S. Pat. No. 6,521,750, which is incorporated by reference in its entirety for its disclosure of experimental protocols for causing as well as measuring the extent of fractures, and the repair process.

In certain aspects, the present invention provides methods and agents for controlling weight gain and obesity. At the cellular level, adipocyte proliferation and differentiation is critical in the development of obesity, which leads to the generation of additional fat cells (adipocytes). Therefore, any compound identified can be tested in whole cells or tissues, in vitro or in vivo, to confirm their ability to modulate adipogenesis by measuring adipocyte proliferation or differentiation. Various methods known in the art can be utilized for this purpose. For example, the effect of an ActRIIB polypeptide (e.g., a soluble ActRIIB polypeptide) or test compounds on adipogenesis can be determined by measuring differentiation of 3T3-L1 preadipocytes to mature adipocytes in cell based assays, such as, by observing the accumulation of triacylglycerol in Oil Red O staining vesicles and by the appearance of certain adipocyte markers such as FABP (aP2/422) and PPARγ2. See, for example, Reusch et al., 2000, Mol Cell Biol. 20:1008-20; Deng et al., 2000, Endocrinology. 141:2370-6; Bell et al., 2000, Obes Res. 8:249-54. Another example of cell-based assays includes analyzing the role of ActRIIB polypeptides and test compounds in proliferation of adipocytes or adipocyte precursor cells (e.g., 3T3-L1 cells), such as, by monitoring bromodeoxyuridine (BrdU)-positive cells. See, for example, Pico et al., 1998, Mol Cell Biochem. 189: 1-7; Masuno et al., 2003, Toxicol Sci. 75:314-20.

It is understood that the screening assays of the present invention apply to not only the subject ActRIIB polypeptides and variants of the ActRIIB polypeptides, but also any test compounds including agonists and antagonist of the ActRIIB polypeptides. Further, these screening assays are useful for drug target verification and quality control purposes.

6. Exemplary Therapeutic Uses

In certain embodiments, compositions (e.g., ActRIIB polypeptides) of the present invention can be used for treating or preventing hypoadiponectinemia and interrelated conditions. In certain embodiments, the present invention provides methods of treating or preventing an individual in need thereof through administering to the individual a therapeutically effective amount of an ActRIIB polypeptide as described above. These methods are particularly aimed at therapeutic and prophylactic treatments of animals, and more particularly, humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established.

As demonstrated herein, ActRIIB-Fc administration in vivo promotes expression of adiponectin in white adipose tissue and increases circulating adiponectin levels in diverse mouse models. Accordingly, compositions disclosed herein may be used to treat or prevent hypoadiponectinemia and associated disorders, including to subset of patients with atherosclerosis, ischemic stroke, impaired glucose tolerance, insulin resistance, diabetes type 2, hyperlipidemia, hypertriglyceridemia, or obesity that also exhibit low circulating adiponectin.

In other related embodiments, soluble ActRIIB polypeptides and other compositions of the invention can be used as part of treatment or prevention of atherosclerosis, a chronic inflammatory condition in which artery walls thicken due to the accumulation of fatty deposits, often referred to as plaques. Risk factors for atherosclerosis include aging, diabetes mellitus, dyslipoproteinemia, obesity (abdominal or visceral adiposity), and a sedentary lifestyle.

Soluble ActRIIB polypeptides can also be used for treatment or prevention of lipodystrophic disorders, which tend to be associated with metabolic syndrome. Severe insulin resistance can result from both genetic and acquired forms of lipodystrophy, including in the latter case human immunodeficiency virus (HIV)-related lipodystrophy in patients treated with antiretroviral therapy.

In related embodiments, soluble ActRIIB polypeptides and other compositions of the invention can be used as part of treatment or prevention of diabetes mellitus type II (also known as non-insulin-dependent diabetes mellitus or adult-onset diabetes), which is characterized by elevated blood glucose in the context of insulin resistance and relative insulin deficiency. Complex and multifactorial metabolic changes in diabetes often lead to damage and functional impairment of many organs, most importantly the cardiovascular system. Diabetes mellitus type II is often associated with obesity (abdominal or visceral adiposity), hypertension, elevated cholesterol, and metabolic syndrome. Important risk factors for diabetes mellitus type II include aging, high-fat diets, and a sedentary lifestyle.

The subject ActRIIB polypeptides may further be used as a therapeutic agent for slowing or preventing the development of obesity. This approach is confirmed and supported by the data shown herein, whereby an ActRIIB-Fc protein was shown to improve metabolic status in mice on a high-fat diet.

In other embodiments, the present invention provides compositions and methods for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present invention relates to regulating body weight by administering to an animal (e.g., a human) in need thereof an ActRIIB polypeptide.

In one specific embodiment, the present invention relates to methods and compounds for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass.

As demonstrated in WO 2006/012627 and WO 2008/097541, compounds disclosed herein stimulate muscle growth. Accordingly, these compounds may be particularly useful in diseases or conditions with overlapping muscle and metabolic dysfunction.

In certain embodiments, compositions (e.g., soluble ActRIIB polypeptides) of the invention are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Moreover, declining muscle mass and diminishing physical activity contribute to an imbalance between caloric intake and energy expenditure, leading to unhealthy storage of excess energy as white adipose tissue. Exemplary muscular dystrophies that can be treated with a regimen including the subject ActRIIB polypeptides include: Duchenne Muscular Dystrophy (DMD), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (also known as Landouzy-Dejerine), Myotonic Dystrophy (MMD) (also known as Steinert's Disease), Oculopharyngeal Muscular Dystrophy (OPMD), Distal Muscular Dystrophy (DD), Congenital Muscular Dystrophy (CMD).

Duchenne Muscular Dystrophy (DMD) was first described by the French neurologist Guillaume Benjamin Amand Duchenne in the 1860s. Becker Muscular Dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is broken. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either insufficient in quantity or poor in quality. Having some dystrophin protects the muscles of those with BMD from degenerating as badly or as quickly as those of people with DMD.

For example, recent researches demonstrate that blocking or eliminating function of GDF8 (an ActRIIB ligand) in vivo can effectively treat at least certain symptoms in DMD and BMD patients. Thus, the subject ActRIIB polypeptides may act as GDF8 inhibitors (antagonists), and constitute an alternative means of blocking the functions of GDF8 and/or ActRIIB in vivo in DMD and BMD patients.

ActRIIB polypeptide-induced increased muscle mass might also benefit those suffering from muscle wasting diseases. Gonzalez-Cadavid et al. (1998, PNAS 95:14938-43) reported that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

Sarcopenia, the loss of muscle with aging is also often associated with metabolic syndrome, diabetes, arteriosclerosis, dyslipidemia, and other age-related metabolic conditions. ActRIIB polypeptide-induced muscle mass might also benefit those suffering from sarcopenia.

In particular, the present disclosure demonstrates that in certain conditions, such as androgen deprivation, agents disclosed herein can be used to promote muscle and bone formation while decreasing adiposity, and therefore, the disclosure provides methods for treating patients exhibiting low bone and muscle content and elevated adiposity may be advantageously treated with soluble ActRIIB polypeptides and other agents disclosed herein. This may be particularly beneficial in patients receiving androgen or estrogen antagonist therapy, elderly patients (e.g., combined sarcopenia, osteoporosis and obesity) and patients with a muscle wasting condition that are also receiving corticosteroid therapy.

In other embodiments, the present invention provides methods of inducing bone and/or cartilage formation, preventing bone loss, increasing bone mineralization or preventing the demineralization of bone. For example, the subject ActRIIB polypeptides and compounds identified in the present invention have application in treating osteoporosis and the healing of bone fractures and cartilage defects in humans and other animals. ActRIIB polypeptides may be useful in patients that are diagnosed with subclinical low bone density, as a protective measure against the development of osteoporosis.

In other embodiments, the present invention provides compositions and methods for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present invention relates to regulating body weight by administering to an animal (e.g., a human) in need thereof an ActRIIB polypeptide.

7. Pharmaceutical Compositions

In certain embodiments, compounds (e.g., ActRIIB polypeptides) of the present invention are formulated with a pharmaceutically acceptable carrier. For example, an ActRIIB polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to a target tissue site (e.g., bone, cartilage, muscle, fat or neurons), for example, a site having a tissue damage. Topical administration may be suitable for wound healing and tissue repair. Therapeutically useful agents other than the ActRIIB polypeptides which may also optionally be included in the composition as described above, may alternatively or additionally, be administered simultaneously or sequentially with the subject compounds (e.g., ActRIIB polypeptides) in the methods of the invention.

In certain embodiments, compositions of the present invention may include a matrix capable of delivering one or more therapeutic compounds (e.g., ActRIIB polypeptides) to a target tissue site, providing a structure for the developing tissue and optimally capable of being resorbed into the body. For example, the matrix may provide slow release of the ActRIIB polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

Certain compositions disclosed herein may be administered topically, either to skin or to mucosal membranes. The topical formulations may further include one or more of the wide variety of agents known to be effective as skin or stratum corneum penetration enhancers. Examples of these are 2-pyrrolidone, N-methyl-2-pyrrolidone, dimethylacetamide, dimethylformamide, propylene glycol, methyl or isopropyl alcohol, dimethyl sulfoxide, and azone. Additional agents may further be included to make the formulation cosmetically acceptable. Examples of these are fats, waxes, oils, dyes, fragrances, preservatives, stabilizers, and surface active agents. Keratolytic agents such as those known in the art may also be included. Examples are salicylic acid and sulfur.

Dosage forms for the topical or transdermal administration include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required. The ointments, pastes, creams and gels may contain, in addition to a subject compound of the invention (e.g., an ActRIIB polypeptide), excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a subject compound, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

In certain embodiments, pharmaceutical compositions suitable for parenteral administration may comprise one or more ActRIIB polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., ActRIIB polypeptides). The various factors will depend upon the disease to be treated. In the case of muscle disorders, factors may include, but are not limited to, amount of muscle mass desired to be formed, the muscles most affected by disease, the condition of the deteriorated muscle, the patient's age, sex, and diet, time of administration, and other clinical factors. The addition of other known growth factors to the final composition, may also affect the dosage. Progress can be monitored by periodic assessment of muscle growth and/or repair, for example, by strength testing, MRI assessment of muscle size and analysis of muscle biopsies.

In certain embodiments of the invention, one or more ActRIIB polypeptides can be administered, together (simultaneously) or at different times (sequentially or overlapping). In addition, ActRIIB polypeptides can be administered with another type of therapeutic agents, for example, a cartilage-inducing agent, a bone-inducing agent, a muscle-inducing agent, a fat-reducing, or a neuron-inducing agent. The two types of compounds may be administered simultaneously or at different times. It is expected that the ActRIIB polypeptides of the invention may act in concert with or perhaps synergistically with another therapeutic agent.

In a specific example, a variety of osteogenic, cartilage-inducing and bone-inducing factors have been described, particularly bisphosphonates. See e.g., European Patent Application Nos. 148,155 and 169,016. For example, other factors that can be combined with the subject ActRIIB polypeptides include various growth factors such as epidermal growth factor (EGF), platelet derived growth factor (PDGF), transforming growth factors (TGF-$\alpha$ and TGF-$\beta$), and insulin-like growth factor (IGF).

In certain embodiments, the present invention also provides gene therapy for the in vivo production of ActRIIB polypeptides. Such therapy would achieve its therapeutic effect by introduction of the ActRIIB polynucleotide sequences into cells or tissues having the disorders as listed above. Delivery of ActRIIB polynucleotide sequences can be achieved using a recombinant expression vector such as a chimeric virus or a colloidal dispersion system. Preferred for therapeutic delivery of ActRIIB polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRIIB polynucleotide. In one preferred embodiment, the vector is targeted to bone, cartilage, muscle or neuron cells/tissues.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRIIB polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1

Generation of an ActRIIb-Fc Fusion Protein

Applicants constructed a soluble ActRIIb fusion protein that has the extracellular domain of human ActRIIb fused to a human or mouse Fc domain with a minimal linker (three glycine amino acids) in between. The constructs are referred to as ActRIIb-hFc and ActRIIb-mFc, respectively.

ActRIIb-hFc is shown below as purified from CHO cell lines

```
                                           (SEQ ID NO: 5)
GRGEAETRECIYYNANWELERTNQSGLERCEGEQDKRLHCYASWRNSSGT
IELVKKGCWLDDFNCYDRQECVATEENPQVYFCCCEGNFCNERFTHLPEA
GGPEVTYEPPPTAPTGGGTHTCPPCPAPELLGGPSVFLFPPKPKDTLMIS
RTPEVTCVVVDVSHEDPEVKFNWYVDGVEVHNAKTKPREEQYNSTYRVVS
VLTVLHQDWLNGKEYKCKVSNKALPVPIEKTISKAKGQPREPQVYTLPPS
REEMTKNQVSLTCLVKGFYPSDIAVEWESNGQPENNYKTTPPVLDSDGSF
FLYSKLTVDKSRWQQGNVFSCSVMHEALHNHYTQKSLSLSPGK
```

The ActRIIb-hFc and ActRIIb-mFc proteins were expressed in CHO cell lines. Three different leader sequences were considered:

```
(i) Honey bee mellitin (HBML):
                                     (SEQ ID NO: 7)
MKFLVNVALVFMVVYISYIYA

(ii) Tissue Plasminogen Activator (TPA):
                                     (SEQ ID NO: 8)
MDAMKRGLCCVLLLCGAVFVSP

(iii) Native:
                                     (SEQ ID NO: 9)
MGAAAKLAFAVFLISCSSGA.
```

The selected form employs the TPA leader and has the following unprocessed amino acid sequence:

```
                                          (SEQ ID NO: 32)
MDAMKRGLCCVLLLCGAVFVSPGASGRGEAETRECIYYNANWELERTNQS
GLERCEGEQDKRLHCYASWRNSSGTIELVKKGCWLDDFNCYDRQECVATE
ENPQVYFCCCEGNFCNERFTHLPEAGGPEVTYEPPPTAPTGGGTHTCPPC
```

-continued

```
PAPELLGGPSVFLFPPKPKDTLMISRTPEVTCVVVDVSHEDPEVKFNWYV
DGVEVHNAKTKPREEQYNSTYRVVSVLTVLHQDWLNGKEYKCKVSNKALP
VPIEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSVMH
EALHNHYTQKSLSLSPGK.
```

This polypeptide is encoded by the following nucleic acid sequence

```
(SEQ ID NO: 10):
A TGGATGCAAT GAAGAGAGGG CTCTGCTGTG TGCTGCTGCT
GTGTGGAGCA GTCTTCGTTT CGCCCGGCGC CTCTGGGCGT
GGGGAGGCTG AGACACGGGA GTGCATCTAC TACAACGCCA
ACTGGGAGCT GGAGCGCACC AACCAGAGCG GCCTGGAGCG
CTGCGAAGGC GAGCAGGACA AGCGGCTGCA CTGCTACGCC
TCCTGGCGCA ACAGCTCTGG CACCATCGAG CTCGTGAAGA
AGGGCTGCTG GCTAGATGAC TTCAACTGCT ACGATAGGCA
GGAGTGTGTG GCCACTGAGG AGAACCCCCA GGTGTACTTC
TGCTGCTGTG AAGGCAACTT CTGCAACGAG CGCTTCACTC
ATTTGCCAGA GGCTGGGGGC CCGGAAGTCA CGTACGAGCC
ACCCCCGACA GCCCCCACCG GTGGTGGAAC TCACACATGC
CCACCGTGCC CAGCACCTGA ACTCCTGGGG GGACCGTCAG
TCTTCCTCTT CCCCCCAAAA CCCAAGGACA CCCTCATGAT
CTCCCGGACC CCTGAGGTCA CATGCGTGGT GGTGGACGTG
AGCCACGAAG ACCCTGAGGT CAAGTTCAAC TGGTACGTGG
ACGGCGTGGA GGTGCATAAT GCCAAGACAA AGCCGCGGGA
GGAGCAGTAC AACAGCACGT ACCGTGTGGT CAGCGTCCTC
ACCGTCCTGC ACCAGGACTG GCTGAATGGC AAGGAGTACA
AGTGCAAGGT CTCCAACAAA GCCCTCCCAG TCCCCATCGA
GAAAACCATC TCCAAAGCCA AAGGGCAGCC CCGAGAACCA
CAGGTGTACA CCCTGCCCCC ATCCCGGGAG GAGATGACCA
AGAACCAGGT CAGCCTGACC TGCCTGGTCA AAGGCTTCTA
TCCCAGCGAC ATCGCCGTGG AGTGGGAGAG CAATGGGCAG
CCGGAGAACA ACTACAAGAC CACGCCTCCC GTGCTGGACT
CCGACGGCTC CTTCTTCCTC TATAGCAAGC TCACCGTGGA
CAAGAGCAGG TGGCAGCAGG GGAACGTCTT CTCATGCTCC
GTGATGCATG AGGCTCTGCA CAACCACTAC ACGCAGAAGA
GCCTCTCCCT GTCTCCGGGT AAATGA
```

N-terminal sequencing of the CHO-cell produced material revealed a major sequence of -GRGEAE (SEQ ID NO: 11). Notably, other constructs reported in the literature begin with an -SGR . . . sequence.

Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

ActRIIb-Fc fusion proteins were also expressed in HEK293 cells and COS cells. Although material from all cell lines and reasonable culture conditions provided protein with muscle-building activity in vivo, variability in potency was observed perhaps relating to cell line selection and/or culture conditions.

Example 2

Generation of ActRIIb-Fc Mutants

Applicants generated a series of mutations in the extracellular domain of ActRIIB and produced these mutant proteins as soluble fusion proteins between extracellular ActRIIB and an Fc domain. The background ActRIIB-Fc fusion has the sequence (Fc portion underlined)

```
(SEQ ID NO: 12):
SGRGEAETRECIYYNANWELERTNQSGLERCEGEQDKRLHCYASWRNSSG

TIELVKKGCWLDDFNCYDRQECVATEENPQVYFCCCEGNFCNERFTHLPE

AGGPEVTYEPPPTAPTGGGTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPVPIEKTISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK
```

Various mutations, including N- and C-terminal truncations, were introduced into the background ActRIIB-Fc protein. Based on the data presented in Example 1, it is expected that these constructs, if expressed with a TPA leader, will lack the N-terminal serine. Mutations were generated in ActRIIB extracellular domain by PCR mutagenesis. After PCR, fragments were purified through a Qiagen column, digested with SfoI and AgeI and gel purified. These fragments were ligated into expression vector pAID4 (see WO2006/012627) such that upon ligation it created fusion chimera with human IgG1. Upon transformation into *E. coli* DH5 alpha, colonies were picked and DNAs were isolated. For murine constructs (mFc), a murine IgG2a was substituted for the human IgG1. All mutants were sequence verified.

All of the mutants were produced in HEK293T cells by transient transfection. In summary, in a 500 ml spinner, HEK293T cells were set up at $6\times10^5$ cells/ml in Freestyle (Invitrogen) media in 250 ml volume and grown overnight. Next day, these cells were treated with DNA:PEI (1:1) complex at 0.5 ug/ml final DNA concentration. After 4 hrs, 250 ml media was added and cells were grown for 7 days. Conditioned media was harvested by spinning down the cells and concentrated.

Mutants were purified using a variety of techniques, including, for example, protein A column and eluted with low pH (3.0) glycine buffer. After neutralization, these were dialyzed against PBS.

Mutants were also produced in CHO cells by similar methodology.

Mutants were tested in binding assays and/or bioassays. In some instances, assays were performed with conditioned medium rather than purified proteins.

Example 3

Generation of Truncated Variant ActRIIB(25-131)-hFc

Applicants generated a truncated fusion protein, ActRIIB (25-131)-hFc (FIGS. 7-8), which exhibits effects on muscle that are similar to those observed with ActRIIB(20-134)-hFc (while exhibiting superior effects on other tissues and parameters). ActRIIB(25-131)-hFc was generated using the same leader and methodology as described above with respect to ActRIIB(20-134)-hFc. The mature ActRIIB(25-131)-hFc protein purified after expression in CHO cells has the sequence shown below (SEQ ID NO: 23). Amino acids 1-107 (underlined) are derived from ActRIIB.

```
                                    (SEQ ID NO: 23)
ETRECIYYNA NWELERTNQS GLERCEGEQD KRLHCYASWR

NSSGTIELVK KGCWLDDFNC YDRQECVATE ENPQVYFCCC

EGNFCNERFT HLPEAGGPEV TYEPPPTGGG THTCPPCPAP

ELLGGPSVFL FPPKPKDTLM ISRTPEVTCV VVDVSHEDPE

VKFNWYVDGV EVHNAKTKPR EEQYNSTYRV VSVLTVLHQD

WLNGKEYKCK VSNKALPAPI EKTISKAKGQ PREPQVYTLP

PSREEMTKNQ VSLTCLVKGF YPSDIAVEWE SNGQPENNYK

TTPPVLDSDG SFFLYSKLTV DKSRWQQGNV FSCSVMHEAL

HNHYTQKSLS LSPGK
```

The expressed molecule was purified using a series of column chromatography steps, including for example, three or more of the following, in any order: Protein A chromatography, Q sepharose chromatography, phenylsepharose chromatography, size exclusion chromatography and cation exchange chromatography. The purification could be completed with viral filtration and buffer exchange.

Example 4

High-Affinity Ligand Binding by ActRIIB(25-131)-hFc

Affinities of several ligands for ActRIIB(25-131)-hFc and its full-length counterpart ActRIIB(20-134)-hFc were evaluated in vitro with a Biacore™ instrument, and the results are summarized in the table below. Kd values were obtained by steady-state affinity fit due to very rapid association and dissociation of the complex, which prevented accurate determination of $k_{on}$ and $k_{off}$. ActRIIB(25-131)-hFc bound activin A, activin B, and GDF11 with high affinity. Intriguingly, ActRIIB(25-131)-hFc appears to show a higher affinity for GDF3 than ActRIIB(20-134)-hFc (data not shown).

Ligand Affinities of ActRIIB-hFc Forms:

| Fusion Construct | Activin A (e-11) | Activin B (e-11) | GDF11 (e-11) |
|---|---|---|---|
| ActRIIB(20-134)-hFc | 1.6 | 1.2 | 3.6 |
| ActRIIB(25-131)-hFc | 1.8 | 1.2 | 3.1 |

Example 5

Bioassay for GDF-11 and Activin-Mediated Signaling

An A-204 Reporter Gene Assay was used to evaluate the effects of ActRIIB-Fc proteins on signaling by GDF-11 and Activin A. Cell line: Human Rhabdomyosarcoma (derived from muscle). Reporter vector: pGL3(CAGA)12 (Described in Dennler et al, 1998, EMBO 17: 3091-3100.) See FIG. 5. The CAGA12 motif is present in TGF-Beta responsive genes (PAI-1 gene), so this vector is of general use for factors signaling through Smad2 and 3.

Day 1: Split A-204 cells into 48-well plate.

Day 2: A-204 cells transfected with 10 ug pGL3(CAGA)12 or pGL3(CAGA)12(10 ug)+pRLCMV (1 ug) and Fugene.

Day 3: Add factors (diluted into medium+0.1% BSA). Inhibitors need to be preincubated with Factors for 1 hr before adding to cells. 6 hrs later, cells rinsed with PBS, and lyse cells.

This is followed by a Luciferase assay. In the absence of any inhibitors, Activin A showed 10 fold stimulation of reporter gene expression and an ED50~2 ng/ml. GDF-11: 16 fold stimulation, ED50~1.5 ng/ml.

ActRIIB(R64, 20-134) is a potent inhibitor of activin, GDF-8 and GDF-11 activity in this assay. Variants were tested in this assay as well.

Example 6

GDF-11 Inhibition by N-Terminal and C-Terminal Truncations

Truncations at the N-terminus and C-terminus of the ActRIIB portion ActRIIB-Fc (R64, 20-134) were generated and tested for activity as inhibitors of GDF-11 and activin. The activities are shown below (as measured in conditioned media):

C-Terminal ActRIIb-hFc Truncations:

| | IC50 (ng/mL) | |
|---|---|---|
| | GDF-11 | Activin |
| ActRIIb-hFc (R64, 20-134) | 45 | 22 |
| ActRIIb-hFc (R64, 20-132) | 87 | 32 |
| ActRIIb-hFc (R64, 20-131) | 120 | 44 |
| ActRIIb-hFc (R64, 20-128) | 130 | 158 |

As can be seen, truncations of three (ending with . . . PPT), six (ending with . . . YEP) or more amino acids at the C-terminus causes a threefold or greater decrease in the activity of the molecule. The truncation of the final 15 amino acids of the ActRIIB portion causes a greater loss of activity (see WO2006/012627).

Amino terminal truncations were made in the background of an ActRIIb-hFc (R64 20-131) protein. The activities are shown below (as measured in conditioned media):

N-Terminal ActRIIb-hFc Truncations:

| | IC50 (ng/mL) | |
|---|---|---|
| | GDF-11 | Activin |
| ActRIIb-hFc (R64, 20-131) (GRG . . . ) | 183 | 201 |
| ActRIIb-hFc (R64, 21-131) (RGE . . . ) | 121 | 325 |
| ActRIIb-hFc (R64, 22-131) (GEA . . . ) | 71 | 100 |
| ActRIIb-hFc (R64, 23-131) (EAE . . . ) | 60 | 43 |
| ActRIIb-hFc (R64, 24-131) (AET . . . ) | 69 | 105 |

Accordingly, truncations of two, three or four amino acids from the N-terminus lead to the production of a more active protein than the versions with a full-length extracellular domain. Additional experiments show that a truncation of five amino acids, ActRIIb-hFc (R64, 25-131) has activity equivalent to the untruncated form, and additional deletions at the N-terminus continue to degrade the activity of the protein. Therefore, optimal constructs will have a C-terminus ending between amino acid 133-134 of SEQ ID NO:4 and an N-terminus beginning at amino acids 22-24 of SEQ ID NO:4. An N-terminus corresponding to amino acids 21 or 25 will give activity that is similar to the ActRIIb-hFc (R64, 20-134) construct, although the protein designated as SEQ ID NO: 23 has been characterized as having superior effects in some regards.

Example 7

ActRIIb-Fc Variants, Cell-Based Activity

Activity of ActRIIB-Fc proteins was tested in a cell based assay, as described above. Results are summarized in Table 1, below. Some variants were tested in different C-terminal truncation constructs. As discussed above, truncations of five or fifteen amino acids caused reduction in activity. Remarkably, the L79D and L79E variants showed substantial loss of activin binding while retaining almost wild-type inhibition of GDF-11.

Soluble ActRIIB-Fc Binding to GDF11 and Activin A:

| ActRIIB-Fc Variations | Portion of ActRIIB (corresponds to amino acids of SEQ ID NO: 4) | GDF11 Inhibition Activity | Activin Inhibition Activity |
|---|---|---|---|
| 64R | 20-134 | +++ (approx. $10^{-8}$ M $K_I$) | +++ (approx. $10^{-8}$ M $K_I$) |
| 64A | 20-134 | + (approx. $10^{-6}$ M $K_I$) | + (approx. $10^{-6}$ M $K_I$) |
| 64R | 20-129 | +++ | +++ |
| 64R K74A | 20-134 | ++++ | ++++ |
| 64R A24N | 20-134 | +++ | +++ |
| 64R A24N | 20-119 | ++ | ++ |
| 64R A24N K74A | 20-119 | + | + |
| R64 L79P | 20-134 | + | + |
| R64 L79P K74A | 20-134 | + | + |
| R64 L79D | 20-134 | +++ | + |
| R64 L79E | 20-134 | +++ | + |
| R64K | 20-134 | +++ | +++ |
| R64K | 20-129 | +++ | +++ |
| R64 P129S P130A | 20-134 | +++ | +++ |
| R64N | 20-134 | + | + |

\+ Poor activity (roughly $1 \times 10^{-6}$ $K_I$)
++ Moderate activity (roughly $1 \times 10^{-7}$ $K_I$)
+++ Good (wild-type) activity (roughly $1 \times 10^{-8}$ $K_I$)
++++ Greater than wild-type activity Example 8

GDF-11 and Activin A Binding

Binding of certain ActRIIB-Fc proteins to ligands was tested in a BiaCore™ assay.

The ActRIIB-Fc variants or wild-type protein were captured onto the system using an anti-hFc antibody. Ligands were injected and flowed over the captured receptor proteins. Results are summarized in tables, below.
Ligand Binding Specificity IIB Variants.

| Protein | GDF11 | | |
|---|---|---|---|
| | Kon (1/Ms) | Koff (1/s) | KD (M) |
| ActRIIB-hFc (R64 20-134) | 1.34e−6 | 1.13e−4 | 8.42e−11 |
| ActRIIB-hFc (R64, A24N 20-134) | 1.21e−6 | 6.35e−5 | 5.19e−11 |
| ActRIIB-hFc (R64, L79D 20-134) | 6.7e−5 | 4.39e−4 | 6.55e−10 |
| ActRIIB-hFc (R64, L79E 20-134) | 3.8e−5 | 2.74e−4 | 7.16e−10 |
| ActRIIB-hFc (R64K 20-134) | 6.77e−5 | 2.41e−5 | 3.56e−11 |

| Protein | GDF8 | | |
|---|---|---|---|
| | Kon (1/Ms) | Koff (1/s) | KD (M) |
| ActRIIB-hFc (R64 20-134) | 3.69e−5 | 3.45e−5 | 9.35e−11 |
| ActRIIB-hFc (R64, A24N 20-134) | | | |
| ActRIIB-hFc (R64, L79D 20-134) | 3.85e−5 | 8.3e−4 | 2.15e−9 |
| ActRIIB-hFc (R64, L79E 20-134) | 3.74e−5 | 9e−4 | 2.41e−9 |
| ActRIIB-hFc (R64K 20-134) | 2.25e−5 | 4.71e−5 | 2.1e−10 |
| ActRIIB-hFc (R64K 20-129) | 9.74e−4 | 2.09e−4 | 2.15e−9 |
| ActRIIB-hFc (R64, P129S, P130R 20-134) | 1.08e−5 | 1.8e−4 | 1.67e−9 |
| ActRIIB-hFc (R64, K74A 20-134) | 2.8e−5 | 2.03e−5 | 7.18e−11 |

| Protein | ActivinA | | |
|---|---|---|---|
| | Kon (1/Ms) | Koff (1/s) | KD (M) |
| ActRIIB-hFc (R64 20-134) | 5.94e6 | 1.59e−4 | 2.68e−11 |
| ActRIIB-hFc (R64, A24N 20-134) | 3.34e6 | 3.46e−4 | 1.04e−10 |
| ActRIIB-hFc (R64, L79D 20-134) | | | Low binding |
| ActRIIB-hFc (R64, L79E 20-134) | | | Low binding |
| ActRIIB-hFc (R64K 20-134) | 6.82e6 | 3.25e−4 | 4.76e−11 |
| ActRIIB-hFc (R64K 20-129) | 7.46e6 | 6.28e−4 | 8.41e−11 |
| ActRIIB-hFc (R64, P129S, P130R 20-134) | 5.02e6 | 4.17e−4 | 8.31e−11 |

Other variants have been generated and tested, as reported in WO2006/012627, using ligands coupled to the device and flowing receptor over the coupled ligands. A table of data with respect to these variants is reproduced below:
Soluble ActRIIB-Fc Variants Binding to Gdf11 and Activin A (Biacore Assay)

| ActRIIB | ActA | GDF11 |
|---|---|---|
| WT (64A) | KD = 1 .8e−7M (+) | KD = 2.6e−7M (+) |
| WT (64R) | na | KD = 8.6e−8M (+++) |
| +15tail | KD~2.6e−8M (+++) | KD = 1.9e−8M (++++) |

-continued

| ActRIIB | ActA | GDF11 |
|---|---|---|
| E37A | * | * |
| R40A | – | – |
| D54A | – | * |
| K55A | ++ | * |
| R56A | * | * |
| K74A | KD = 4.35e−9M +++++ | KD = 5.3e−9M +++++ |
| K74Y | * | -- |
| K74F | * | -- |
| K74I | * | -- |
| W78A | * | * |
| L79A | + | * |
| D80K | * | * |
| D80R | * | * |
| D80A | * | * |
| D80F | * | * |
| D80G | * | * |
| D80M | * | * |
| D80N | * | * |
| D80I | * | – |
| F82A | ++ | – |

* No observed binding
-- <1/5 WT binding
– ~1/2 WT binding
\+ WT
++ <2x increased binding
+++ ~5x increased binding
++++ ~10x increased binding
+++++ ~40x increased binding Example 9

Effect of ActRIIB-Fc on Bone Loss and Adiposity Caused by Orchidectomy

Androgen-deprivation therapy, most prominently used in the treatment of prostate cancer, can cause pathological loss of muscle and bone, as well as enlargement of adipose tissue. Applicants investigated effects of ActRIIB-Fc in the orchidectomized (ORX) mouse, an animal model which mimics many of the changes associated with androgen deprivation. Nine-week-old C57BL/6 mice were ORX or sham-operated, and ten days later treatment was initiated with ActRIIB(R64 20-134)-mFc or Tris-buffered-saline (TBS) vehicle (n=10 per group) twice per week at 10 mg/kg, i.p., for a period of 10 weeks (71 days).

Figure 10:
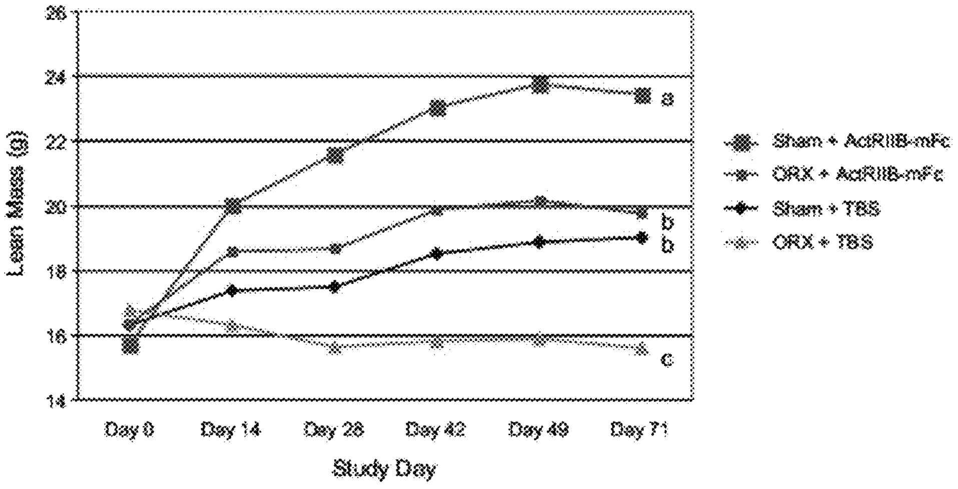
FIG. 10 shows lean body mass vs. time in mice as a function of ORX and ActRIIB(R64 20-134)-mFc treatment. Lean body mass (total nonfat mass) was determined by NMR. Data shown are means (n=10 per group), and Day 71 means that differ significantly (P<0.05, two-tailed unpaired t-test) are designated by different letters. Unlike ORX controls, ORX mice treated with ActRIIB(R64 20-134)-mFc gained lean body mass over the course of the experiment, finishing with values approximately 25% higher than in the former group. A similar increase in lean body mass was also observed under gonad-intact conditions for ActRIIB(R64 20-134)-mFc compared to vehicle.
Figure 11:
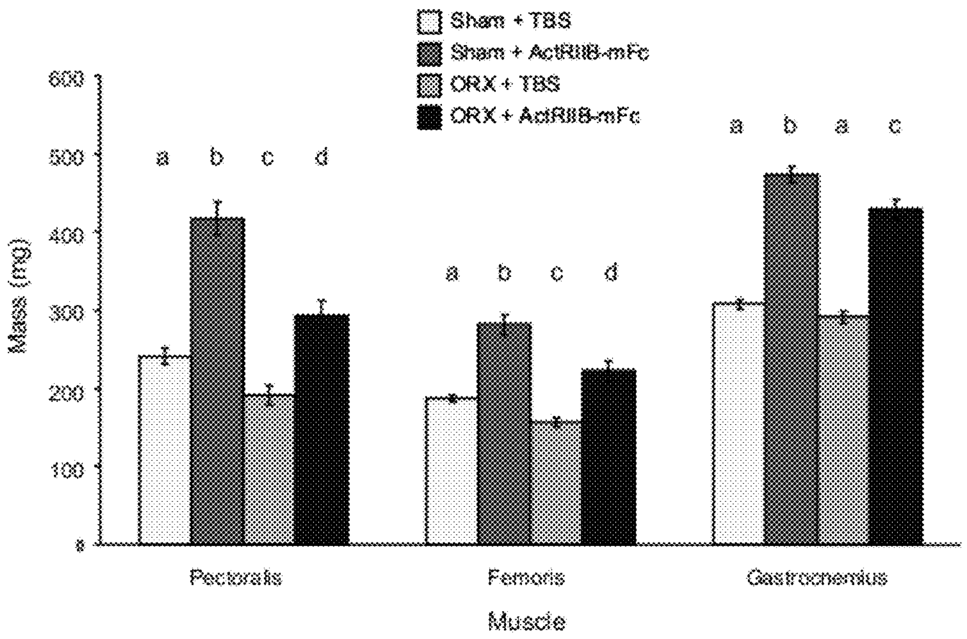
FIG. 11 shows skeletal muscle mass in mice as a function of ORX and ActRIIB(R64 20-134)-mFc treatment for 71 days. Pectoralis, rectus femoris, and gastrocnemius muscles were surgically removed and weighed at study completion. Data shown are means±SEM (n=10 per group), and those that differ significantly (P<0.05, two-tailed unpaired t-test) are designated by different letters. ActRIIB(R64 20-134)-mFc increased the mass of all three muscles significantly under both ORX and gonad-intact conditions.

In this experiment, ActRIIB-mFc treatment increased body weight as the net effect of beneficial changes in muscle mass, bone mass, and fat mass. As shown in FIG. 9, ActRIIB-mFc increased the rate of body weight gain, compared to controls, under ORX conditions as well as gonad-intact conditions. This effect was due to a pronounced increase in lean body mass. Whereas ORX controls showed a slight decline in lean body mass over 10 weeks, ORX mice treated with ActRIIB-mFc displayed a marked increase in lean body mass, reaching a mean value 25% higher than controls at study completion (FIG. 10). A similar increase was observed under gonad-intact conditions for ActRIIB-mFc compared to vehicle (FIG. 10). Part of this increase in lean body mass was due to a stimulatory effect of ActRIIB-mFc on muscle mass under both ORX conditions and gonad-intact conditions, as exemplified by three different skeletal muscles (FIG. 11).

Figure 12:
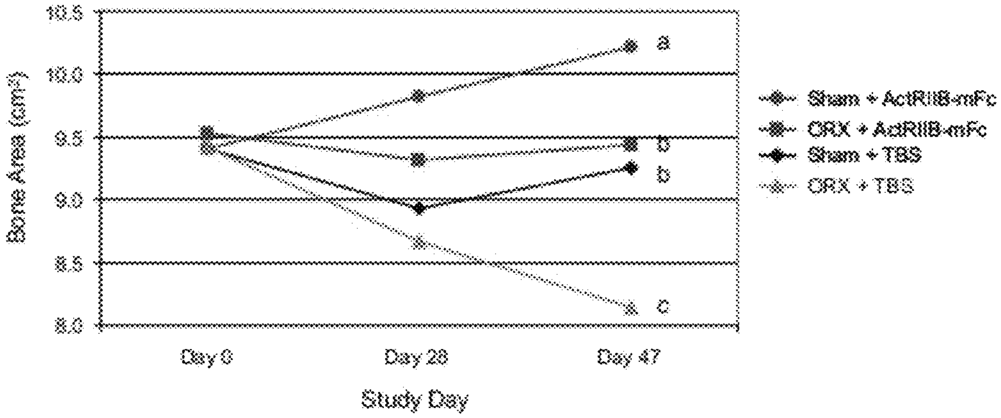
FIG. 12 shows whole-body bone area vs. time in mice as a function of ORX and ActRIIB(R64 20-134)-mFc treatment. Measurements were made by dual energy X-ray absorptiometry (DEXA). Data shown are means (n=10 per group), and Day 47 means that differ significantly (P<0.05, two-tailed unpaired t-test) are designated by different letters. ActRIIB (R64 20-134)-mFc prevented the progressive decrease in bone area observed under ORX conditions and led to significantly increased bone area under gonad-intact conditions.
Figure 13:
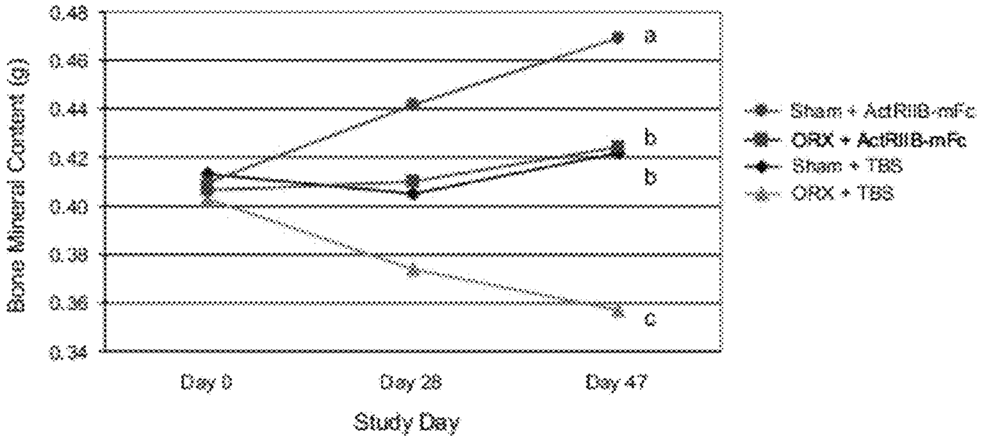
FIG. 13 shows whole-body bone mineral content vs. time in mice as a function of ORX and ActRIIB(R64 20-134)-mFc treatment. Measurements were made by dual energy X-ray absorptiometry (DEXA) analysis. Data shown are means (n=10 per group), and Day 47 means that differ significantly (P<0.05, two-tailed unpaired t-test) are designated by different letters. As with bone area, ActRIIB(R64 20-134)-mFc prevented the progressive decrease in bone mineral content observed under ORX conditions and led to significantly increased bone mineral content under gonad-intact conditions.
Figure 14:
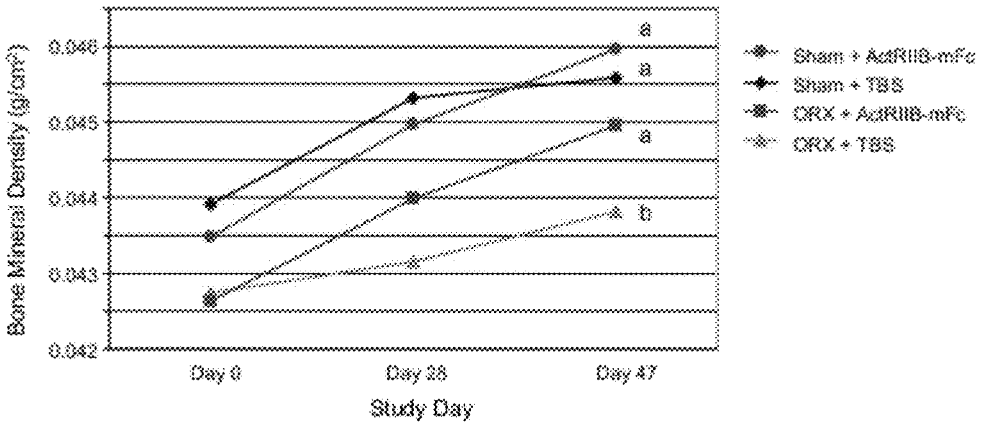
FIG. 14 shows whole-body bone mineral density vs. time in mice as a function of ORX and ActRIIB(R64 20-134)-mFc treatment. Measurements were made by dual energy X-ray absorptiometry (DEXA) analysis. Data shown are means (n=10 per group), and Day 47 means that differ significantly (P<0.05, two-tailed unpaired t-test) are designated by different letters. ActRIIB(R64 20-134)-mFc increased bone mineral density under ORX conditions but not gonad-intact conditions.
Figure 15:
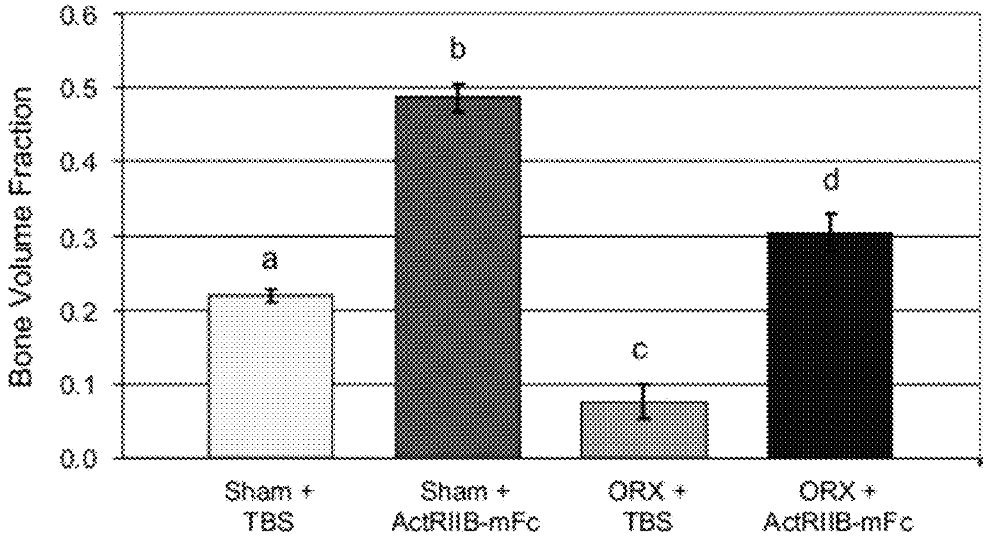
FIG. 15 shows bone volume fraction in murine tibia as a function of ORX and ActRIIB(R64 20-134)-mFc treatment for 71 days. Measurements were made by micro-computed tomography (micro-CT). Data shown are means±SEM (n=7 per group), and those that differ significantly (P<0.05, two-tailed unpaired t-test) are designated by different letters. In ORX mice, ActRIIB(R64 20-134)-mFc increased bone volume fraction markedly compared to vehicle, restoring this endpoint to levels typical in gonad-intact mice treated with vehicle. ActRIIB(R64 20-134)-mFc increased this endpoint in gonad-intact mice by a similar magnitude.
Figure 16:
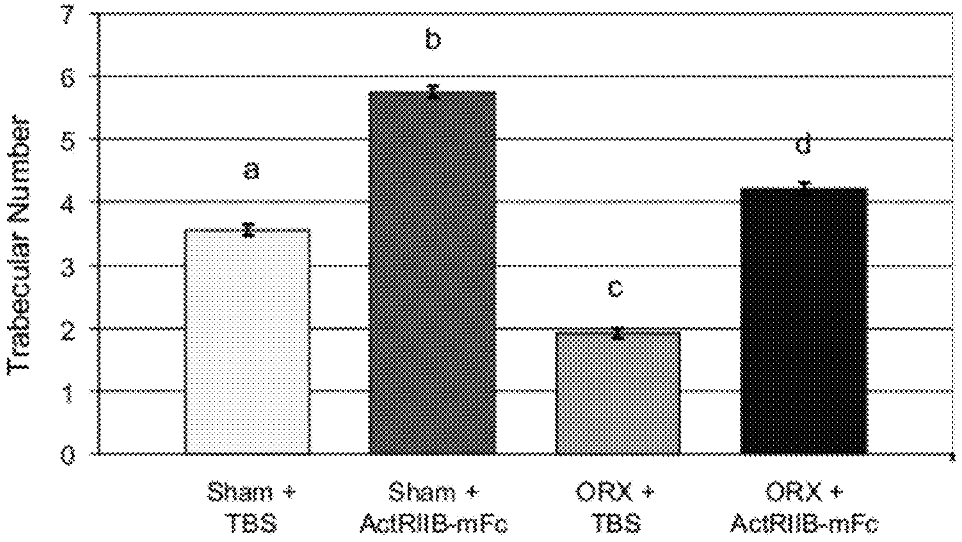
FIG. 16 shows trabecular number in murine tibia as a function of ORX and ActRIIB(R64 20-134)-mFc treatment for 71 days. Measurements were made by micro-CT and expressed as the mean number of trabeculae per mm (of randomly positioned line segments through the tissue). Data shown are means±SEM (n=7 per group), and those that differ significantly (P<0.05, two-tailed unpaired t-test) are designated by different letters. In ORX mice, ActRIIB(R64 20-134)-mFc doubled the trabecular number observed with vehicle, restoring this endpoint to levels typical in gonad-intact mice treated with vehicle. ActRIIB(R64 20-134)-mFc increased this endpoint in gonad-intact mice by a similar magnitude.
Figure 17:
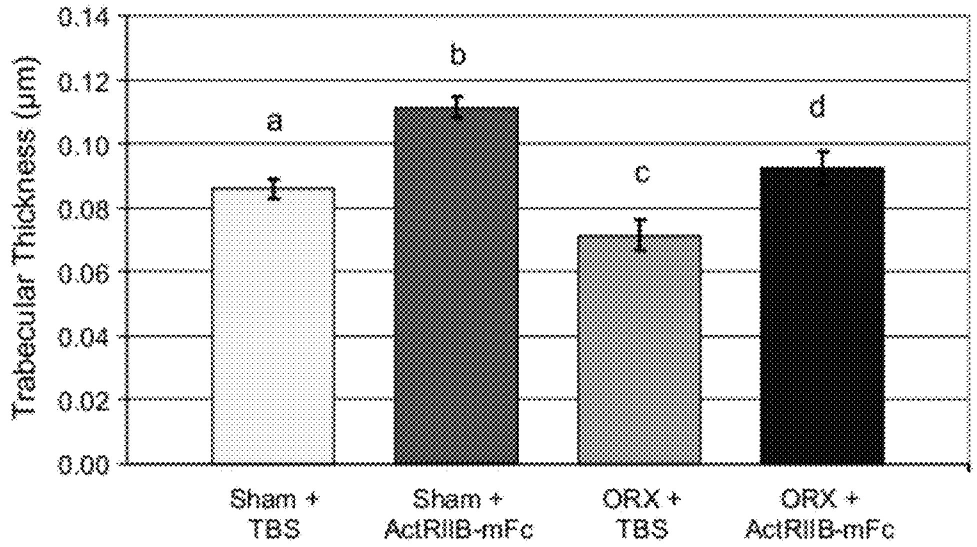
FIG. 17 shows trabecular thickness in murine tibia as a function of ORX and ActRIIB(R64 20-134)-mFc treatment for 71 days. Measurements were made by micro-CT. Data shown are means±SEM (n=7 per group), and those that differ significantly (P<0.05, two-tailed unpaired t-test) are designated by different letters. In ORX mice, ActRIIB(R64 20-134)-mFc increased trabecular thickness as compared with vehicle, restoring this endpoint to levels typical in gonad-intact mice treated with vehicle. ActRIIB(R64 20-134)-mFc increased this endpoint in gonad-intact mice by a similar percentage.
Figure 18:
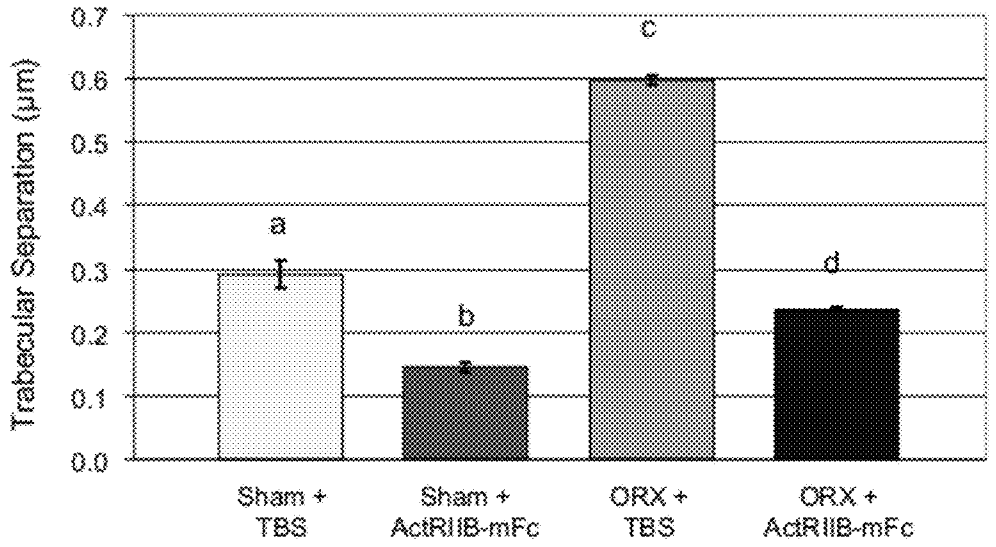
FIG. 18 shows trabecular separation in murine tibia as a function of ORX and ActRIIB(R64 20-134)-mFc treatment for 71 days. Measurements were made by micro-CT. Data shown are means±SEM (n=7 per group), and those that differ significantly (P<0.05, two-tailed unpaired t-test) are designated by different letters. In ORX mice, ActRIIB(R64 20-134)-mFc decreased trabecular separation as compared with vehicle, restoring this endpoint to levels typical in gonad-intact mice treated with vehicle. ActRIIB(R64 20-134)-mFc decreased this endpoint in gonad-intact mice by a similar percentage.
Figure 19:
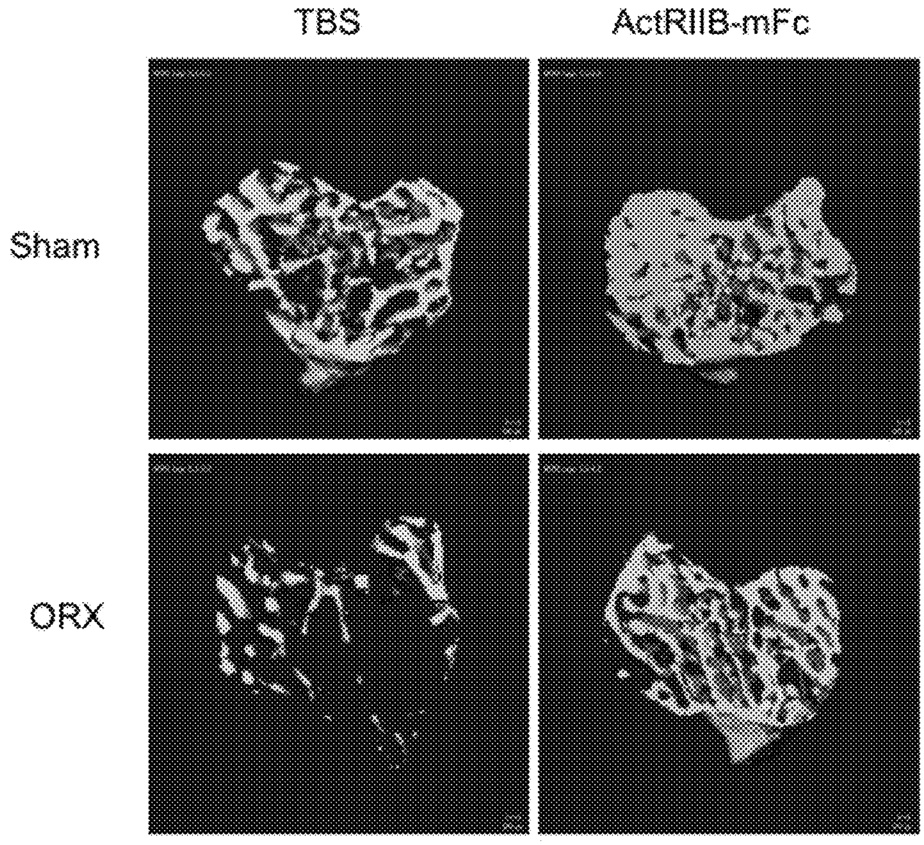
FIG. 19 shows tibial morphology in mice as a function of ORX and ActRIIB(R64 20-134)-mFc treatment for 71 days. Images of trabecular bone in the proximal tibia were obtained by micro-CT. Scale bar=100 μm. Tibial morphology in ORX mice treated with ActRIIB(R64 20-134)-mFc closely resembled that in vehicle-treated gonad-intact mice.

ActRIIB-mFc exerted a series of beneficial effects on bone. As determined by whole-body analysis with dual energy X-ray absorptiometry (DEXA), ActRIIB-mFc prevented progressive decreases in bone area and bone mineral content evident under ORX conditions and led to significantly increased bone area and bone mineral content under gonad-intact conditions (FIGS. 12, 13). ActRIIB-mFc also increased whole-body bone mineral density under ORX conditions (FIG. 14). Moreover, micro-CT analysis of trabecular bone in the proximal tibia revealed that ActRIIB-mFc treatment restored several bone parameters in ORX mice to levels observed in gonad-intact controls. With respect to ORX controls, these changes included: 1) a tripling of the bone volume fraction (FIG. 15), 2) a doubling of trabecular number (FIG. 16), 3) increased trabecular thickness (FIG. 17), and 4) reduced trabecular separation (FIG. 18). The similarity of tibial morphology in ORX mice treated with ActRIIB-mFc to that in gonad-intact controls is evident from images shown in FIG. 19. For each of the foregoing tibia-based endpoints, ActRIIB-mFc also produced changes in gonad-intact mice comparable in direction and magnitude to those in ORX mice (FIGS. 15-18).

Figure 20:
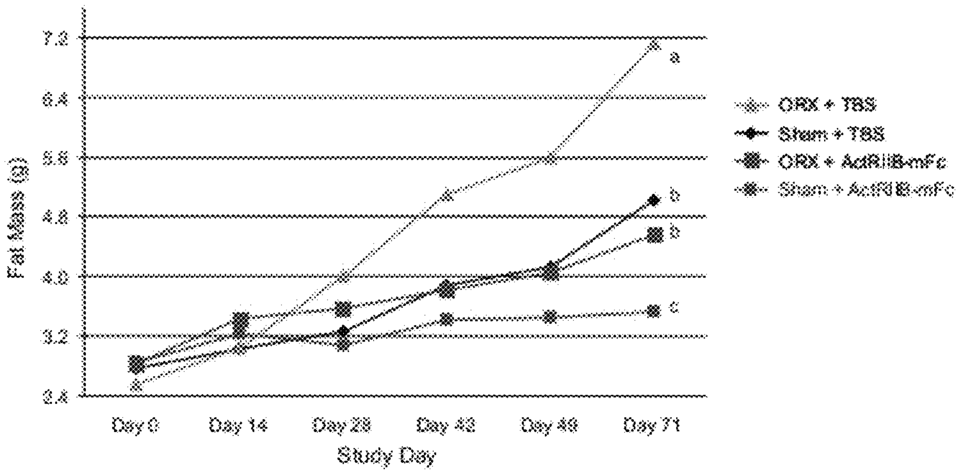
FIG. 20 shows fat tissue mass vs. time in mice as a function of ORX and ActRIIB(R64 20-134)-mFc treatment. Measurements were made by NMR. Data shown are means (n=10 per group), and Day 71 means that differ significantly (P<0.05, two-tailed unpaired t-test) are designated by different letters. Fat mass in vehicle-treated ORX mice tripled over the course of the study, and ActRIIB(R64 20-134)-mFc treatment in ORX mice cut this increase by more than 60%, restoring this endpoint to levels observed in gonad-intact controls. ActRIIB (R64 20-134)-mFc decreased this endpoint in gonad-intact mice by a similar percentage.
Figure 21:
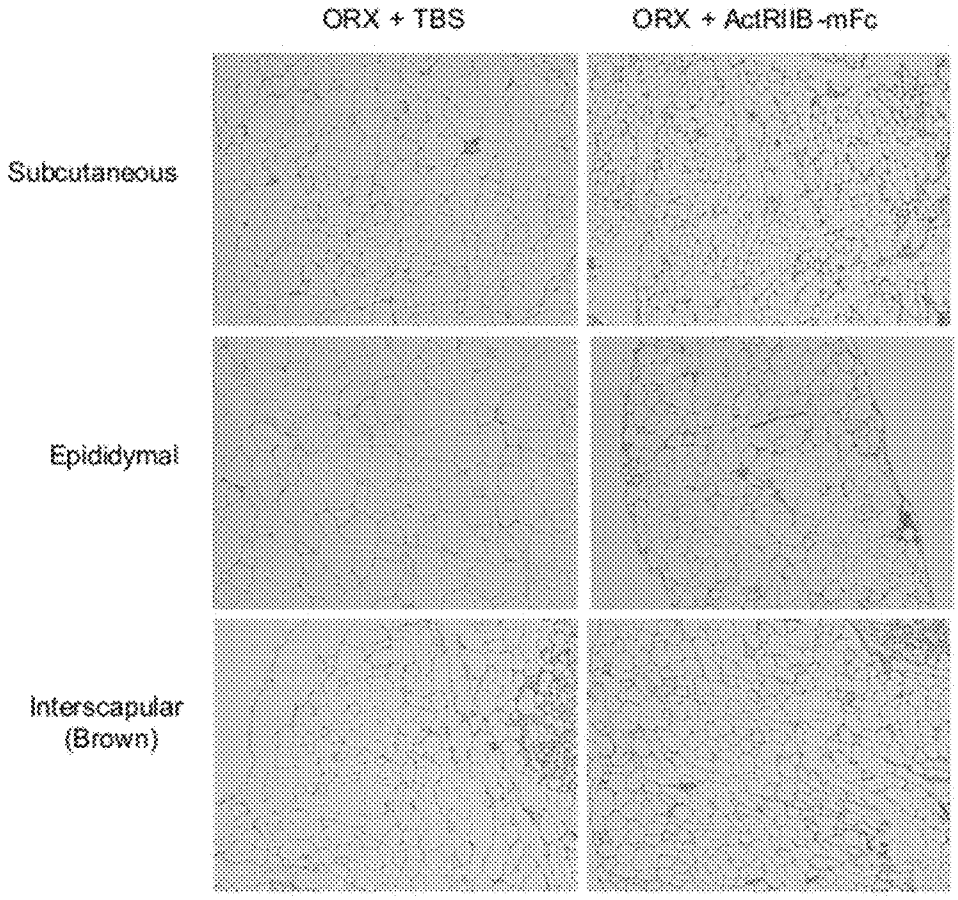
FIG. 21 shows adipocyte histology in ORX mice treated with vehicle (TBS) or ActRIIB(R64 20-134)-mFc for 71 days. Sections were stained with hematoxylin and eosin. Magnification=10×. ActRIIB-mFc reduced adipocyte size noticeably in subcutaneous and epididymal fat depots but not in interscapular brown fat.

ActRIIB-mFc also exerted beneficial effects on fat mass. As determined by NMR, total fat mass in ORX controls tripled over the course of the study. ActRIIB-mFc treatment in ORX mice cut this increase by more than 60%, restoring fat mass under ORX conditions to levels observed in gonad-intact controls (FIG. 20). ActRIIB-mFc also reduced the gain in fat mass observed in gonad-intact mice during the study. Consistent with these results, a histologic survey of fat depots indicated that ActRIIB-mFc reduced adipocyte size in subcutaneous and epididymal depots but not appreciably in interscapular brown fat (FIG. 21).

Figure 22:
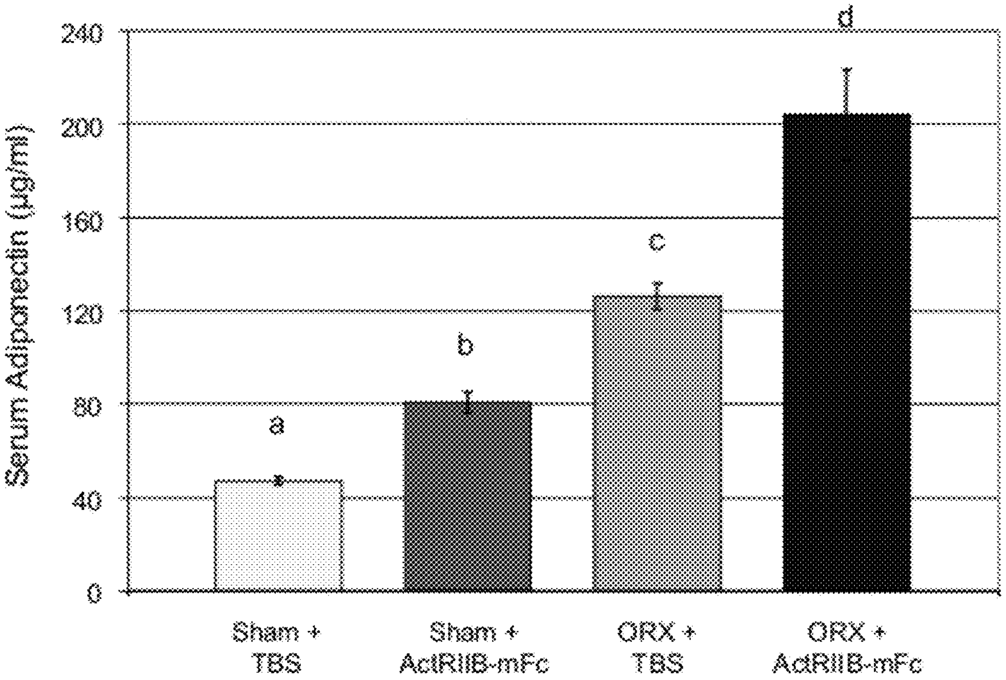
FIG. 22 shows serum adiponectin concentrations in mice as a function of ORX and ActRIIB(R64 20-134)-mFc treatment for 71 days. ELISA measurements detect all main oligomeric isoforms (total adiponectin). Data shown are means±SEM (n=10 per group), and those that differ significantly (P<0.05, two-tailed unpaired t-test) are designated by different letters. In both ORX and gonad-intact mice, ActRIIB(R64 20-134)-mFc increased circulating adiponectin concentrations significantly compared to their vehicle-treated counterparts.
Figure 23:
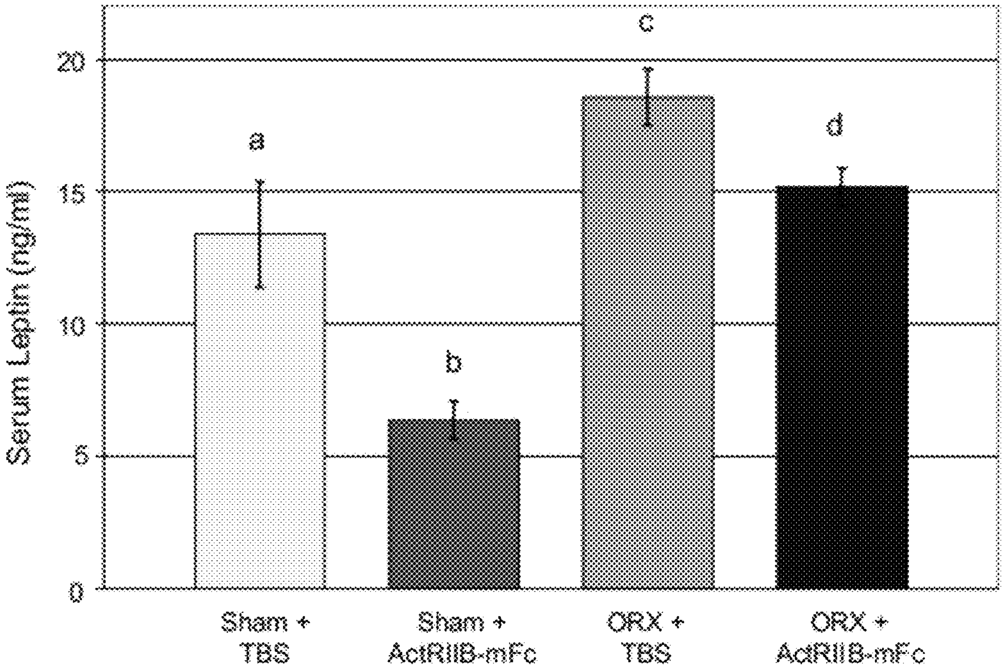
FIG. 23 shows serum leptin concentrations in mice as a function of ORX and ActRIIB(R64 20-134)-mFc treatment for 71 days. Data shown are means±SEM (n=10 per group), and those that differ significantly (P<0.05, two-tailed unpaired t-test) are designated by different letters. In both ORX and gonad-intact mice, ActRIIB(R64 20-134)-mFc reduced circulating leptin concentrations significantly compared to their vehicle-treated counterparts.

Finally, ActRIIB-mFc treatment altered circulating concentrations of adiponectin and leptin, endocrine molecules originating in adipose tissue (adipokines). There is general agreement that adiponectin is a key biomarker of body composition, as circulating adiponectin levels are known to vary inversely with fat mass/obesity, and adiponectin enhances insulin sensitivity in target tissues. Moreover, low adiponectin levels are associated with cardiovascular risk factors even in nonobese healthy individuals (Im et al., 2006, Metabolism 55:1546-1550). Thus, it is important that ActRIIB-mFc treatment increased serum adiponectin concentrations significantly in both ORX and gonad-intact mice compared to their vehicle-treated counterparts (FIG. 22). The higher adiponectin concentrations in ORX mice compared to their gonad-intact counterparts are consistent with the known inhibitory effect of androgen on adiponectin (Nishizawa et al., 2002, Diabetes 51:2734-2741). ActRIIB-mFc also reduced serum concentrations of leptin, another indicator of adipocyte status, in both ORX and gonad-intact mice compared to vehicle (FIG. 23).

Taken together, these data indicate that soluble ActRIIB-Fc chimeras can be used as antagonists of signaling by TGF-β family ligands in males to treat bone loss and increased adiposity arising from androgen deprivation and potentially other conditions as well.

Example 10

Figure 24:
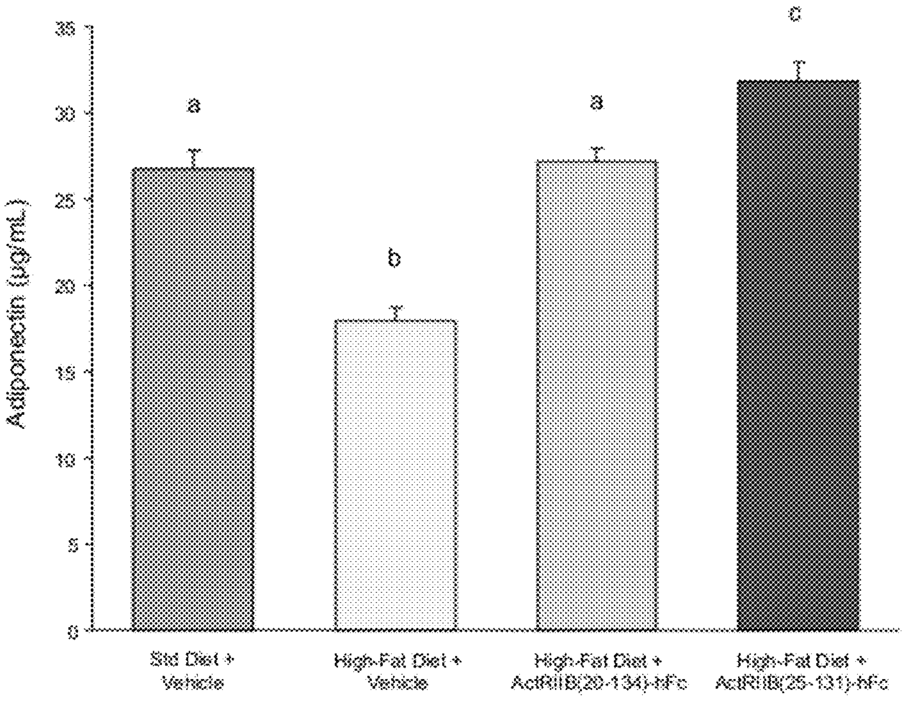
FIG. 24 shows serum levels of adiponectin in mice as a function of diet and ActRIIB-hFc treatment for 60 days. ELISA measurements detect all main oligomeric isoforms (total adiponectin), and data are means±SEM; n=7-10 per group; , p<0.01; *, p<0.001. In mice fed a high-fat diet, ActRIIB(20-134)-hFc increased circulating adiponectin concentrations by more than 50% to match those in standard-diet controls, while ActRIIB(25-131)-hFc increased circulating adiponectin concentrations by more than 75% to significantly exceed those in standard-diet controls.
Figure 25:
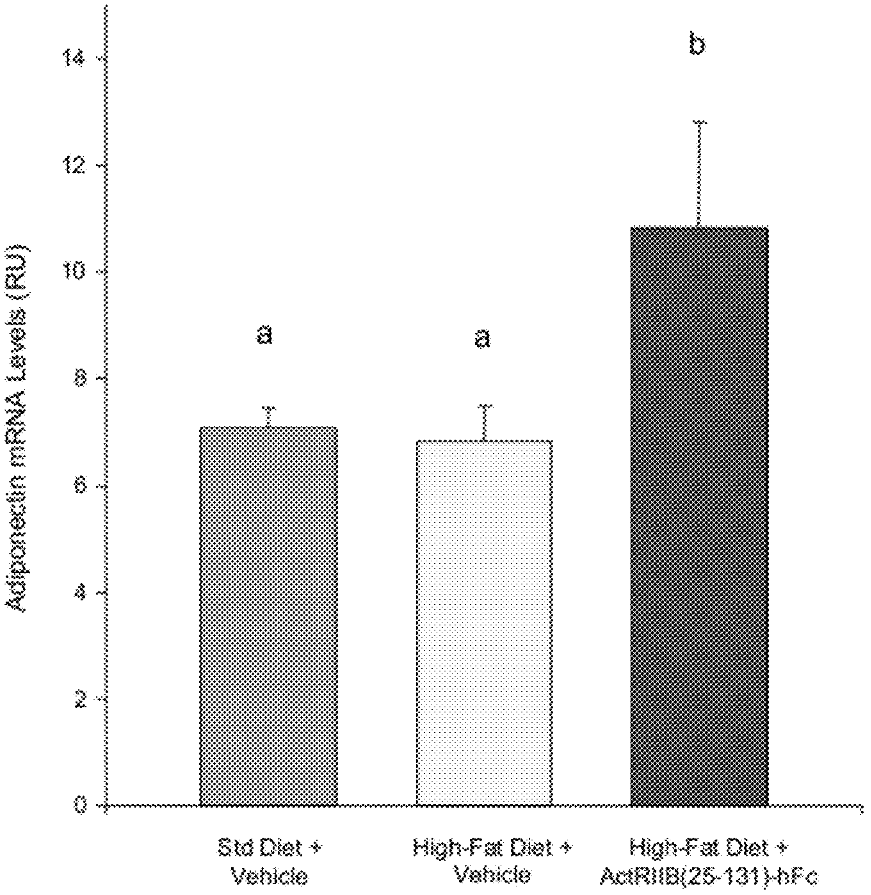
FIG. 25 shows levels of adiponectin mRNA in epididymal white fat of mice as a function of diet and ActRIIB(25-131)-hFc treatment for 60 days. RT-PCR data (in relative units, RU) are means±SEM; n=7 per group; *, p<0.05. In mice fed a high-fat diet, ActRIIB(25-131)-hFc increased adiponectin mRNA levels by more than 60%, thus contributing to elevated concentrations of circulating adiponectin in these mice.

Effect of ActRIIB-Fc Variants on Adiponectin Levels in Mice Fed a High-Fat Diet Applicants investigated the effects of ActRIIB(20-134)-hFc or ActRIIB(25-131)-hFc on circulating concentrations of adiponectin in male mice fed a high-fat diet. Ten-week-old C57BL/6 mice were weight-matched and treated subcutaneously with ActRIIB(20-134)-hFc (10 mg/kg), ActRIIB(25-131)-hFc (10 mg/kg), or Tris-buffered-saline (TBS) vehicle twice per week for 60 days. During this period, mice had unlimited access to a diet containing 58% fat instead of the standard chow containing 4.5% fat. An additional group of mice maintained on the standard chow diet was also treated with TBS vehicle and followed as a dietary control. By Day 60, ActRIIB(20-134)-hFc treatment increased serum adiponectin concentrations in mice fed the high-fat diet to approximately the same levels seen in mice fed the standard diet, while ActRIIB(25-131)-hFc treatment raised serum adiponectin concentrations significantly beyond these control levels (FIG. 24). Contributing to elevated adiponectin concentrations was an increase in adiponectin gene expression in white fat. Analysis of white adipose tissue by real-time polymerase chain reaction (RT-PCR) revealed that ActRIIB(25-131)-hFc increased adiponectin mRNA levels by more than 60% compared to high-fat diet controls (FIG. 25).

Taken together, these findings demonstrate that ActRIIB-Fc proteins can be used in vivo to increase adiponectin gene expression in white adipose tissue and to increase circulating adioponectin levels under a variety of physiological conditions.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for increasing adiponectin in a patient in need thereof, the method comprising administering an effective amount of an antibody, or antigen-binding fragment thereof, that specifically binds to an activin type IIB receptor (ActRIIB), and wherein the antibody, or antigen-binding fragment thereof, inhibits one or more of activin A, GDF8, and GDF11 from binding to the ActRIIB.

2. The method of claim 1, wherein the antibody, or antigen-binding fragment thereof, binds to a soluble ActRIIB peptide.

3. The method of claim 1, wherein the antibody, or antigen-binding fragment thereof, is monoclonal.

4. The method of claim 1, wherein the antibody, or antigen-binding fragment thereof, is chimeric.

5. The method claim 1, wherein the antibody, or antigen-binding fragment thereof, is humanized.

6. The method of claim 1, wherein the antibody, or antigen binding fragment thereof, is selected from: a single chain antibody, a bispecific antibody, a $F(ab)_2$ fragment, and a Fab' fragment.

7. The method of claim 1, wherein the patient has adiponectin deficiency or insufficiency.

8. The method of claim 1, wherein the patient has low circulating concentrations of adiponectin.

9. The method of claim 1, wherein administration of the antibody, or antigen-binding fragment thereof, increases adiponectin expression in adipocytes of the treated patient.

10. The method of claim 1, wherein the antibody, or antigen-binding fragment thereof, inhibits activin A from binding to the ActRIIB.

11. The method of claim 1, wherein the antibody, or antigen-binding fragment thereof, inhibits GDF8 from binding to the ActRIIB.

12. The method of claim 1, wherein the antibody, or antigen-binding fragment thereof, inhibits GDF11 from binding to the ActRIIB.

* * * * *

SEQUENCE LISTING

```
<160> NUMBER OF SEQ ID NOS: 34

<210> SEQ ID NO 1
<211> LENGTH: 116
<212> TYPE: PRT
<213> ORGANISM: Homo sapiens

<400> SEQUENCE: 1

Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30
```

```
Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr
        115


<210> SEQ ID NO 2
<211> LENGTH: 512
<212> TYPE: PRT
<213> ORGANISM: Homo sapiens

<400> SEQUENCE: 2

Met Thr Ala Pro Trp Val Ala Leu Ala Leu Leu Trp Gly Ser Leu Trp
1               5                   10                  15

Pro Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
    210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
```

-continued

```
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510


<210> SEQ ID NO 3
<211> LENGTH: 348
<212> TYPE: DNA
<213> ORGANISM: Homo sapiens

<400> SEQUENCE: 3

tctgggcgtg gggaggctga gacacgggag tgcatctact acaacgccaa ctgggagctg      60

gagcgcacca accagagcgg cctggagcgc tgcgaaggcg agcaggacaa gcggctgcac     120

tgctacgcct cctggcgcaa cagctctggc accatcgagc tcgtgaagaa gggctgctgg     180

ctagatgact tcaactgcta cgataggcag gagtgtgtgg ccactgagga gaacccccag     240

gtgtacttct gctgctgtga aggcaacttc tgcaacgagc gcttcactca tttgccagag     300

gctgggggcc cggaagtcac gtacgagcca cccccgacag cccccacc                  348


<210> SEQ ID NO 4
<211> LENGTH: 1539
<212> TYPE: DNA
<213> ORGANISM: Homo sapiens

<400> SEQUENCE: 4

atgacggcgc cctgggtggc cctcgccctc ctctggggat cgctgtggcc cggctctggg      60

cgtggggagg ctgagacacg ggagtgcatc tactacaacg ccaactggga gctggagcgc     120

accaaccaga gcggcctgga gcgctgcgaa ggcgagcagg acaagcggct gcactgctac     180

gcctcctggc gcaacagctc tggcaccatc gagctcgtga agaagggctg ctggctagat     240
```

-continued

```
gacttcaact gctacgatag gcaggagtgt gtggccactg aggagaaccc ccaggtgtac    300

ttctgctgct gtgaaggcaa cttctgcaac gagcgcttca ctcatttgcc agaggctggg    360

ggcccggaag tcacgtacga gccacccccg acagccccca ccctgctcac ggtgctggcc    420

tactcactgc tgcccatcgg gggcctttcc ctcatcgtcc tgctggcctt ttggatgtac    480

cggcatcgca agccccccta cggtcatgtg gacatccatg aggaccctgg gcctccacca    540

ccatcccctc tggtgggcct gaagccactg cagctgctgg agatcaaggc tcgggggcgc    600

tttggctgtg tctggaaggc ccagctcatg aatgactttg tagctgtcaa gatcttccca    660

ctccaggaca agcagtcgtg gcagagtgaa cgggagatct tcagcacacc tggcatgaag    720

cacgagaacc tgctacagtt cattgctgcc gagaagcgag gctccaacct cgaagtagag    780

ctgtggctca tcacggcctt ccatgacaag ggctccctca cggattacct caaggggaac    840

atcatcacat ggaacgaact gtgtcatgta gcagagacga tgtcacgagg cctctcatac    900

ctgcatgagg atgtgccctg gtgccgtggc gagggccaca agccgtctat tgcccacagg    960

gactttaaaa gtaagaatgt attgctgaag agcgacctca cagccgtgct ggctgacttt   1020

ggcttggctg ttcgatttga gccagggaaa cctccagggg acacccacgg acaggtaggc   1080

acgagacggt acatggctcc tgaggtgctc gagggagcca tcaacttcca gagagatgcc   1140

ttcctgcgca ttgacatgta tgccatgggg ttggtgctgt gggagcttgt gtctcgctgc   1200

aaggctgcag acggacccgt ggatgagtac atgctgccct ttgaggaaga gattggccag   1260

caccccttcgt tggaggagct gcaggaggtg gtggtgcaca agaagatgag gcccaccatt  1320

aaagatcact ggttgaaaca cccgggcctg gcccagcttt gtgtgaccat cgaggagtgc   1380

tgggaccatg atgcagaggc tcgcttgtcc gcgggctgtg tggaggagcg ggtgtccctg   1440

attcggaggt cggtcaacgg cactacctcg gactgtctcg tttccctggt gacctctgtc   1500

accaatgtgg acctgccccc taaagagtca agcatctaa                          1539
```

<210> SEQ ID NO 5
<211> LENGTH: 343
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125
```

```
Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Val Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340


<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Gly Gly Gly Gly
1               5


<210> SEQ ID NO 7
<211> LENGTH: 21
<212> TYPE: PRT
<213> ORGANISM: Apis sp.

<400> SEQUENCE: 7

Met Lys Phe Leu Val Asn Val Ala Leu Val Phe Met Val Val Tyr Ile
1               5                   10                  15

Ser Tyr Ile Tyr Ala
            20


<210> SEQ ID NO 8
<211> LENGTH: 22
<212> TYPE: PRT
<213> ORGANISM: Unknown
<220> FEATURE:
<223> OTHER INFORMATION: Description of Unknown:
      Tissue plasminogen activator
```

<400> SEQUENCE: 8

Met Asp Ala Met Lys Arg Gly Leu Cys Cys Val Leu Leu Leu Cys Gly
1               5                   10                  15

Ala Val Phe Val Ser Pro
            20

<210> SEQ ID NO 9
<211> LENGTH: 20
<212> TYPE: PRT
<213> ORGANISM: Homo sapiens

<400> SEQUENCE: 9

Met Gly Ala Ala Ala Lys Leu Ala Phe Ala Val Phe Leu Ile Ser Cys
1               5                   10                  15

Ser Ser Gly Ala
            20

<210> SEQ ID NO 10
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

| | | | | | |
|---|---|---|---|---|---|
| atggatgcaa | tgaagagagg | gctctgctgt | gtgctgctgc | tgtgtggagc | agtcttcgtt | 60 |
| tcgcccggcg | cctctgggcg | tggggaggct | gagacacggg | agtgcatcta | ctacaacgcc | 120 |
| aactgggagc | tggagcgcac | caaccagagc | ggcctggagc | gctgcgaagg | cgagcaggac | 180 |
| aagcggctgc | actgctacgc | ctcctggcgc | aacagctctg | gcaccatcga | gctcgtgaag | 240 |
| aagggctgct | ggctagatga | cttcaactgc | tacgataggc | aggagtgtgt | ggccactgag | 300 |
| gagaaccccc | aggtgtactt | ctgctgctgt | gaaggcaact | tctgcaacga | gcgcttcact | 360 |
| catttgccag | aggctggggg | cccggaagtc | acgtacgagc | accccccgac | agcccccacc | 420 |
| ggtggtggaa | ctcacacatg | cccaccgtgc | ccagcacctg | aactcctggg | gggaccgtca | 480 |
| gtcttcctct | tccccccaaa | acccaaggac | accctcatga | tctcccggac | ccctgaggtc | 540 |
| acatgcgtgg | tggtggacgt | gagccacgaa | gaccctgagg | tcaagttcaa | ctggtacgtg | 600 |
| gacggcgtgg | aggtgcataa | tgccaagaca | aagccgcggg | aggagcagta | caacagcacg | 660 |
| taccgtgtgg | tcagcgtcct | caccgtcctg | caccaggact | ggctgaatgg | caaggagtac | 720 |
| aagtgcaagg | tctccaacaa | agccctccca | gtccccatcg | agaaaaccat | ctccaaagcc | 780 |
| aaagggcagc | cccgagaacc | acaggtgtac | accctgcccc | catcccggga | ggagatgacc | 840 |
| aagaaccagg | tcagcctgac | ctgcctggtc | aaaggcttct | atcccagcga | catcgccgtg | 900 |
| gagtgggaga | gcaatgggca | gccggagaac | aactacaaga | ccacgcctcc | cgtgctggac | 960 |
| tccgacggct | ccttcttcct | ctatagcaag | ctcaccgtgg | acaagagcag | gtggcagcag | 1020 |
| gggaacgtct | tctcatgctc | cgtgatgcat | gaggctctgc | acaaccacta | cacgcagaag | 1080 |
| agcctctccc | tgtctccggg | taaatga | | | | 1107 |

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Gly Arg Gly Glu Ala Glu
1 5

<210> SEQ ID NO 12
<211> LENGTH: 344
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

```
Ser Gly Arg Gly Glu Ala Glu Thr Arg Glu Cys Ile Tyr Tyr Asn Ala
1               5                   10                  15

Asn Trp Glu Leu Glu Arg Thr Asn Gln Ser Gly Leu Glu Arg Cys Glu
            20                  25                  30

Gly Glu Gln Asp Lys Arg Leu His Cys Tyr Ala Ser Trp Arg Asn Ser
        35                  40                  45

Ser Gly Thr Ile Glu Leu Val Lys Lys Gly Cys Trp Leu Asp Asp Phe
    50                  55                  60

Asn Cys Tyr Asp Arg Gln Glu Cys Val Ala Thr Glu Glu Asn Pro Gln
65                  70                  75                  80

Val Tyr Phe Cys Cys Cys Glu Gly Asn Phe Cys Asn Glu Arg Phe Thr
                85                  90                  95

His Leu Pro Glu Ala Gly Gly Pro Glu Val Thr Tyr Glu Pro Pro Pro
            100                 105                 110

Thr Ala Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
```

```
                325                 330                 335

Ser Leu Ser Leu Ser Pro Gly Lys
            340


<210> SEQ ID NO 13
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 13

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Xaa His Tyr Thr Gln Lys Ser Leu Ser Leu Ser Pro Gly
    210                 215                 220

Lys
225


<210> SEQ ID NO 14
<211> LENGTH: 116
<212> TYPE: PRT
<213> ORGANISM: Homo sapiens
```

<400> SEQUENCE: 14

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr
        115

<210> SEQ ID NO 15
<211> LENGTH: 150
<212> TYPE: PRT
<213> ORGANISM: Rattus sp.

<400> SEQUENCE: 15

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 16
<211> LENGTH: 150
<212> TYPE: PRT
<213> ORGANISM: Sus sp.

<400> SEQUENCE: 16

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg

```
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 17
<211> LENGTH: 150
<212> TYPE: PRT
<213> ORGANISM: Mus sp.

<400> SEQUENCE: 17

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 18
<211> LENGTH: 150
<212> TYPE: PRT
<213> ORGANISM: Homo sapiens

<400> SEQUENCE: 18

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
```

```
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150


<210> SEQ ID NO 19
<211> LENGTH: 150
<212> TYPE: PRT
<213> ORGANISM: Unknown
<220> FEATURE:
<223> OTHER INFORMATION: Description of Unknown:
      Bovine IIb peptide

<400> SEQUENCE: 19

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Arg Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Val Gly Gly Leu Ser
145                 150


<210> SEQ ID NO 20
<211> LENGTH: 150
<212> TYPE: PRT
<213> ORGANISM: Xenopus sp.

<400> SEQUENCE: 20

Met Gly Ala Ser Val Ala Leu Thr Phe Leu Leu Leu Leu Ala Thr Phe
1               5                   10                  15

Arg Ala Gly Ser Gly His Asp Glu Val Glu Thr Arg Glu Cys Ile Tyr
            20                  25                  30

Tyr Asn Ala Asn Trp Glu Leu Glu Lys Thr Asn Gln Ser Gly Val Glu
        35                  40                  45

Arg Leu Val Glu Gly Lys Lys Asp Lys Arg Leu His Cys Tyr Ala Ser
```

50 55 60

Trp Arg Asn Asn Ser Gly Phe Ile Glu Leu Val Lys Lys Gly Cys Trp
65 70 75 80

Leu Asp Asp Phe Asn Cys Tyr Asp Arg Gln Glu Cys Ile Ala Lys Glu
85 90 95

Glu Asn Pro Gln Val Phe Phe Cys Cys Cys Glu Gly Asn Tyr Cys Asn
100 105 110

Lys Lys Phe Thr His Leu Pro Glu Val Glu Thr Phe Asp Pro Lys Pro
115 120 125

Gln Pro Ser Ala Ser Val Leu Asn Ile Leu Ile Tyr Ser Leu Leu Pro
130 135 140

Ile Val Gly Leu Ser Met
145 150

<210> SEQ ID NO 21
<211> LENGTH: 150
<212> TYPE: PRT
<213> ORGANISM: Homo sapiens

<400> SEQUENCE: 21

Met Gly Ala Ala Ala Lys Leu Ala Phe Ala Val Phe Leu Ile Ser Cys
1 5 10 15

Ser Ser Gly Ala Ile Leu Gly Arg Ser Glu Thr Gln Glu Cys Leu Phe
20 25 30

Phe Asn Ala Asn Trp Glu Lys Asp Arg Thr Asn Gln Thr Gly Val Glu
35 40 45

Pro Cys Tyr Gly Asp Lys Asp Lys Arg Arg His Cys Phe Ala Thr Trp
50 55 60

Lys Asn Ile Ser Gly Ser Ile Glu Ile Val Lys Gln Gly Cys Trp Leu
65 70 75 80

Asp Asp Ile Asn Cys Tyr Asp Arg Thr Asp Cys Val Glu Lys Lys Asp
85 90 95

Ser Pro Glu Val Tyr Phe Cys Cys Cys Glu Gly Asn Met Cys Asn Glu
100 105 110

Lys Phe Ser Tyr Phe Pro Glu Met Glu Val Thr Gln Pro Thr Ser Asn
115 120 125

Pro Val Thr Pro Lys Pro Pro Tyr Tyr Asn Ile Leu Leu Tyr Ser Leu
130 135 140

Val Pro Leu Met Leu Ile
145 150

<210> SEQ ID NO 22
<211> LENGTH: 154
<212> TYPE: PRT
<213> ORGANISM: Artificial Sequence
<220> FEATURE:
<223> OTHER INFORMATION: Description of Artificial Sequence: Synthetic
Consensus sequence
<220> FEATURE:
<221> NAME/KEY: MOD_RES
<222> LOCATION: (8)..(8)
<223> OTHER INFORMATION: Any amino acid
<220> FEATURE:
<221> NAME/KEY: MOD_RES
<222> LOCATION: (121)..(121)
<223> OTHER INFORMATION: Any amino acid

<400> SEQUENCE: 22

Met Thr Ala Pro Trp Ala Ala Xaa Leu Ala Leu Leu Trp Gly Ser Leu
1 5 10 15

```
Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Leu Cys Glu Gly Glu Gln Asp Lys Arg Leu His Cys Tyr Ala Ser
    50                  55                  60

Trp Arg Asn Ser Ser Gly Thr Ile Glu Leu Val Lys Lys Gly Cys Trp
65                  70                  75                  80

Leu Asp Asp Phe Asn Cys Tyr Asp Arg Gln Glu Cys Val Ala Thr Glu
                85                  90                  95

Glu Asn Pro Gln Val Tyr Phe Cys Cys Cys Glu Gly Asn Phe Cys Asn
            100                 105                 110

Glu Arg Phe Thr His Leu Pro Glu Xaa Gly Gly Pro Glu Val Thr Tyr
        115                 120                 125

Glu Pro Lys Pro Pro Thr Ala Pro Thr Leu Leu Thr Val Leu Ala Tyr
    130                 135                 140

Ser Leu Leu Pro Ile Gly Gly Leu Ser Met
145                 150


<210> SEQ ID NO 23
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Thr Arg Glu Cys Ile Tyr Tyr Asn Ala Asn Trp Glu Leu Glu Arg
1               5                   10                  15

Thr Asn Gln Ser Gly Leu Glu Arg Cys Glu Gly Glu Gln Asp Lys Arg
            20                  25                  30

Leu His Cys Tyr Ala Ser Trp Arg Asn Ser Ser Gly Thr Ile Glu Leu
        35                  40                  45

Val Lys Lys Gly Cys Trp Leu Asp Asp Phe Asn Cys Tyr Asp Arg Gln
    50                  55                  60

Glu Cys Val Ala Thr Glu Glu Asn Pro Gln Val Tyr Phe Cys Cys Cys
65                  70                  75                  80

Glu Gly Asn Phe Cys Asn Glu Arg Phe Thr His Leu Pro Glu Ala Gly
                85                  90                  95

Gly Pro Glu Val Thr Tyr Glu Pro Pro Pro Thr Gly Gly Gly Thr His
            100                 105                 110

Thr Cys Pro Pro Cys Pro Ala Pro Glu Leu Leu Gly Gly Pro Ser Val
        115                 120                 125

Phe Leu Phe Pro Pro Lys Pro Lys Asp Thr Leu Met Ile Ser Arg Thr
    130                 135                 140

Pro Glu Val Thr Cys Val Val Val Asp Val Ser His Glu Asp Pro Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
```

```
    210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335


<210> SEQ ID NO 24
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Asp Ala Met Lys Arg Gly Leu Cys Cys Val Leu Leu Leu Cys Gly
1               5                   10                  15

Ala Val Phe Val Ser Pro Gly Ala Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Cys Glu Gly Glu Gln Asp Lys Arg Leu His Cys Tyr Ala Ser Trp
    50                  55                  60

Arg Asn Ser Ser Gly Thr Ile Glu Leu Val Lys Lys Gly Cys Trp Leu
65                  70                  75                  80

Asp Asp Phe Asn Cys Tyr Asp Arg Gln Glu Cys Val Ala Thr Glu Glu
                85                  90                  95

Asn Pro Gln Val Tyr Phe Cys Cys Cys Glu Gly Asn Phe Cys Asn Glu
            100                 105                 110

Arg Phe Thr His Leu Pro Glu Ala Gly Gly Pro Glu Val Thr Tyr Glu
        115                 120                 125

Pro Pro Pro Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240
```

```
Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Glu Glu Met Thr
            260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly Lys
        355                 360


<210> SEQ ID NO 25
<211> LENGTH: 1083
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (73)..(396)

<400> SEQUENCE: 25

atggatgcaa tgaagagagg gctctgctgt gtgctgctgc tgtgtggagc agtcttcgtt      60

tcgcccggcg cc gct gag aca cgg gag tgc atc tac tac aac gcc aac tgg     111
              Ala Glu Thr Arg Glu Cys Ile Tyr Tyr Asn Ala Asn Trp
              1               5                   10

gag ctg gag cgc acc aac cag agc ggc ctg gag cgc tgc gaa ggc gag      159
Glu Leu Glu Arg Thr Asn Gln Ser Gly Leu Glu Arg Cys Glu Gly Glu
    15                  20                  25

cag gac aag cgg ctg cac tgc tac gcc tcc tgg cgc aac agc tct ggc      207
Gln Asp Lys Arg Leu His Cys Tyr Ala Ser Trp Arg Asn Ser Ser Gly
30                  35                  40                  45

acc atc gag ctc gtg aag aag ggc tgc tgg cta gat gac ttc aac tgc      255
Thr Ile Glu Leu Val Lys Lys Gly Cys Trp Leu Asp Asp Phe Asn Cys
                50                  55                  60

tac gat agg cag gag tgt gtg gcc act gag gag aac ccc cag gtg tac      303
Tyr Asp Arg Gln Glu Cys Val Ala Thr Glu Glu Asn Pro Gln Val Tyr
            65                  70                  75

ttc tgc tgc tgt gaa ggc aac ttc tgc aac gag cgc ttc act cat ttg      351
Phe Cys Cys Cys Glu Gly Asn Phe Cys Asn Glu Arg Phe Thr His Leu
        80                  85                  90

cca gag gct ggg ggc ccg gaa gtc acg tac gag cca ccc ccg aca          396
Pro Glu Ala Gly Gly Pro Glu Val Thr Tyr Glu Pro Pro Pro Thr
    95                  100                 105

ggtggtggaa ctcacacatg cccaccgtgc ccagcacctg aactcctggg gggaccgtca    456

gtcttcctct tccccccaaa acccaaggac accctcatga tctcccggac ccctgaggtc    516

acatgcgtgg tggtggacgt gagccacgaa gaccctgagg tcaagttcaa ctggtacgtg    576

gacggcgtgg aggtgcataa tgccaagaca aagccgcggg aggagcagta caacagcacg    636

taccgtgtgg tcagcgtcct caccgtcctg caccaggact ggctgaatgg caaggagtac    696

aagtgcaagg tctccaacaa agccctccca gcccccatcg agaaaaccat ctccaaagcc    756
```

-continued

```
aaagggcagc cccgagaacc acaggtgtac accctgcccc catcccggga ggagatgacc    816

aagaaccagg tcagcctgac ctgcctggtc aaaggcttct atcccagcga catcgccgtg    876

gagtgggaga gcaatgggca gccggagaac aactacaaga ccacgcctcc cgtgctggac    936

tccgacggct ccttcttcct ctatagcaag ctcaccgtgg acaagagcag gtggcagcag    996

gggaacgtct tctcatgctc cgtgatgcat gaggctctgc acaaccacta cacgcagaag   1056

agcctctccc tgtccccggg taaatga                                       1083


<210> SEQ ID NO 26
<211> LENGTH: 81
<212> TYPE: PRT
<213> ORGANISM: Homo sapiens

<400> SEQUENCE: 26

Cys Ile Tyr Tyr Asn Ala Asn Trp Glu Leu Glu Arg Thr Asn Gln Ser
1               5                   10                  15

Gly Leu Glu Arg Cys Glu Gly Glu Gln Asp Lys Arg Leu His Cys Tyr
            20                  25                  30

Ala Ser Trp Arg Asn Ser Ser Gly Thr Ile Glu Leu Val Lys Lys Gly
        35                  40                  45

Cys Trp Leu Asp Asp Phe Asn Cys Tyr Asp Arg Gln Glu Cys Val Ala
    50                  55                  60

Thr Glu Glu Asn Pro Gln Val Tyr Phe Cys Cys Cys Glu Gly Asn Phe
65                  70                  75                  80

Cys


<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Thr Gly Gly Gly
1


<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Gly Gly Gly Gly
1               5


<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Gly Gly Gly
1
```

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

```
Gly Gly Gly Gly
1
```

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 31

```
His His His His His His
1               5
```

<210> SEQ ID NO 32
<211> LENGTH: 368
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205
```

-continued

```
Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Val Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365


<210> SEQ ID NO 33
<211> LENGTH: 115
<212> TYPE: PRT
<213> ORGANISM: Homo sapiens

<400> SEQUENCE: 33

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115


<210> SEQ ID NO 34
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Ala Glu Thr Arg Glu Cys Ile Tyr Tyr Asn Ala Asn Trp Glu Leu Glu
1               5                   10                  15

Arg Thr Asn Gln Ser Gly Leu Glu Arg Cys Glu Gly Glu Gln Asp Lys
            20                  25                  30
```

-continued

```
Arg Leu His Cys Tyr Ala Ser Trp Arg Asn Ser Ser Gly Thr Ile Glu
        35                  40                  45

Leu Val Lys Lys Gly Cys Trp Leu Asp Asp Phe Asn Cys Tyr Asp Arg
    50                  55                  60

Gln Glu Cys Val Ala Thr Glu Glu Asn Pro Gln Val Tyr Phe Cys Cys
65                  70                  75                  80

Cys Glu Gly Asn Phe Cys Asn Glu Arg Phe Thr His Leu Pro Glu Ala
                85                  90                  95

Gly Gly Pro Glu Val Thr Tyr Glu Pro Pro Pro Thr
            100                 105
```